US011865082B2

(12) United States Patent
Codarri Deak et al.

(10) Patent No.: US 11,865,082 B2
(45) Date of Patent: Jan. 9, 2024

(54) COMBINATION THERAPY OF PD-1-TARGETED IL-2 VARIANT IMMUNOCYTOKINES AND ANTIBODIES AGAINST HUMAN PD-L1

(71) Applicant: Hoffman-La Roche Inc., Little Falls, NJ (US)

(72) Inventors: Laura Codarri Deak, Schlieren (CH); Douglas Hanahan, Saint-Sulpice (CH); Christian Klein, Schlieren (CH); Valeria Nicolini, Schlieren (CH); Pablo Umana, Schlieren (CH); Stephan Wullschleger, Urdorf (CH)

(73) Assignee: Hoffmann-La Roche Inc., Little Falls, NJ (US)

( * ) Notice: Subject to any disclaimer, the term of this patent is extended or adjusted under 35 U.S.C. 154(b) by 0 days.

(21) Appl. No.: 17/464,518

(22) Filed: Sep. 1, 2021

(65) Prior Publication Data

US 2022/0072103 A1 Mar. 10, 2022

Related U.S. Application Data

(60) Provisional application No. 63/076,020, filed on Sep. 9, 2020.

(51) Int. Cl.

| | |
|---|---|
| ***A61K 38/20*** | (2006.01) |
| ***A61K 35/17*** | (2015.01) |
| ***A61K 39/395*** | (2006.01) |
| ***A61P 35/00*** | (2006.01) |
| ***A61K 35/15*** | (2015.01) |
| ***A61K 38/17*** | (2006.01) |

(52) U.S. Cl.

CPC .......... *A61K 38/2013* (2013.01); *A61K 35/15* (2013.01); *A61K 35/17* (2013.01); *A61K 38/1774* (2013.01); *A61K 39/3955* (2013.01); *A61P 35/00* (2018.01)

(58) Field of Classification Search

CPC ................ A61K 38/2013; A61K 35/15; A61K 39/3955; A61P 35/00

See application file for complete search history.

(56) References Cited

U.S. PATENT DOCUMENTS

| | | | |
|---|---|---|---|
| 2012/0276125 A1 | 11/2012 | Ast et al. | |
| 2018/0326010 A1* | 11/2018 | Codarri Deak .... | A61K 39/3955 |
| 2020/0131267 A1 | 4/2020 | Carvalho et al. | |

FOREIGN PATENT DOCUMENTS

| | | |
|---|---|---|
| WO | WO-2015/048520 A1 | 4/2015 |
| WO | WO-2016/030350 A1 | 3/2016 |
| WO | WO-2017/055404 A1 | 4/2017 |
| WO | WO-2018/184964 A1 | 10/2018 |
| WO | WO-2019/014091 A1 | 1/2019 |

OTHER PUBLICATIONS

Desai et al; Abstract CT253: Preliminary safety and efficacy data of BGB-A333, an anti-PD-L1 monoclonal antibody, alone and in combination with tislelizumab in patients with advanced solid tumors. Cancer Res Aug. 15, 2020; 80 (16 Supplement): CT253. (Year: 2020).*

Cherkassky et al. Human CAR T cells with cell-intrinsic PD-1 checkpoint blockade resist tumor-mediated inhibition. J Clin Invest. 2016;126(8):3130-3144. (Year: 2016).*

Chen, X. et al. (2016). "Therapeutic Efficacy of an Anti-PD-L1 Antibody Based Immunocytokine in a Metastatic Mouse Model of Colorectal Cancer," *Biochemical and Biophysical Research Communications* 480(2016):160-165.

Klein, et al. (Jul. 1, 2019). "Abstract 1552: A Novel PD1-IL2v Immunocytokine for Preferential Cis-Activation of IL-2R Signaling on PD-1 Expressing T Cell Subsets Strongly Potentiates Anti-Tumor T Cell Activity of PD-1 Checkpoint Inhibition and IL-2R-beta-gamma Agonism,"*Cancer Res* 79(13_Supplement):1552.

Van Krinks, C.H. et al. (2019). "KY1043V, a Novel PD-L1 IL-2 Immunocytokine Directed Towards CD25, Delivers Potent Anti-Tumour Activity in vitro and in vivo," Abstract and Poster, SITC Nov. 6-10, 2019, 3 pages.

Pretto, F. et al. (Sep. 2013). "Pharmacotherapy of metastatic melanoma: emerging trends and opportunities for a cure," *Pharmacol Ther* 139(3):405-411.

Doberstein S.K. (Dec. 2019). "Bempegaldesleukin (NKTR-214): a CD-122-biased IL-2 receptor agonist for cancer immunotherapy," *Expert Opinion on Biological Therapy* 19(12):1223-1228.

Yang, B. et al. (Nov. 28, 2018). "Progresses and Perspectives of Anti-PD-1/PD-L1 Antibody Therapy Head and Neck Cancers," *Front Oncol* 8:563.

* cited by examiner

*Primary Examiner* — Aurora M Fontainhas
*Assistant Examiner* — Jennifer A Benavides
(74) *Attorney, Agent, or Firm* — MINTZ, LEVIN, COHN, FERRIS, GLOVSKY AND POPEO, P.C.

(57) ABSTRACT

The present invention relates to the combination therapy of specific PD-1-targeted IL-2 variant immunocytokines with specific antibodies which bind human PD-L1.

21 Claims, 4 Drawing Sheets
(3 of 4 Drawing Sheet(s) Filed in Color)
Specification includes a Sequence Listing.

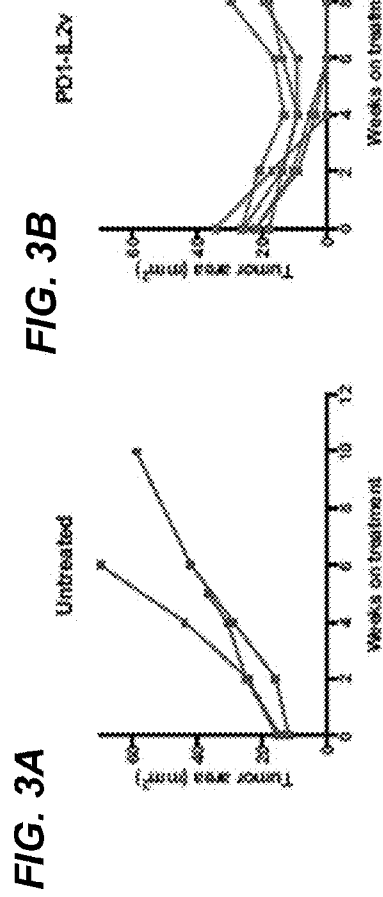
FIG. 3A
FIG. 3B
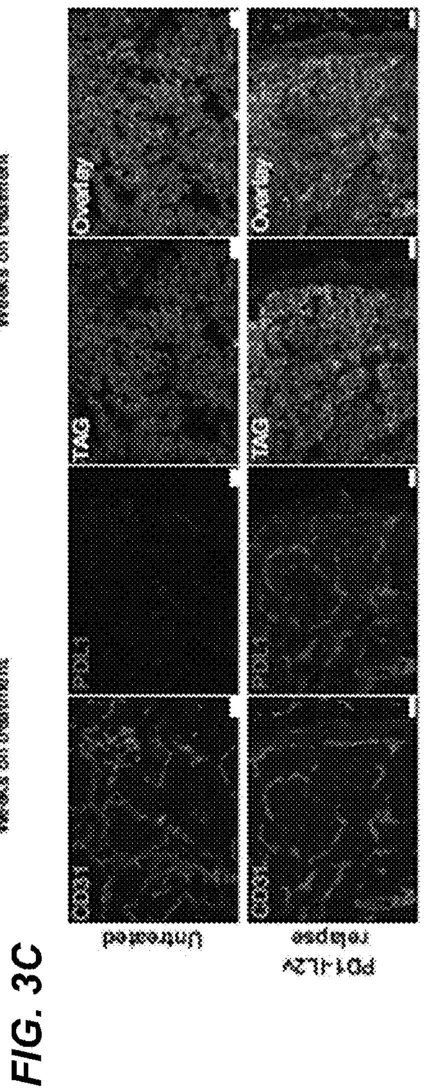
FIG. 3C
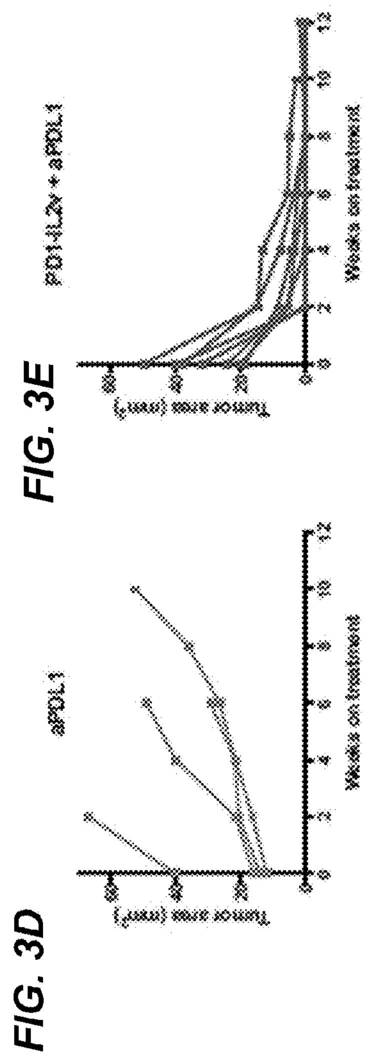
FIG. 3D
FIG. 3E

SEQUENCE LISTING

<160> NUMBER OF SEQ ID NOS: 29

<210> SEQ ID NO 1
<211> LENGTH: 133
<212> TYPE: PRT
<213> ORGANISM: Homo sapiens

<400> SEQUENCE: 1

```
Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60
```

```
Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ala Gln Ser Ile
        115                 120                 125

Ile Ser Thr Leu Thr
    130


<210> SEQ ID NO 2
<211> LENGTH: 133
<212> TYPE: PRT
<213> ORGANISM: Artificial Sequence
<220> FEATURE:
<223> OTHER INFORMATION: Synthetic Construct

<400> SEQUENCE: 2

Ala Pro Ala Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Ala Lys Phe Ala Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Gly Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ala Gln Ser Ile
        115                 120                 125

Ile Ser Thr Leu Thr
    130


<210> SEQ ID NO 3
<211> LENGTH: 290
<212> TYPE: PRT
<213> ORGANISM: Homo sapiens

<400> SEQUENCE: 3

Met Arg Ile Phe Ala Val Phe Ile Phe Met Thr Tyr Trp His Leu Leu
1               5                   10                  15

Asn Ala Phe Thr Val Thr Val Pro Lys Asp Leu Tyr Val Val Glu Tyr
            20                  25                  30

Gly Ser Asn Met Thr Ile Glu Cys Lys Phe Pro Val Glu Lys Gln Leu
        35                  40                  45

Asp Leu Ala Ala Leu Ile Val Tyr Trp Glu Met Glu Asp Lys Asn Ile
    50                  55                  60

Ile Gln Phe Val His Gly Glu Glu Asp Leu Lys Val Gln His Ser Ser
65                  70                  75                  80

Tyr Arg Gln Arg Ala Arg Leu Leu Lys Asp Gln Leu Ser Leu Gly Asn
                85                  90                  95
```

```
Ala Ala Leu Gln Ile Thr Asp Val Lys Leu Gln Asp Ala Gly Val Tyr
            100                 105                 110

Arg Cys Met Ile Ser Tyr Gly Gly Ala Asp Tyr Lys Arg Ile Thr Val
        115                 120                 125

Lys Val Asn Ala Pro Tyr Asn Lys Ile Asn Gln Arg Ile Leu Val Val
    130                 135                 140

Asp Pro Val Thr Ser Glu His Glu Leu Thr Cys Gln Ala Glu Gly Tyr
145                 150                 155                 160

Pro Lys Ala Glu Val Ile Trp Thr Ser Ser Asp His Gln Val Leu Ser
                165                 170                 175

Gly Lys Thr Thr Thr Thr Asn Ser Lys Arg Glu Glu Lys Leu Phe Asn
            180                 185                 190

Val Thr Ser Thr Leu Arg Ile Asn Thr Thr Thr Asn Glu Ile Phe Tyr
        195                 200                 205

Cys Thr Phe Arg Arg Leu Asp Pro Glu Glu Asn His Thr Ala Glu Leu
    210                 215                 220

Val Ile Pro Glu Leu Pro Leu Ala His Pro Pro Asn Glu Arg Thr His
225                 230                 235                 240

Leu Val Ile Leu Gly Ala Ile Leu Leu Cys Leu Gly Val Ala Leu Thr
                245                 250                 255

Phe Ile Phe Arg Leu Arg Lys Gly Arg Met Met Asp Val Lys Lys Cys
            260                 265                 270

Gly Ile Gln Asp Thr Asn Ser Lys Lys Gln Ser Asp Thr His Leu Glu
        275                 280                 285

Glu Thr
    290


<210> SEQ ID NO 4
<211> LENGTH: 288
<212> TYPE: PRT
<213> ORGANISM: Homo sapiens

<400> SEQUENCE: 4

Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
            20                  25                  30

Asn Pro Pro Thr Phe Ser Pro Ala Leu Leu Val Val Thr Glu Gly Asp
        35                  40                  45

Asn Ala Thr Phe Thr Cys Ser Phe Ser Asn Thr Ser Glu Ser Phe Val
    50                  55                  60

Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Gln Asp Cys Arg Phe Arg
                85                  90                  95

Val Thr Gln Leu Pro Asn Gly Arg Asp Phe His Met Ser Val Val Arg
            100                 105                 110

Ala Arg Arg Asn Asp Ser Gly Thr Tyr Leu Cys Gly Ala Ile Ser Leu
        115                 120                 125

Ala Pro Lys Ala Gln Ile Lys Glu Ser Leu Arg Ala Glu Leu Arg Val
    130                 135                 140

Thr Glu Arg Arg Ala Glu Val Pro Thr Ala His Pro Ser Pro Ser Pro
145                 150                 155                 160

Arg Pro Ala Gly Gln Phe Gln Thr Leu Val Val Gly Val Val Gly Gly
                165                 170                 175
```

```
Leu Leu Gly Ser Leu Val Leu Leu Val Trp Val Leu Ala Val Ile Cys
            180                 185                 190

Ser Arg Ala Ala Arg Gly Thr Ile Gly Ala Arg Arg Thr Gly Gln Pro
        195                 200                 205

Leu Lys Glu Asp Pro Ser Ala Val Pro Val Phe Ser Val Asp Tyr Gly
    210                 215                 220

Glu Leu Asp Phe Gln Trp Arg Glu Lys Thr Pro Glu Pro Pro Val Pro
225                 230                 235                 240

Cys Val Pro Glu Gln Thr Glu Tyr Ala Thr Ile Val Phe Pro Ser Gly
                245                 250                 255

Met Gly Thr Ser Ser Pro Ala Arg Arg Gly Ser Ala Asp Gly Pro Arg
            260                 265                 270

Ser Ala Gln Pro Leu Arg Pro Glu Asp Gly His Cys Ser Trp Pro Leu
        275                 280                 285


<210> SEQ ID NO 5
<211> LENGTH: 120
<212> TYPE: PRT
<213> ORGANISM: Artificial Sequence
<220> FEATURE:
<223> OTHER INFORMATION: Synthetic Construct

<400> SEQUENCE: 5

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Ser Phe Ser Ser Tyr
            20                  25                  30

Thr Met Ser Trp Val Arg Gln Ala Pro Gly Lys Gly Leu Glu Trp Val
        35                  40                  45

Ala Thr Ile Ser Gly Gly Gly Arg Asp Ile Tyr Tyr Pro Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Val Leu Leu Thr Gly Arg Val Tyr Phe Ala Leu Asp Ser Trp Gly Gln
            100                 105                 110

Gly Thr Leu Val Thr Val Ser Ser
        115                 120


<210> SEQ ID NO 6
<211> LENGTH: 111
<212> TYPE: PRT
<213> ORGANISM: Artificial Sequence
<220> FEATURE:
<223> OTHER INFORMATION: Synthetic Construct

<400> SEQUENCE: 6

Asp Ile Val Met Thr Gln Ser Pro Asp Ser Leu Ala Val Ser Leu Gly
1               5                   10                  15

Glu Arg Ala Thr Ile Asn Cys Lys Ala Ser Glu Ser Val Asp Thr Ser
            20                  25                  30

Asp Asn Ser Phe Ile His Trp Tyr Gln Gln Lys Pro Gly Gln Ser Pro
        35                  40                  45

Lys Leu Leu Ile Tyr Arg Ser Ser Thr Leu Glu Ser Gly Val Pro Asp
    50                  55                  60

Arg Phe Ser Gly Ser Gly Ser Gly Thr Asp Phe Thr Leu Thr Ile Ser
```

```
65                  70                  75                  80

Ser Leu Gln Ala Glu Asp Val Ala Val Tyr Tyr Cys Gln Gln Asn Tyr
                85                  90                  95

Asp Val Pro Trp Thr Phe Gly Gln Gly Thr Lys Val Glu Ile Lys
            100                 105                 110


<210> SEQ ID NO 7
<211> LENGTH: 597
<212> TYPE: PRT
<213> ORGANISM: Artificial Sequence
<220> FEATURE:
<223> OTHER INFORMATION: Synthetic Construct

<400> SEQUENCE: 7

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Ser Phe Ser Ser Tyr
            20                  25                  30

Thr Met Ser Trp Val Arg Gln Ala Pro Gly Lys Gly Leu Glu Trp Val
        35                  40                  45

Ala Thr Ile Ser Gly Gly Gly Arg Asp Ile Tyr Tyr Pro Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Val Leu Leu Thr Gly Arg Val Tyr Phe Ala Leu Asp Ser Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Ala Ala Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Gly Ala Pro Ile Glu
```

```
                325                 330                 335

Lys Thr Ile Ser Lys Ala Lys Gly Gln Pro Arg Glu Pro Gln Val Tyr
            340                 345                 350

Thr Leu Pro Pro Cys Arg Asp Glu Leu Thr Lys Asn Gln Val Ser Leu
        355                 360                 365

Trp Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Gly Gly Gly Gly Ser Gly Gly Gly Gly Ser Gly Gly Gly Gly Ser
    450                 455                 460

Ala Pro Ala Ser Ser Ser Thr Lys Lys Thr Gln Leu Gln Leu Glu His
465                 470                 475                 480

Leu Leu Leu Asp Leu Gln Met Ile Leu Asn Gly Ile Asn Asn Tyr Lys
                485                 490                 495

Asn Pro Lys Leu Thr Arg Met Leu Thr Ala Lys Phe Ala Met Pro Lys
            500                 505                 510

Lys Ala Thr Glu Leu Lys His Leu Gln Cys Leu Glu Glu Glu Leu Lys
        515                 520                 525

Pro Leu Glu Glu Val Leu Asn Gly Ala Gln Ser Lys Asn Phe His Leu
    530                 535                 540

Arg Pro Arg Asp Leu Ile Ser Asn Ile Asn Val Ile Val Leu Glu Leu
545                 550                 555                 560

Lys Gly Ser Glu Thr Thr Phe Met Cys Glu Tyr Ala Asp Glu Thr Ala
                565                 570                 575

Thr Ile Val Glu Phe Leu Asn Arg Trp Ile Thr Phe Ala Gln Ser Ile
            580                 585                 590

Ile Ser Thr Leu Thr
        595


<210> SEQ ID NO 8
<211> LENGTH: 448
<212> TYPE: PRT
<213> ORGANISM: Artificial Sequence
<220> FEATURE:
<223> OTHER INFORMATION: Synthetic Construct

<400> SEQUENCE: 8

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Ser Phe Ser Ser Tyr
            20                  25                  30

Thr Met Ser Trp Val Arg Gln Ala Pro Gly Lys Gly Leu Glu Trp Val
        35                  40                  45

Ala Thr Ile Ser Gly Gly Gly Arg Asp Ile Tyr Tyr Pro Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
```

```
                85                  90                  95

Val Leu Leu Thr Gly Arg Val Tyr Phe Ala Leu Asp Ser Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Ala Ala Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Gly Ala Pro Ile Glu
                325                 330                 335

Lys Thr Ile Ser Lys Ala Lys Gly Gln Pro Arg Glu Pro Gln Val Cys
            340                 345                 350

Thr Leu Pro Pro Ser Arg Asp Glu Leu Thr Lys Asn Gln Val Ser Leu
        355                 360                 365

Ser Cys Ala Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Val Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn Arg Phe Thr Gln Lys Ser Leu Ser Leu Ser Pro
        435                 440                 445
```

```
<210> SEQ ID NO 9
<211> LENGTH: 218
<212> TYPE: PRT
<213> ORGANISM: Artificial Sequence
<220> FEATURE:
<223> OTHER INFORMATION: Synthetic Construct

<400> SEQUENCE: 9

Asp Ile Val Met Thr Gln Ser Pro Asp Ser Leu Ala Val Ser Leu Gly
```

```
1               5                   10                  15

Glu Arg Ala Thr Ile Asn Cys Lys Ala Ser Glu Ser Val Asp Thr Ser
            20                  25                  30

Asp Asn Ser Phe Ile His Trp Tyr Gln Gln Lys Pro Gly Gln Ser Pro
        35                  40                  45

Lys Leu Leu Ile Tyr Arg Ser Ser Thr Leu Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Asn Tyr
                85                  90                  95

Asp Val Pro Trp Thr Phe Gly Gln Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215


<210> SEQ ID NO 10
<211> LENGTH: 450
<212> TYPE: PRT
<213> ORGANISM: Artificial Sequence
<220> FEATURE:
<223> OTHER INFORMATION: Synthetic Construct

<400> SEQUENCE: 10

Glu Val Gln Leu Gln Glu Ser Gly Pro Gly Leu Val Lys Pro Ser Gln
1               5                   10                  15

Ser Leu Ser Leu Thr Cys Ser Val Thr Gly Tyr Ser Ile Thr Ser Ser
            20                  25                  30

Tyr Arg Trp Asn Trp Ile Arg Lys Phe Pro Gly Asn Arg Leu Glu Trp
        35                  40                  45

Met Gly Tyr Ile Asn Ser Ala Gly Ile Ser Asn Tyr Asn Pro Ser Leu
    50                  55                  60

Lys Arg Arg Ile Ser Ile Thr Arg Asp Thr Ser Lys Asn Gln Phe Phe
65                  70                  75                  80

Leu Gln Val Asn Ser Val Thr Thr Glu Asp Ala Ala Thr Tyr Tyr Cys
                85                  90                  95

Ala Arg Ser Asp Asn Met Gly Thr Thr Pro Phe Thr Tyr Trp Gly Gln
            100                 105                 110

Gly Thr Leu Val Thr Val Ser Ser Ala Ser Thr Thr Ala Pro Ser Val
        115                 120                 125

Tyr Pro Leu Ala Pro Val Cys Gly Asp Thr Thr Gly Ser Ser Val Thr
    130                 135                 140

Leu Gly Cys Leu Val Lys Gly Tyr Phe Pro Glu Pro Val Thr Leu Thr
```

```
145                 150                 155                 160

Trp Asn Ser Gly Ser Leu Ser Ser Gly Val His Thr Phe Pro Ala Val
                165                 170                 175

Leu Gln Ser Asp Leu Tyr Thr Leu Ser Ser Ser Val Thr Val Thr Ser
            180                 185                 190

Ser Thr Trp Pro Ser Gln Ser Ile Thr Cys Asn Val Ala His Pro Ala
        195                 200                 205

Ser Ser Thr Lys Val Asp Lys Lys Ile Glu Pro Arg Gly Pro Thr Ile
    210                 215                 220

Lys Pro Cys Pro Pro Cys Lys Cys Pro Ala Pro Asn Ala Ala Gly Gly
225                 230                 235                 240

Pro Ser Val Phe Ile Phe Pro Pro Lys Ile Lys Asp Val Leu Met Ile
                245                 250                 255

Ser Leu Ser Pro Ile Val Thr Cys Val Val Val Asp Val Ser Glu Asp
            260                 265                 270

Asp Pro Asp Val Gln Ile Ser Trp Phe Val Asn Asn Val Glu Val His
        275                 280                 285

Thr Ala Gln Thr Gln Thr His Arg Glu Asp Tyr Asn Ser Thr Leu Arg
    290                 295                 300

Val Val Ser Ala Leu Pro Ile Gln His Gln Asp Trp Met Ser Gly Lys
305                 310                 315                 320

Glu Phe Lys Cys Lys Val Asn Asn Lys Asp Leu Gly Ala Pro Ile Glu
                325                 330                 335

Arg Thr Ile Ser Lys Pro Lys Gly Ser Val Arg Ala Pro Gln Val Tyr
            340                 345                 350

Val Leu Pro Pro Pro Glu Glu Glu Met Thr Lys Lys Gln Val Thr Leu
        355                 360                 365

Thr Cys Met Val Thr Asp Phe Met Pro Glu Asp Ile Tyr Val Glu Trp
    370                 375                 380

Thr Asn Asn Gly Lys Thr Glu Leu Asn Tyr Lys Asn Thr Glu Pro Val
385                 390                 395                 400

Leu Asp Ser Asp Gly Ser Tyr Phe Met Tyr Ser Lys Leu Arg Val Glu
                405                 410                 415

Lys Lys Asn Trp Val Glu Arg Asn Ser Tyr Ser Cys Ser Val Val His
            420                 425                 430

Glu Gly Leu His Asn His His Thr Thr Lys Ser Phe Ser Arg Thr Pro
        435                 440                 445

Gly Lys
    450
```

<210> SEQ ID NO 11
<211> LENGTH: 218
<212> TYPE: PRT
<213> ORGANISM: Artificial Sequence
<220> FEATURE:
<223> OTHER INFORMATION: Synthetic Construct

<400> SEQUENCE: 11

```
Asp Ile Val Met Thr Gln Gly Thr Leu Pro Asn Pro Val Pro Ser Gly
1               5                   10                  15

Glu Ser Val Ser Ile Thr Cys Arg Ser Ser Lys Ser Leu Leu Tyr Ser
            20                  25                  30

Asp Gly Lys Thr Tyr Leu Asn Trp Tyr Leu Gln Arg Pro Gly Gln Ser
        35                  40                  45

Pro Gln Leu Leu Ile Tyr Trp Met Ser Thr Arg Ala Ser Gly Val Ser
```

```
    50                  55                  60

Asp Arg Phe Ser Gly Ser Gly Ser Gly Thr Asp Phe Thr Leu Lys Ile
65                  70                  75                  80

Ser Gly Val Glu Ala Glu Asp Val Gly Ile Tyr Tyr Cys Gln Gln Gly
                85                  90                  95

Leu Glu Phe Pro Thr Phe Gly Gly Gly Thr Lys Leu Glu Leu Lys Arg
            100                 105                 110

Thr Asp Ala Ala Pro Thr Val Ser Ile Phe Pro Pro Ser Ser Glu Gln
        115                 120                 125

Leu Thr Ser Gly Gly Ala Ser Val Val Cys Phe Leu Asn Asn Phe Tyr
    130                 135                 140

Pro Lys Asp Ile Asn Val Lys Trp Lys Ile Asp Gly Ser Glu Arg Gln
145                 150                 155                 160

Asn Gly Val Leu Asn Ser Trp Thr Asp Gln Asp Ser Lys Asp Ser Thr
                165                 170                 175

Tyr Ser Met Ser Ser Thr Leu Thr Leu Thr Lys Asp Glu Tyr Glu Arg
            180                 185                 190

His Asn Ser Tyr Thr Cys Glu Ala Thr His Lys Thr Ser Thr Ser Pro
        195                 200                 205

Ile Val Lys Ser Phe Asn Arg Asn Glu Cys
    210                 215


<210> SEQ ID NO 12
<211> LENGTH: 607
<212> TYPE: PRT
<213> ORGANISM: Artificial Sequence
<220> FEATURE:
<223> OTHER INFORMATION: Synthetic Construct

<400> SEQUENCE: 12

Glu Val Gln Leu Gln Glu Ser Gly Pro Gly Leu Val Lys Pro Ser Gln
1               5                   10                  15

Ser Leu Ser Leu Thr Cys Ser Val Thr Gly Tyr Ser Ile Thr Ser Ser
            20                  25                  30

Tyr Arg Trp Asn Trp Ile Arg Lys Phe Pro Gly Asn Arg Leu Glu Trp
        35                  40                  45

Met Gly Tyr Ile Asn Ser Ala Gly Ile Ser Asn Tyr Asn Pro Ser Leu
    50                  55                  60

Lys Arg Arg Ile Ser Ile Thr Arg Asp Thr Ser Lys Asn Gln Phe Phe
65                  70                  75                  80

Leu Gln Val Asn Ser Val Thr Thr Glu Asp Ala Ala Thr Tyr Tyr Cys
                85                  90                  95

Ala Arg Ser Asp Asn Met Gly Thr Thr Pro Phe Thr Tyr Trp Gly Gln
            100                 105                 110

Gly Thr Leu Val Thr Val Ser Ser Ala Lys Thr Thr Pro Pro Ser Val
        115                 120                 125

Tyr Pro Leu Ala Pro Gly Ser Ala Ala Gln Thr Asn Ser Met Val Thr
    130                 135                 140

Leu Gly Cys Leu Val Lys Gly Tyr Phe Pro Glu Pro Val Thr Val Thr
145                 150                 155                 160

Trp Asn Ser Gly Ser Leu Ser Ser Gly Val His Thr Phe Pro Ala Val
                165                 170                 175

Leu Gln Ser Asp Leu Tyr Thr Leu Ser Ser Ser Val Thr Val Pro Ser
            180                 185                 190

Ser Thr Trp Pro Ser Gln Thr Val Thr Cys Asn Val Ala His Pro Ala
```

```
        195                 200                 205

Ser Ser Thr Lys Val Asp Lys Lys Ile Val Pro Arg Asp Cys Gly Cys
    210                 215                 220

Lys Pro Cys Ile Cys Thr Val Pro Glu Val Ser Ser Val Phe Ile Phe
225                 230                 235                 240

Pro Pro Lys Pro Lys Asp Val Leu Thr Ile Thr Leu Thr Pro Lys Val
                245                 250                 255

Thr Cys Val Val Val Ala Ile Ser Lys Asp Asp Pro Glu Val Gln Phe
            260                 265                 270

Ser Trp Phe Val Asp Asp Val Glu Val His Thr Ala Gln Thr Lys Pro
        275                 280                 285

Arg Glu Glu Gln Ile Asn Ser Thr Phe Arg Ser Val Ser Glu Leu Pro
    290                 295                 300

Ile Met His Gln Asp Trp Leu Asn Gly Lys Glu Phe Lys Cys Arg Val
305                 310                 315                 320

Asn Ser Ala Ala Phe Gly Ala Pro Ile Glu Lys Thr Ile Ser Lys Thr
                325                 330                 335

Lys Gly Arg Pro Lys Ala Pro Gln Val Tyr Thr Ile Pro Pro Pro Lys
            340                 345                 350

Glu Gln Met Ala Lys Asp Lys Val Ser Leu Thr Cys Met Ile Thr Asn
        355                 360                 365

Phe Phe Pro Glu Asp Ile Thr Val Glu Trp Gln Trp Asn Gly Gln Pro
    370                 375                 380

Ala Glu Asn Tyr Asp Asn Thr Gln Pro Ile Met Asp Thr Asp Gly Ser
385                 390                 395                 400

Tyr Phe Val Tyr Ser Asp Leu Asn Val Gln Lys Ser Asn Trp Glu Ala
                405                 410                 415

Gly Asn Thr Phe Thr Cys Ser Val Leu His Glu Gly Leu His Asn His
            420                 425                 430

His Thr Glu Lys Ser Leu Ser His Ser Pro Gly Gly Gly Gly Gly Ser
        435                 440                 445

Gly Gly Gly Gly Ser Gly Gly Gly Gly Ser Ala Pro Ala Ser Ser Ser
    450                 455                 460

Thr Ser Ser Ser Thr Ala Glu Ala Gln Gln Gln Gln Gln Gln Gln Gln
465                 470                 475                 480

Gln Gln Gln Gln His Leu Glu Gln Leu Leu Met Asp Leu Gln Glu Leu
                485                 490                 495

Leu Ser Arg Met Glu Asn Tyr Arg Asn Leu Lys Leu Pro Arg Met Leu
            500                 505                 510

Thr Ala Lys Phe Ala Leu Pro Lys Gln Ala Thr Glu Leu Lys Asp Leu
        515                 520                 525

Gln Cys Leu Glu Asp Glu Leu Gly Pro Leu Arg His Val Leu Asp Gly
    530                 535                 540

Thr Gln Ser Lys Ser Phe Gln Leu Glu Asp Ala Glu Asn Phe Ile Ser
545                 550                 555                 560

Asn Ile Arg Val Thr Val Val Lys Leu Lys Gly Ser Asp Asn Thr Phe
                565                 570                 575

Glu Cys Gln Phe Asp Asp Glu Ser Ala Thr Val Val Asp Phe Leu Arg
            580                 585                 590

Arg Trp Ile Ala Phe Ala Gln Ser Ile Ile Ser Thr Ser Pro Gln
        595                 600                 605
```

<210> SEQ ID NO 13

<211> LENGTH: 442
<212> TYPE: PRT
<213> ORGANISM: Artificial Sequence
<220> FEATURE:
<223> OTHER INFORMATION: Synthetic Construct

<400> SEQUENCE: 13

```
Glu Val Gln Leu Gln Glu Ser Gly Pro Gly Leu Val Lys Pro Ser Gln
1               5                   10                  15

Ser Leu Ser Leu Thr Cys Ser Val Thr Gly Tyr Ser Ile Thr Ser Ser
            20                  25                  30

Tyr Arg Trp Asn Trp Ile Arg Lys Phe Pro Gly Asn Arg Leu Glu Trp
        35                  40                  45

Met Gly Tyr Ile Asn Ser Ala Gly Ile Ser Asn Tyr Asn Pro Ser Leu
    50                  55                  60

Lys Arg Arg Ile Ser Ile Thr Arg Asp Thr Ser Lys Asn Gln Phe Phe
65                  70                  75                  80

Leu Gln Val Asn Ser Val Thr Thr Glu Asp Ala Ala Thr Tyr Tyr Cys
                85                  90                  95

Ala Arg Ser Asp Asn Met Gly Thr Thr Pro Phe Thr Tyr Trp Gly Gln
            100                 105                 110

Gly Thr Leu Val Thr Val Ser Ser Ala Lys Thr Thr Pro Pro Ser Val
        115                 120                 125

Tyr Pro Leu Ala Pro Gly Ser Ala Ala Gln Thr Asn Ser Met Val Thr
    130                 135                 140

Leu Gly Cys Leu Val Lys Gly Tyr Phe Pro Glu Pro Val Thr Val Thr
145                 150                 155                 160

Trp Asn Ser Gly Ser Leu Ser Ser Gly Val His Thr Phe Pro Ala Val
                165                 170                 175

Leu Gln Ser Asp Leu Tyr Thr Leu Ser Ser Ser Val Thr Val Pro Ser
            180                 185                 190

Ser Thr Trp Pro Ser Gln Thr Val Thr Cys Asn Val Ala His Pro Ala
        195                 200                 205

Ser Ser Thr Lys Val Asp Lys Lys Ile Val Pro Arg Asp Cys Gly Cys
    210                 215                 220

Lys Pro Cys Ile Cys Thr Val Pro Glu Val Ser Ser Val Phe Ile Phe
225                 230                 235                 240

Pro Pro Lys Pro Lys Asp Val Leu Thr Ile Thr Leu Thr Pro Lys Val
                245                 250                 255

Thr Cys Val Val Val Ala Ile Ser Lys Asp Asp Pro Glu Val Gln Phe
            260                 265                 270

Ser Trp Phe Val Asp Asp Val Glu Val His Thr Ala Gln Thr Lys Pro
        275                 280                 285

Arg Glu Glu Gln Ile Asn Ser Thr Phe Arg Ser Val Ser Glu Leu Pro
    290                 295                 300

Ile Met His Gln Asp Trp Leu Asn Gly Lys Glu Phe Lys Cys Arg Val
305                 310                 315                 320

Asn Ser Ala Ala Phe Gly Ala Pro Ile Glu Lys Thr Ile Ser Lys Thr
                325                 330                 335

Lys Gly Arg Pro Lys Ala Pro Gln Val Tyr Thr Ile Pro Pro Pro Lys
            340                 345                 350

Lys Gln Met Ala Lys Asp Lys Val Ser Leu Thr Cys Met Ile Thr Asn
        355                 360                 365

Phe Phe Pro Glu Asp Ile Thr Val Glu Trp Gln Trp Asn Gly Gln Pro
    370                 375                 380
```

```
Ala Glu Asn Tyr Lys Asn Thr Gln Pro Ile Met Lys Thr Asp Gly Ser
385                 390                 395                 400

Tyr Phe Val Tyr Ser Lys Leu Asn Val Gln Lys Ser Asn Trp Glu Ala
                405                 410                 415

Gly Asn Thr Phe Thr Cys Ser Val Leu His Glu Gly Leu His Asn His
            420                 425                 430

His Thr Glu Lys Ser Leu Ser His Ser Pro
        435                 440


<210> SEQ ID NO 14
<211> LENGTH: 218
<212> TYPE: PRT
<213> ORGANISM: Artificial Sequence
<220> FEATURE:
<223> OTHER INFORMATION: Synthetic Construct

<400> SEQUENCE: 14

Asp Ile Val Met Thr Gln Gly Thr Leu Pro Asn Pro Val Pro Ser Gly
1               5                   10                  15

Glu Ser Val Ser Ile Thr Cys Arg Ser Ser Lys Ser Leu Leu Tyr Ser
            20                  25                  30

Asp Gly Lys Thr Tyr Leu Asn Trp Tyr Leu Gln Arg Pro Gly Gln Ser
        35                  40                  45

Pro Gln Leu Leu Ile Tyr Trp Met Ser Thr Arg Ala Ser Gly Val Ser
    50                  55                  60

Asp Arg Phe Ser Gly Ser Gly Ser Gly Thr Asp Phe Thr Leu Lys Ile
65                  70                  75                  80

Ser Gly Val Glu Ala Glu Asp Val Gly Ile Tyr Tyr Cys Gln Gln Gly
                85                  90                  95

Leu Glu Phe Pro Thr Phe Gly Gly Gly Thr Lys Leu Glu Leu Lys Arg
            100                 105                 110

Thr Asp Ala Ala Pro Thr Val Ser Ile Phe Pro Pro Ser Ser Glu Gln
        115                 120                 125

Leu Thr Ser Gly Gly Ala Ser Val Val Cys Phe Leu Asn Asn Phe Tyr
    130                 135                 140

Pro Lys Asp Ile Asn Val Lys Trp Lys Ile Asp Gly Ser Glu Arg Gln
145                 150                 155                 160

Asn Gly Val Leu Asn Ser Trp Thr Asp Gln Asp Ser Lys Asp Ser Thr
                165                 170                 175

Tyr Ser Met Ser Ser Thr Leu Thr Leu Thr Lys Asp Glu Tyr Glu Arg
            180                 185                 190

His Asn Ser Tyr Thr Cys Glu Ala Thr His Lys Thr Ser Thr Ser Pro
        195                 200                 205

Ile Val Lys Ser Phe Asn Arg Asn Glu Cys
    210                 215


<210> SEQ ID NO 15
<211> LENGTH: 118
<212> TYPE: PRT
<213> ORGANISM: Artificial Sequence
<220> FEATURE:
<223> OTHER INFORMATION: Synthetic Construct

<400> SEQUENCE: 15

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ser
```

```
            20                  25                  30

Trp Ile His Trp Val Arg Gln Ala Pro Gly Lys Gly Leu Glu Trp Val
        35                  40                  45

Ala Trp Ile Ser Pro Tyr Gly Gly Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Arg His Trp Pro Gly Gly Phe Asp Tyr Trp Gly Gln Gly Thr
            100                 105                 110

Leu Val Thr Val Ser Ser
        115


<210> SEQ ID NO 16
<211> LENGTH: 107
<212> TYPE: PRT
<213> ORGANISM: Artificial Sequence
<220> FEATURE:
<223> OTHER INFORMATION: Synthetic Construct

<400> SEQUENCE: 16

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Leu Tyr His Pro Ala
                85                  90                  95

Thr Phe Gly Gln Gly Thr Lys Val Glu Ile Lys
            100                 105


<210> SEQ ID NO 17
<211> LENGTH: 448
<212> TYPE: PRT
<213> ORGANISM: Artificial Sequence
<220> FEATURE:
<223> OTHER INFORMATION: Synthetic Construct

<400> SEQUENCE: 17

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ser
            20                  25                  30

Trp Ile His Trp Val Arg Gln Ala Pro Gly Lys Gly Leu Glu Trp Val
        35                  40                  45

Ala Trp Ile Ser Pro Tyr Gly Gly Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95
```

```
Ala Arg Arg His Trp Pro Gly Gly Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Ala Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445


<210> SEQ ID NO 18
<211> LENGTH: 214
<212> TYPE: PRT
<213> ORGANISM: Artificial Sequence
<220> FEATURE:
<223> OTHER INFORMATION: Synthetic Construct

<400> SEQUENCE: 18

Asp Ile Gln Met Thr Gln Ser Pro Ser Ser Leu Ser Ala Ser Val Gly
1               5                   10                  15
```

```
Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Leu Tyr His Pro Ala
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 19
<211> LENGTH: 117
<212> TYPE: PRT
<213> ORGANISM: Artificial Sequence
<220> FEATURE:
<223> OTHER INFORMATION: Synthetic Construct

<400> SEQUENCE: 19

Glu Val Gln Leu Gln Gln Ser Gly Pro Glu Leu Val Lys Pro Gly Ala
1               5                   10                  15

Ser Val Lys Leu Ser Cys Lys Thr Ser Gly Thr Phe Thr Asp Tyr Tyr
            20                  25                  30

Met Thr Trp Val Lys Gln Ser His Gly Lys Ser Leu Glu Trp Ile Gly
        35                  40                  45

Asp Ile Asn Pro Asn Asn Asp Ile Ile Thr Tyr Asn Gln Lys Phe Asn
    50                  55                  60

Asp Lys Ala Thr Leu Thr Val Asp Lys Ser Ser Ser Thr Ala Ser Met
65                  70                  75                  80

Glu Leu Arg Ser Leu Arg Ser Asp Asp Ser Ala Val Tyr Tyr Cys Ala
                85                  90                  95

Arg Gly Asp Pro Arg Ser Trp Phe Pro Tyr Trp Gly Gln Gly Thr Leu
            100                 105                 110

Val Thr Val Ser Ala
        115


<210> SEQ ID NO 20
<211> LENGTH: 110
<212> TYPE: PRT
<213> ORGANISM: Artificial Sequence
<220> FEATURE:
```

<223> OTHER INFORMATION: Synthetic Construct

<400> SEQUENCE: 20

```
Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Glu Phe Tyr
            20                  25                  30

Gly Ser Leu Met Arg Trp Tyr Gln Gln Lys Pro Gly Gln Pro Pro Lys
        35                  40                  45

Leu Leu Ile Tyr Ala Ala Ser Asn Val Glu Ser Gly Val Pro Ala Arg
    50                  55                  60

Phe Ser Gly Ser Gly Ser Gly Thr Asp Phe Ser Leu Asn Ile His Pro
65                  70                  75                  80

Val Glu Glu Asp Asp Ile Ala Met Tyr Phe Cys Gln Gln Ser Arg Lys
                85                  90                  95

Val Pro Leu Thr Phe Gly Ala Gly Thr Lys Leu Glu Ile Lys
            100                 105                 110
```

<210> SEQ ID NO 21
<211> LENGTH: 442
<212> TYPE: PRT
<213> ORGANISM: Artificial Sequence
<220> FEATURE:
<223> OTHER INFORMATION: Synthetic Construct

<400> SEQUENCE: 21

```
Glu Val Gln Leu Gln Gln Ser Gly Pro Glu Leu Val Lys Pro Gly Ala
1               5                   10                  15

Ser Val Lys Leu Ser Cys Lys Thr Ser Gly Tyr Thr Phe Thr Asp Tyr
            20                  25                  30

Tyr Met Thr Trp Val Lys Gln Ser His Gly Lys Ser Leu Glu Trp Ile
        35                  40                  45

Gly Asp Ile Asn Pro Asn Asn Asp Ile Ile Thr Tyr Asn Gln Lys Phe
    50                  55                  60

Asn Asp Lys Ala Thr Leu Thr Val Asp Lys Ser Ser Ser Thr Ala Ser
65                  70                  75                  80

Met Glu Leu Arg Ser Leu Arg Ser Asp Asp Ser Ala Val Tyr Tyr Cys
                85                  90                  95

Ala Arg Gly Asp Pro Arg Ser Trp Phe Pro Tyr Trp Gly Gln Gly Thr
            100                 105                 110

Leu Val Thr Val Ser Ala Ala Lys Thr Thr Pro Pro Ser Val Tyr Pro
        115                 120                 125

Leu Ala Pro Gly Ser Ala Ala Gln Thr Asn Ser Met Val Thr Leu Gly
    130                 135                 140

Cys Leu Val Lys Gly Tyr Phe Pro Glu Pro Val Thr Val Thr Trp Asn
145                 150                 155                 160

Ser Gly Ser Leu Ser Ser Gly Val His Thr Phe Pro Ala Val Leu Gln
                165                 170                 175

Ser Asp Leu Tyr Thr Leu Ser Ser Ser Val Thr Val Pro Ser Ser Thr
            180                 185                 190

Trp Pro Ser Gln Thr Val Thr Cys Asn Val Ala His Pro Ala Ser Ser
        195                 200                 205

Thr Lys Val Asp Lys Lys Ile Val Pro Arg Asp Cys Gly Cys Lys Pro
    210                 215                 220

Cys Ile Cys Thr Val Pro Glu Val Ser Ser Val Phe Ile Phe Pro Pro
225                 230                 235                 240
```

```
Lys Pro Lys Asp Val Leu Thr Ile Thr Leu Thr Pro Lys Val Thr Cys
                245                 250                 255

Val Val Val Ala Ile Ser Lys Asp Asp Pro Glu Val Gln Phe Ser Trp
            260                 265                 270

Phe Val Asp Asp Val Glu Val His Thr Ala Gln Thr Lys Pro Arg Glu
        275                 280                 285

Glu Gln Ile Asn Ser Thr Phe Arg Ser Val Ser Glu Leu Pro Ile Met
    290                 295                 300

His Gln Asp Trp Leu Asn Gly Lys Glu Phe Lys Cys Arg Val Asn Ser
305                 310                 315                 320

Ala Ala Phe Gly Ala Pro Ile Glu Lys Thr Ile Ser Lys Thr Lys Gly
                325                 330                 335

Arg Pro Lys Ala Pro Gln Val Tyr Thr Ile Pro Pro Pro Lys Glu Gln
            340                 345                 350

Met Ala Lys Asp Lys Val Ser Leu Thr Cys Met Ile Thr Asn Phe Phe
        355                 360                 365

Pro Glu Asp Ile Thr Val Glu Trp Gln Trp Asn Gly Gln Pro Ala Glu
    370                 375                 380

Asn Tyr Lys Asn Thr Gln Pro Ile Met Asp Thr Asp Gly Ser Tyr Phe
385                 390                 395                 400

Val Tyr Ser Lys Leu Asn Val Gln Lys Ser Asn Trp Glu Ala Gly Asn
                405                 410                 415

Thr Phe Thr Cys Ser Val Leu His Glu Gly Leu His Asn His His Thr
            420                 425                 430

Glu Lys Ser Leu Ser His Ser Pro Gly Lys
        435                 440
```

<210> SEQ ID NO 22
<211> LENGTH: 218
<212> TYPE: PRT
<213> ORGANISM: Artificial Sequence
<220> FEATURE:
<223> OTHER INFORMATION: Synthetic Construct

<400> SEQUENCE: 22

```
Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Glu Phe Tyr
            20                  25                  30

Gly Thr Ser Leu Met Arg Trp Tyr Gln Gln Lys Pro Gly Gln Pro Pro
        35                  40                  45

Lys Leu Leu Ile Tyr Ala Ala Ser Asn Val Glu Ser Gly Val Pro Ala
    50                  55                  60

Arg Phe Ser Gly Ser Gly Ser Gly Thr Asp Phe Ser Leu Asn Ile His
65                  70                  75                  80

Pro Val Glu Glu Asp Asp Ile Ala Met Tyr Phe Cys Gln Gln Ser Arg
                85                  90                  95

Lys Val Pro Leu Thr Phe Gly Ala Gly Thr Lys Leu Glu Ile Lys Arg
            100                 105                 110

Ala Asp Ala Ala Pro Thr Val Ser Ile Phe Pro Pro Ser Ser Glu Gln
        115                 120                 125

Leu Thr Ser Gly Gly Ala Ser Val Val Cys Phe Leu Asn Asn Phe Tyr
    130                 135                 140

Pro Lys Asp Ile Asn Val Lys Trp Lys Ile Asp Gly Ser Glu Arg Gln
145                 150                 155                 160
```

```
Asn Gly Val Leu Asn Ser Trp Thr Asp Gln Asp Ser Lys Asp Ser Thr
                165                 170                 175

Tyr Ser Met Ser Ser Thr Leu Thr Leu Thr Lys Asp Glu Tyr Glu Arg
            180                 185                 190

His Asn Ser Tyr Thr Cys Glu Ala Thr His Lys Thr Ser Thr Ser Pro
        195                 200                 205

Ile Val Lys Ser Phe Asn Arg Asn Glu Cys
    210                 215


<210> SEQ ID NO 23
<211> LENGTH: 450
<212> TYPE: PRT
<213> ORGANISM: Artificial Sequence
<220> FEATURE:
<223> OTHER INFORMATION: Synthetic Construct

<400> SEQUENCE: 23

Glu Val Gln Leu Gln Glu Ser Gly Pro Gly Leu Val Lys Pro Ser Gln
1               5                   10                  15

Ser Leu Ser Leu Thr Cys Ser Val Thr Gly Tyr Ser Ile Thr Ser Ser
            20                  25                  30

Tyr Arg Trp Asn Trp Ile Arg Lys Phe Pro Gly Asn Arg Leu Glu Trp
        35                  40                  45

Met Gly Tyr Ile Asn Ser Ala Gly Ile Ser Asn Tyr Asn Pro Ser Leu
    50                  55                  60

Lys Arg Arg Ile Ser Ile Thr Arg Asp Thr Ser Lys Asn Gln Phe Phe
65                  70                  75                  80

Leu Gln Val Asn Ser Val Thr Thr Glu Asp Ala Ala Thr Tyr Tyr Cys
                85                  90                  95

Ala Arg Ser Asp Asn Met Gly Thr Thr Pro Phe Thr Tyr Trp Gly Gln
            100                 105                 110

Gly Thr Leu Val Thr Val Ser Ser Ala Ser Thr Thr Ala Pro Ser Val
        115                 120                 125

Tyr Pro Leu Ala Pro Val Cys Gly Asp Thr Thr Gly Ser Ser Val Thr
    130                 135                 140

Leu Gly Cys Leu Val Lys Gly Tyr Phe Pro Glu Pro Val Thr Leu Thr
145                 150                 155                 160

Trp Asn Ser Gly Ser Leu Ser Ser Gly Val His Thr Phe Pro Ala Val
                165                 170                 175

Leu Gln Ser Asp Leu Tyr Thr Leu Ser Ser Ser Val Thr Val Thr Ser
            180                 185                 190

Ser Thr Trp Pro Ser Gln Ser Ile Thr Cys Asn Val Ala His Pro Ala
        195                 200                 205

Ser Ser Thr Lys Val Asp Lys Lys Ile Glu Pro Arg Gly Pro Thr Ile
    210                 215                 220

Lys Pro Cys Pro Pro Cys Lys Cys Pro Ala Pro Asn Ala Ala Gly Gly
225                 230                 235                 240

Pro Ser Val Phe Ile Phe Pro Pro Lys Ile Lys Asp Val Leu Met Ile
                245                 250                 255

Ser Leu Ser Pro Ile Val Thr Cys Val Val Val Asp Val Ser Glu Asp
            260                 265                 270

Asp Pro Asp Val Gln Ile Ser Trp Phe Val Asn Asn Val Glu Val His
        275                 280                 285

Thr Ala Gln Thr Gln Thr His Arg Glu Asp Tyr Asn Ser Thr Leu Arg
    290                 295                 300
```

```
Val Val Ser Ala Leu Pro Ile Gln His Gln Asp Trp Met Ser Gly Lys
305                 310                 315                 320

Glu Phe Lys Cys Lys Val Asn Asn Lys Asp Leu Gly Ala Pro Ile Glu
                325                 330                 335

Arg Thr Ile Ser Lys Pro Lys Gly Ser Val Arg Ala Pro Gln Val Tyr
            340                 345                 350

Val Leu Pro Pro Pro Glu Glu Glu Met Thr Lys Lys Gln Val Thr Leu
        355                 360                 365

Thr Cys Met Val Thr Asp Phe Met Pro Glu Asp Ile Tyr Val Glu Trp
    370                 375                 380

Thr Asn Asn Gly Lys Thr Glu Leu Asn Tyr Lys Asn Thr Glu Pro Val
385                 390                 395                 400

Leu Asp Ser Asp Gly Ser Tyr Phe Met Tyr Ser Lys Leu Arg Val Glu
                405                 410                 415

Lys Lys Asn Trp Val Glu Arg Asn Ser Tyr Ser Cys Ser Val Val His
            420                 425                 430

Glu Gly Leu His Asn His His Thr Thr Lys Ser Phe Ser Arg Thr Pro
        435                 440                 445

Gly Lys
    450


<210> SEQ ID NO 24
<211> LENGTH: 218
<212> TYPE: PRT
<213> ORGANISM: Artificial Sequence
<220> FEATURE:
<223> OTHER INFORMATION: Synthetic Construct

<400> SEQUENCE: 24

Asp Ile Val Met Thr Gln Gly Thr Leu Pro Asn Pro Val Pro Ser Gly
1               5                   10                  15

Glu Ser Val Ser Ile Thr Cys Arg Ser Ser Lys Ser Leu Leu Tyr Ser
            20                  25                  30

Asp Gly Lys Thr Tyr Leu Asn Trp Tyr Leu Gln Arg Pro Gly Gln Ser
        35                  40                  45

Pro Gln Leu Leu Ile Tyr Trp Met Ser Thr Arg Ala Ser Gly Val Ser
    50                  55                  60

Asp Arg Phe Ser Gly Ser Gly Ser Gly Thr Asp Phe Thr Leu Lys Ile
65                  70                  75                  80

Ser Gly Val Glu Ala Glu Asp Val Gly Ile Tyr Tyr Cys Gln Gln Gly
                85                  90                  95

Leu Glu Phe Pro Thr Phe Gly Gly Gly Thr Lys Leu Glu Leu Lys Arg
            100                 105                 110

Thr Asp Ala Ala Pro Thr Val Ser Ile Phe Pro Pro Ser Ser Glu Gln
        115                 120                 125

Leu Thr Ser Gly Gly Ala Ser Val Val Cys Phe Leu Asn Asn Phe Tyr
    130                 135                 140

Pro Lys Asp Ile Asn Val Lys Trp Lys Ile Asp Gly Ser Glu Arg Gln
145                 150                 155                 160

Asn Gly Val Leu Asn Ser Trp Thr Asp Gln Asp Ser Lys Asp Ser Thr
                165                 170                 175

Tyr Ser Met Ser Ser Thr Leu Thr Leu Thr Lys Asp Glu Tyr Glu Arg
            180                 185                 190

His Asn Ser Tyr Thr Cys Glu Ala Thr His Lys Thr Ser Thr Ser Pro
        195                 200                 205
```

```
Ile Val Lys Ser Phe Asn Arg Asn Glu Cys
    210                 215


<210> SEQ ID NO 25
<211> LENGTH: 441
<212> TYPE: PRT
<213> ORGANISM: Artificial Sequence
<220> FEATURE:
<223> OTHER INFORMATION: Synthetic Construct

<400> SEQUENCE: 25

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ser
            20                  25                  30

Trp Ile His Trp Val Arg Gln Ala Pro Gly Lys Gly Leu Glu Trp Val
        35                  40                  45

Ala Trp Ile Ser Pro Tyr Gly Gly Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Arg His Trp Pro Gly Gly Phe Asp Tyr Trp Gly Gln Gly Thr
            100                 105                 110

Leu Val Thr Val Ser Ala Lys Thr Thr Pro Pro Ser Val Tyr Pro Leu
        115                 120                 125

Ala Pro Gly Ser Ala Ala Gln Thr Asn Ser Met Val Thr Leu Gly Cys
    130                 135                 140

Leu Val Lys Gly Tyr Phe Pro Glu Pro Val Thr Val Thr Trp Asn Ser
145                 150                 155                 160

Gly Ser Leu Ser Ser Gly Val His Thr Phe Pro Ala Val Leu Gln Ser
                165                 170                 175

Asp Leu Tyr Thr Leu Ser Ser Ser Val Thr Val Pro Ser Ser Thr Trp
            180                 185                 190

Pro Ser Gln Thr Val Thr Cys Asn Val Ala His Pro Ala Ser Ser Thr
        195                 200                 205

Lys Val Asp Lys Lys Ile Val Pro Arg Asp Cys Gly Cys Lys Pro Cys
    210                 215                 220

Ile Cys Thr Val Pro Glu Val Ser Ser Val Phe Ile Phe Pro Pro Lys
225                 230                 235                 240

Pro Lys Asp Val Leu Thr Ile Thr Leu Thr Pro Lys Val Thr Cys Val
                245                 250                 255

Val Val Ala Ile Ser Lys Asp Asp Pro Glu Val Gln Phe Ser Trp Phe
            260                 265                 270

Val Asp Asp Val Glu Val His Thr Ala Gln Thr Lys Pro Arg Glu Glu
        275                 280                 285

Gln Ile Asn Ser Thr Phe Arg Ser Val Ser Glu Leu Pro Ile Met His
    290                 295                 300

Gln Asp Trp Leu Asn Gly Lys Glu Phe Lys Cys Arg Val Asn Ser Ala
305                 310                 315                 320

Ala Phe Gly Ala Pro Ile Glu Lys Thr Ile Ser Lys Thr Lys Gly Arg
                325                 330                 335

Pro Lys Ala Pro Gln Val Tyr Thr Ile Pro Pro Pro Lys Glu Gln Met
            340                 345                 350
```

```
Ala Lys Asp Lys Val Ser Leu Thr Cys Met Ile Thr Asn Phe Phe Pro
        355                 360                 365

Glu Asp Ile Thr Val Glu Trp Gln Trp Asn Gly Gln Pro Ala Glu Asn
    370                 375                 380

Tyr Lys Asn Thr Gln Pro Ile Met Asp Thr Asp Gly Ser Tyr Phe Val
385                 390                 395                 400

Tyr Ser Lys Leu Asn Val Gln Lys Ser Asn Trp Glu Ala Gly Asn Thr
                405                 410                 415

Phe Thr Cys Ser Val Leu His Glu Gly Leu His Asn His His Thr Glu
            420                 425                 430

Lys Ser Leu Ser His Ser Pro Gly Lys
        435                 440


<210> SEQ ID NO 26
<211> LENGTH: 214
<212> TYPE: PRT
<213> ORGANISM: Artificial Sequence
<220> FEATURE:
<223> OTHER INFORMATION: Synthetic Construct

<400> SEQUENCE: 26

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Leu Tyr His Pro Ala
                85                  90                  95

Thr Phe Gly Gln Gly Thr Lys Val Glu Ile Lys Arg Ala Asp Ala Ala
            100                 105                 110

Pro Thr Val Ser Ile Phe Pro Pro Ser Ser Glu Gln Leu Thr Ser Gly
        115                 120                 125

Gly Ala Ser Val Val Cys Phe Leu Asn Asn Phe Tyr Pro Lys Asp Ile
    130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
        195                 200                 205

Phe Asn Arg Asn Glu Cys
    210


<210> SEQ ID NO 27
<211> LENGTH: 592
<212> TYPE: PRT
<213> ORGANISM: Artificial Sequence
<220> FEATURE:
<223> OTHER INFORMATION: Synthetic Construct
```

<400> SEQUENCE: 27

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Ser Gly Phe Asp Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
    210                 215                 220

Pro Pro Cys Pro Ala Pro Glu Ala Ala Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Gly Ala Pro Ile Glu Lys Thr Ile Ser Lys
                325                 330                 335

Ala Lys Gly Gln Pro Arg Glu Pro Gln Val Tyr Thr Leu Pro Pro Cys
            340                 345                 350

Arg Asp Glu Leu Thr Lys Asn Gln Val Ser Leu Trp Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415
```

```
Gln Gly Asn Val Phe Ser Cys Ser Val Met His Glu Ala Leu His Asn
            420                 425                 430

His Tyr Thr Gln Lys Ser Leu Ser Leu Ser Pro Gly Gly Gly Gly Gly
        435                 440                 445

Ser Gly Gly Gly Gly Ser Gly Gly Gly Gly Ser Ala Pro Ala Ser Ser
    450                 455                 460

Ser Thr Lys Lys Thr Gln Leu Gln Leu Glu His Leu Leu Leu Asp Leu
465                 470                 475                 480

Gln Met Ile Leu Asn Gly Ile Asn Asn Tyr Lys Asn Pro Lys Leu Thr
                485                 490                 495

Arg Met Leu Thr Ala Lys Phe Ala Met Pro Lys Lys Ala Thr Glu Leu
            500                 505                 510

Lys His Leu Gln Cys Leu Glu Glu Glu Leu Lys Pro Leu Glu Glu Val
        515                 520                 525

Leu Asn Gly Ala Gln Ser Lys Asn Phe His Leu Arg Pro Arg Asp Leu
    530                 535                 540

Ile Ser Asn Ile Asn Val Ile Val Leu Glu Leu Lys Gly Ser Glu Thr
545                 550                 555                 560

Thr Phe Met Cys Glu Tyr Ala Asp Glu Thr Ala Thr Ile Val Glu Phe
                565                 570                 575

Leu Asn Arg Trp Ile Thr Phe Ala Gln Ser Ile Ile Ser Thr Leu Thr
            580                 585                 590
```

<210> SEQ ID NO 28
<211> LENGTH: 445
<212> TYPE: PRT
<213> ORGANISM: Artificial Sequence
<220> FEATURE:
<223> OTHER INFORMATION: Synthetic Construct

<400> SEQUENCE: 28

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Ser Gly Phe Asp Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190
```

```
Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
    210                 215                 220

Pro Pro Cys Pro Ala Pro Glu Ala Ala Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Gly Ala Pro Ile Glu Lys Thr Ile Ser Lys
                325                 330                 335

Ala Lys Gly Gln Pro Arg Glu Pro Gln Val Cys Thr Leu Pro Pro Ser
            340                 345                 350

Arg Asp Glu Leu Thr Lys Asn Gln Val Ser Leu Ser Cys Ala Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Val Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
        435                 440                 445


<210> SEQ ID NO 29
<211> LENGTH: 215
<212> TYPE: PRT
<213> ORGANISM: Artificial Sequence
<220> FEATURE:
<223> OTHER INFORMATION: Synthetic Construct

<400> SEQUENCE: 29

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Leu Thr Phe Gly Gln Gly Thr Lys Val Glu Ile Lys Arg Thr Val Ala
            100                 105                 110
```

-continued

```
Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215
```

COMBINATION THERAPY OF PD-1-TARGETED IL-2 VARIANT IMMUNOCYTOKINES AND ANTIBODIES AGAINST HUMAN PD-L1

CROSS-REFERENCE TO RELATED APPLICATIONS

The present application claims priority to U.S. Provisional Patent Application Ser. No. 63/076,020, filed on Apr. 9, 2020. The content of the above-referenced application is herein expressly incorporated by reference in its entirety, including any drawings.

The present invention relates to the combination therapy of specific PD-1-targeted IL-2 variant immunocytokines with specific antibodies which bind human PD-L1.

INCORPORATION OF THE SEQUENCE LISTING

The material in the accompanying Sequence Listing is hereby incorporated by reference into this application. The accompanying Sequence Listing text file, named 050045-556001US Sequence Listing.txt, was created on Aug. 26, 2021 and is 76 KB.

BACKGROUND OF THE INVENTION

Cancer is the leading cause of death in economically developed countries and the second leading cause of death in developing countries. Despite recent advances in chemotherapy and the development of agents targeted at the molecular level to interfere with the transduction and regulation of growth signals in cancer cells, the prognosis of patients with advanced cancer remains poor in general. Consequently, there is a persisting and urgent medical need to develop new therapies that can be added to existing treatments to increase survival without causing unacceptable toxicity.

IL-2 and PD-1-Targeted IL-2-Based Immunocytokines

Interleukin 2 (IL-2) is a cytokine that activates lymphocytes and natural killer (NK) cells. IL-2 has been shown to have anti-tumor activity; however, high levels of IL-2 lead to pulmonary toxicity, and the anti-tumor activity of IL-2 is limited by a number of inhibitory feedback loops.

Based on its anti-tumor efficacy, high-dose IL-2 (aldesleukin, marketed as Proleukin®) treatment has been approved for use in patients with metastatic renal cell carcinoma (RCC) and malignant melanoma in the US, and for patients with metastatic RCC in the European Union. However, as a consequence of the mode of action of IL-2, the systemic and untargeted application of IL-2 may considerably compromise anti-tumor immunity via induction of $T_{reg}$ cells and AICD. An additional concern of systemic IL-2 treatment is related to severe side-effects upon intravenous administration, which include severe cardiovascular, pulmonary edema, hepatic, gastrointestinal (GI), neurological, and hematological events (Proleukin (aldesleukin) Summary of Product Characteristics [SmPC]: http://www.medicines.org.uk/emc/medicine/19322/SPC/ (accessed May 27, 2013)). Low-dose IL-2 regimens have been tested in patients, although at the expense of suboptimal therapeutic results. Taken together, therapeutic approaches utilizing IL-2 may be useful for cancer therapy if the liabilities associated with its application can be overcome. Immunoconjugates comprising a PD-1-targeted antigen binding moiety and an IL-2-based effector moiety are described in e.g. WO 2018/184964 A1.

PD-1 and PD-1 Antibodies

Programmed cell death protein 1 (PD-1 or CD279) is an inhibitory member of the CD28 family of receptors, that also includes CD28, CTLA-4, ICOS and BTLA. PD-1 is a cell surface receptor and is expressed on activated B cells, T cells, and myeloid cells (Okazaki et al (2002) Curr. Opin. Immunol. 14: 391779-82; Bennett et al. (2003) J Immunol 170:711-8). The structure of PD-1 is a monomeric type 1 transmembrane protein, consisting of one immunoglobulin variable-like extracellular domain and a cytoplasmic domain containing an immunoreceptor tyrosine-based inhibitory motif (ITIM) and an immunoreceptor tyrosine-based switch motif (ITSM). Two ligands for PD-1 have been identified, PD-L1 and PD-L2, that have been shown to downregulate T cell activation upon binding to PD-1 (Freeman et al (2000) J Exp Med 192: 1027-34; Latchman et al (2001) Nat Immunol 2:261-8; Carter et al (2002) Eur J Immunol 32:634-43). Both PD-L1 and PD-L2 are B7 homologs that bind to PD-1, but do not bind to other CD28 family members. One ligand for PD-1, PD-L1 is abundant in a variety of human cancers (Dong et al (2002) Nat. Med 8:787-9). The interaction between PD-1 and PD-L1 results in a decrease in tumor infiltrating lymphocytes, a decrease in T-cell receptor mediated proliferation, and immune evasion by the cancerous cells (Dong et al. (2003) J. MoI. Med. 81:281-7; Blank et al. (2005) Cancer Immunol. Immunother. 54:307-314; Konishi et al. (2004) Clin. Cancer Res. 10:5094-100). Immune suppression can be reversed by inhibiting the local interaction of PD-1 with PD-L1, and the effect is additive when the interaction of PD-1 with PD-L2 is blocked as well (Iwai et al. (2002) Proc. Nat 7. Acad. ScL USA 99: 12293-7; Brown et al. (2003) J. Immunol. 170: 1257-66). Antibodies that bind to PD-1 are described in e.g. WO 2017/055443 A1.

PD-L1 and PD-L1 Antibodies

Co-stimulation or the provision of two distinct signals to T-cells is a widely accepted model of lymphocyte activation of resting T lymphocytes by antigen-presenting cells (APCs). Lafferty et al., *Aust. J. Exp. Biol. Med. Sci.* 53: 27-42 (1975).

This model further provides for the discrimination of self from non-self and immune tolerance. Bretscher et al., *Science* 169: 1042-1049 (1970); Bretscher, P. A., *P.N.A.S USA* 96: 185-190 (1999); Jenkins et al., *J. Exp. Med.* 165: 302-319 (1987). The primary signal, or antigen specific signal, is transduced through the T-cell receptor (TCR) following recognition of foreign antigen peptide presented in the context of the major histocompatibility-complex (MHC). The second or co-stimulatory signal is delivered to T-cells by co-stimulatory molecules expressed on antigen-presenting cells (APCs), and induce T-cells to promote clonal expansion, cytokine secretion and effector function. Lenschow et al., *Ann. Rev. Immunol.* 14:233 (1996). In the absence of co-stimulation, T-cells can become refractory to antigen stimulation, do not mount an effective immune response, and further may result in exhaustion or tolerance to foreign antigens.

The simple two-signal model can be an oversimplification because the strength of the TCR signal actually has a quantitative influence on T-cell activation and differentiation. Viola et al., *Science* 273: 104-106 (1996); Sloan-Lancaster, *Nature* 363: 156-159 (1993). Moreover, T-cell activation can occur even in the absence of co-stimulatory signal if the TCR signal strength is high. More importantly, T-cells receive both positive and negative secondary co-stimulatory signals. The regulation of such positive and negative signals is critical to maximize the host's protective immune responses, while maintaining immune tolerance and preventing autoimmunity.

Negative secondary signals seem necessary for induction of T-cell tolerance, while positive signals promote T-cell activation. While the simple two-signal model still provides a valid explanation for naive lymphocytes, a host's immune response is a dynamic process, and co-stimulatory signals can also be provided to antigen-exposed T-cells.

The mechanism of co-stimulation is of therapeutic interest because the manipulation of co-stimulatory signals has shown to provide a means to either enhance or terminate cell-based immune response. Recently, it has been discovered that T cell dysfunction or anergy occurs concurrently with an induced and sustained expression of the inhibitory receptor, programmed death 1 polypeptide (PD-1). As a result, therapeutic targeting PD-1 and other molecules which signal through interactions with PD-1, such as programmed death ligand 1 (PD-L1) and programmed death ligand 2 (PD-L2) are an area of intense interest. The inhibition of PD-L1 signaling has been proposed as a means to enhance T cell immunity for the treatment of cancer (e.g., tumor immunity) and infection, including both acute and chronic (e.g., persistent) infection. However, as an optimal therapeutic directed to a target in this pathway has yet to be commercialized, a significant unmet medical need exists. Antibodies against PD-L1 are described e.g. in WO 2010/077634.

SUMMARY OF THE INVENTION

The invention comprises the combination therapy of a PD-1-targeted IL-2 variant immunocytokine with an antibody which binds to human PD-L1 for use in the treatment of cancer or tumor, for use in the prevention or treatment of metastasis, or for use in stimulating an immune response or function, such as T cell activity.

The invention comprises the use of a PD-1 or T cells-targeted IL-2 variant immunocytokine for the manufacture of a medicament for use in the treatment of cancer or tumor, for use in the prevention or treatment of metastasis, or for use in stimulating an immune response or function, such as T cell activity, wherein the PD-1-targeted IL-2 variant immunocytokine is administered in combination with an antibody which binds to human PD-L1.

The invention comprises the use of an antibody which binds to human PD-L1 for the manufacture of a medicament for use in the treatment of cancer or tumor, for use in the prevention or treatment of metastasis, or for use in stimulating an immune response or function, such as T cell activity, wherein the antibody which binds to human PD-L1 is administered in combination with a PD-1-targeted IL-2 variant immunocytokine.

The invention comprises a method of treatment of cancer or tumor, a method of prevention or treatment of metastasis, or a method of stimulating an immune response or function, such as T cell activity, the method comprising administering the combination therapy of a PD-1-targeted IL-2 variant immunocytokine with an antibody which binds to human PD-L1.

The PD-1-targeted IL-2 variant immunocytokine used in the combination therapy is characterized in comprising a) a heavy chain variable domain VH of SEQ ID NO:5 and a light chain variable domain VL of SEQ ID NO:6, and the polypeptide sequence of SEQ ID NO:2, or b) a polypeptide sequence of SEQ ID NO:7 or SEQ ID NO:8 or SEQ ID NO:9, or c) the polypeptide sequences of SEQ ID NO:7, and SEQ ID NO:8 and SEQ ID NO:9, or d) the polypeptide sequences of SEQ ID NO:12, and SEQ ID NO:13 and SEQ ID NO:14; and the antibody which binds to human PD-L1 used in the combination therapy is characterized in comprising a) a heavy chain variable domain VH of SEQ ID NO:15 and a light chain variable domain VL of SEQ ID NO:16, or b) a heavy chain variable domain VH of SEQ ID NO:19 and a light chain variable domain VL of SEQ ID NO:20.

In embodiments of the invention, a combination therapy of a PD-1-targeted IL-2 variant immunocytokine with an antibody which binds to human PD-L1 as described herein is for use in the treatment of cancer. PD-1 may be presented in a tumor cell environment. The cancer may be selected from the groups consisting of breast cancer, lung cancer, colon cancer, ovarian cancer, melanoma cancer, bladder cancer, renal cancer, kidney cancer, liver cancer, head and neck cancer, colorectal cancer, melanoma, pancreatic cancer, gastric carcinoma cancer, esophageal cancer, mesothelioma, prostate cancer, leukemia, lymphomas, myelomas.

In an embodiment of the invention, a combination therapy of a PD-1-targeted IL-2 variant immunocytokine with an antibody which binds to human PD-L1 as described herein is for use in the prevention or treatment of metastasis.

In an embodiment of the invention, a combination therapy of a PD-1-targeted IL-2 variant immunocytokine with an antibody which binds to human PD-L1 as described herein is for use in treating or delaying progression of an immune related disease such as tumor immunity.

In an embodiment of the invention, a combination therapy of a PD-1-targeted IL-2 variant immunocytokine with an antibody which binds to human PD-L1 as described herein is for use in stimulating an immune response or function, such as T cell activity.

The invention comprises a PD-1-targeted IL-2 variant immunocytokine, wherein the immunocytokine is administered in combination with an antibody which binds to human PD-L1 as described herein for use in

- i) inhibition of tumor growth in a tumor; and/or
- ii) enhancing median and/or overall survival of subjects with a tumor;

wherein PD-1 is presented on immune cells, particularly T cells, in a tumor cell environment, wherein the PD-1-targeted IL-2 variant immunocytokine used in the combination therapy is characterized in comprising a) a heavy chain variable domain VH of SEQ ID NO:5 and a light chain variable domain VL of SEQ ID NO:6, and the polypeptide sequence of SEQ ID NO:2, or b) a polypeptide sequence of SEQ ID NO:7 or SEQ ID NO:8 or SEQ ID NO:9, or c) the polypeptide sequences of SEQ ID NO:7, and SEQ ID NO:8 and SEQ ID NO:9, or d) the polypeptide sequences of SEQ ID NO:12, and SEQ ID NO:13 and SEQ ID NO:14;

and the antibody which binds to human PD-L1 used in the combination therapy is characterized in comprising a) a heavy chain variable domain VH of SEQ ID NO:15 and a light chain variable domain VL of SEQ ID NO:16, or b) a heavy chain variable domain VH of SEQ ID NO:19 and a light chain variable domain VL of SEQ ID NO:20.

The invention may comprise a PD-1-targeted IL-2 variant immunocytokine, wherein the immunocytokine is administered in combination with an antibody which binds to human PD-L1 as described herein, wherein the PD-1-targeted IL-2 variant immunocytokine used in the combination therapy is characterized in comprising the polypeptide sequences of SEQ ID NO:7, SEQ ID NO:8 and SEQ ID NO:9, and wherein the antibody which binds to human PD-L1 used in the combination therapy is characterized in comprising a heavy chain variable domain VH of SEQ ID NO:15 and a light chain variable domain VL of SEQ ID NO:16.

The invention preferably comprises a PD-1-targeted IL-2 variant immunocytokine, wherein the immunocytokine is administered in combination with an antibody which binds to human PD-L1, wherein the PD-1-targeted IL-2 variant immunocytokine used in the combination therapy is characterized in comprising the polypeptide sequences of SEQ ID NO:7, SEQ ID NO:8 and SEQ ID NO:9; and wherein the antibody which binds to human PD-L1 used in the combination therapy is Atezolizumab.

The antibody component of the immunocytokine and the antibody may be of human IgG1 subclass or human IgG4 subclass. The antibody may have reduced or minimal effector function. The minimal effector function may results from an effector less Fc mutation. The effector less Fc mutation may be L234A/L235A or L234A/L235A/P329G or N297A or D265A/N297A.

In a further aspect of the invention, the PD-1-targeted IL-2 variant immunocytokine is administered to a patient in combination with an antibody which binds to human PD-L1 as described herein, wherein the patient is treated or was pre-treated with immunotherapy. Said immunotherapy may comprise adoptive cell transfer, administration of monoclonal antibodies, administration of cytokines, administration of a cancer vaccine, T cell engaging therapies, or any combination thereof. The adoptive cell transfer may comprise administering chimeric antigen receptor expressing T-cells (CAR T-cells), T-cell receptor (TCR) modified T-cells, tumor-infiltrating lymphocytes (TIL), chimeric antigen receptor (CAR)-modified natural killer cells, T cell receptor (TCR) transduced cells, or dendritic cells, or any combination thereof.

The invention further comprises:

A) a method for i) inhibition of tumor growth;

ii) enhancing median and/or overall survival of subjects with a tumor;

wherein PD-1 is presented on immune cells, particularly T cells, wherein a PD-1-targeted IL-2 variant immunocytokine is administered in combination with an antibody which binds to human PD-L1, or B) a method of treatment of a patient having a tumor, wherein PD-1 is expressed in the tumor cell environment, and wherein a PD-1-targeted IL-2 variant immunocytokine is administered in combination with an antibody which binds to human PD-L1, wherein the PD-1-targeted IL-2 variant immunocytokine used in the combination therapy is characterized in comprising a) a heavy chain variable domain VH of SEQ ID NO:5 and a light chain variable domain VL of SEQ ID NO:6, and the polypeptide sequence of SEQ ID NO:2, or b) a polypeptide sequence of SEQ ID NO:7 or SEQ ID NO:8 or SEQ ID NO:9, or c) the polypeptide sequences of SEQ ID NO:7, and SEQ ID NO:8 and SEQ ID NO:9, or d) the polypeptide sequences of SEQ ID NO:12, and SEQ ID NO:13 and SEQ ID NO:14, and the antibody which binds to human PD-L1 used in the combination therapy is characterized in comprising a) a heavy chain variable domain VH of SEQ ID NO:15 and a light chain variable domain VL of SEQ ID NO:16, or b) a heavy chain variable domain VH of SEQ ID NO:19 and a light chain variable domain VL of SEQ ID NO:20.

The combination therapies of the PD-1-targeted IL-2 variant immunocytokines and antibodies described herein show benefits for patients in need of a therapy targeting an antigen presented on a tumor cell or in a tumor cell environment. The combination therapies of the PD-1-targeted IL-2 variant immunocytokines and antibodies described herein show benefits for patients in need of a PD-1-targeting therapy. The PD-1-targeted IL-2 variant immunocytokines according to the invention show efficacy in enhancing median and/or overall survival of subjects with a target-expressing tumor and are especially useful inter alia in the treatment of cancer and metastasis in combination with the anti-PD-L1 antibodies described herein. The specific PD-1-targeted IL-2 variant immunocytokines according to the invention show efficacy in tumor growth inhibitory activity against tumors, wherein PD-1 is expressed in a tumor cell environment, and are especially useful inter alia in the treatment of cancer and metastasis in combination with the specific anti-PD-L1 antibodies described herein. The specific antibodies which bind to human PD-L1, particularly atezolizumab, according to the invention show efficacy in enhancing median and/or overall survival of subjects with tumor, wherein PD-1 is expressed in the tumor cell environment, and are especially useful inter alia in the treatment of cancer and metastasis in combination with the specific PD-1-targeted IL-2 variant immunocytokines described herein.

In an embodiment of the invention, provided is the PD-1-targeted IL-2 variant immunocytokine in combination with an antibody which binds to human PD-L1 as described herein, for use as a combination therapy in the prevention or treatment of metastasis, or for use as a combination therapy in stimulating an immune response or function, such as T cell activity, wherein the patient is treated with or was pre-treated with immunotherapy. Said immunotherapy may comprise adoptive cell transfer, administration of monoclonal antibodies, administration of cytokines, administration of a cancer vaccine, T cell engaging therapies, or any combination thereof. The adoptive cell transfer may comprise administering chimeric antigen receptor expressing T-cells (CAR T-cells), T-cell receptor (TCR) modified T-cells, tumor-infiltrating lymphocytes (TIL), chimeric antigen receptor (CAR)-modified natural killer cells, T cell receptor (TCR) transduced cells, or dendritic cells, or any combination thereof.

BRIEF DESCRIPTION OF THE FIGURES

The patent application file contains at least one drawing executed in color. Copies of this patent or patent application publication with color drawing(s) will be provided by the Office upon request and payment of the necessary fee.

FIG. 2A presents the frequency of CD8+ T cells in the spleen determined by flow cytometry. FIG. 2B presents the frequency of TAG antigen-specific CD8+ T cells in the spleen shown as percentage of total CD8+ T cells. FIG. 2C presents IHC of PanNET tumors stained with the indicated antibodies (n=3-5; scale bar=200 μm).

FIG. 3A-E. Presents an increased therapeutic efficacy upon combination of PD1-IL2v with anti-PD-L1. Tumor bearing RipTag5 mice were subjected to drug treatments and the tumor progression was monitored by ultrasound imaging. FIG. 3A presents tumor growth curve of untreated mice (n=3). FIG. 3B presents tumor growth curves of RipTag5 mice treated with PD1-IL2v (n=6). FIG. 3C presents IHC of untreated and PD1-IL2v relapsed tumors stained with the indicated antibodies (n=3; scale bar=50 μm). FIG. 3D presents tumor growth curves of mice treated with anti-PDL1 (n=4). FIG. 3E presents tumor growth curves of RipTag5 mice treated with PD1-IL2v and anti-PDL1 (n=7).

FIG. 4A presents response rate represented as survival graph. Two mice in the PD-IL2v and one mouse in the PD1-IL2v+anti-PD-L1 treatment group developed severe hyperglycemia due to the complete response and had to be euthanized. These mice were still considered as complete responders in the graph. FIG. 4B presents ultrasound images of tumors upon 0 and 2 weeks of PD1-IL2v and PD1-IL2v+anti-PD-L1 treatment. Statistical analysis: Log-rank Mantel-Cox test, *p<0.02. Number of mice: anti-PD-L1 n=4, PD1-IL2v n=10, PD1-IL2v+anti-PD-L1 n=7.

DETAILED DESCRIPTION OF THE INVENTION

IL-2 Pathway

Figure 1:
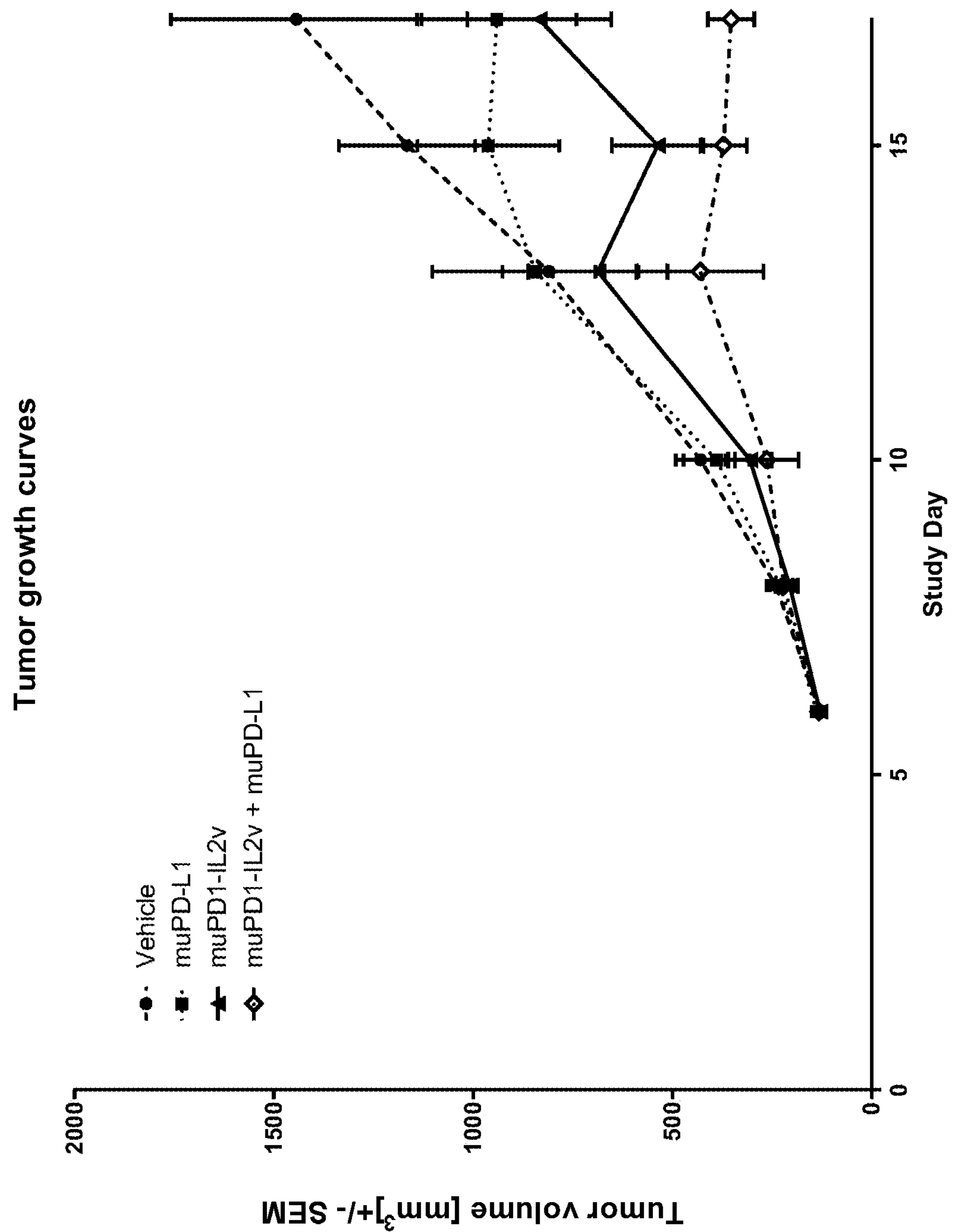
FIG. 1. Presents the results of an efficacy experiment with muPD1-IL2v and muPD-L1 Mab as single agents and in a combination setting. The MC38 colorectal carcinoma cell line was injected subcutaneously in Black 6 mice to study tumor growth inhibition in a subcutaneous model. Tumor size was measured using a caliper. Therapy started when tumors reached 150 $mm^3$. The amount of antibodies injected per mouse was 0.5 mg/kg for muPD1-IL2v qw and 10 mg/kg for muPD-L1 for the first administration followed by 5 mg/kg 2qw after that. The treatment lasted 2 weeks. In the combination group the antibodies were administered concomitantly. The combination muPD-IL2v+muPD-L1 Mab mediated superior efficacy in terms of tumor growth inhibition compared to vehicle, muPD1-IL2v and muPD-L1 Mab single agent groups.

The ability of IL-2 to expand and activate lymphocyte and NK cell populations both in vitro and in vivo explains the anti-tumor effects of IL-2. However, as a regulatory mechanism to prevent excessive immune responses and potential autoimmunity, IL-2 leads to activation-induced cell death (AICD) and renders activated T-cells susceptible to Fas-mediated apoptosis.

Moreover, IL-2 is involved in the maintenance and expansion of peripheral $CD4^{+}CD25^{+}$ $T_{reg}$ cells (Fontenot J D, Rasmussen J P, Gavin M A, et al. A function for interleukin 2 in Foxp3 expressing regulatory T cells. Nat Immunol. 2005; 6:1142-1151; D'Cruz L M, Klein L. Development and function of agonist-induced CD25+Foxp3+ regulatory T cells in the absence of interleukin 2 signaling. Nat Immunol. 2005; 6:1152 1159; Maloy K J, Powrie F. Fueling regulation: IL-2 keeps CD4+ $T_{reg}$ cells fit. Nat Immunol. 2005; 6:1071-1072). These cells suppress effector T-cells from destroying self or target, either through cell-cell contact or through release of immunosuppressive cytokines, such as IL-10 or transforming growth factor (TGF)-β. Depletion of $T_{reg}$ cells was shown to enhance IL-2-induced anti-tumor immunity (Imai H, Saio M, Nonaka K, et al. Depletion of CD4+CD25+ regulatory T cells enhances interleukin-2-induced antitumor immunity in a mouse model of colon adenocarcinoma. Cancer Sci. 2007; 98:416-423).

IL-2 also plays a significant role in memory CD8+ T-cell differentiation during primary and secondary expansion of CD8+ T cells. IL-2 seems to be responsible for optimal expansion and generation of effector functions following primary antigenic challenge. During the contraction phase of an immune response where most antigen-specific CD8+ T cells disappear by apoptosis, IL-2 signals are able to rescue CD8+ T cells from cell death and provide a durable increase in memory CD8+ T-cells. At the memory stage, CD8+ T-cell frequencies can be boosted by administration of exogenous IL-2. Moreover, only CD8+ T cells that have received IL-2 signals during initial priming are able to mediate efficient secondary expansion following renewed antigenic challenge. Thus, IL-2 signals during different phases of an immune response are key in optimizing CD8+ T-cell functions, thereby affecting both primary and secondary responses of these T cells (Adv Exp Med Biol. 2010; 684:28-41. The role of interleukin-2 in memory CD8 cell differentiation. Boyman Ol, Cho J H, Sprent J).

Based on its anti-tumor efficacy, high-dose IL-2 (aldesleukin, marketed as Proleukin®) treatment has been approved for use in patients with metastatic renal cell carcinoma (RCC) and malignant melanoma in the US, and for patients with metastatic RCC in the European Union. However, as a consequence of the mode of action of IL-2, the systemic and untargeted application of IL-2 may considerably compromise anti-tumor immunity via induction of $T_{reg}$ cells and AICD. An additional concern of systemic IL-2 treatment is related to severe side-effects upon intravenous administration, which include severe cardiovascular, pulmonary edema, hepatic, gastrointestinal (GI), neurological, and hematological events (Proleukin (aldesleukin) Summary of Product Characteristics [SmPC]: http://www.medicines.org.uk/emc/medicine/19322/SPC/ (accessed May 27, 2013)). Low-dose IL-2 regimens have been tested in patients, although at the expense of suboptimal therapeutic results. Taken together, therapeutic approaches utilizing IL-2 may be useful for cancer therapy if the liabilities associated with its application can be overcome.

Immunoconjugates comprising a PD-1-targeted antigen binding moiety and an IL-2-based effector moiety, for example including a mutant IL-2, are described in e.g. WO 2018/184964.

In particular, mutant IL-2 (e.g., a quadruple mutant known as IL-2 qm) has been designed to overcome the limitations of wildtype IL-2 (e.g., aldesleukin) or first generation IL-2-based immunocytokines by eliminating the binding to the IL-2Ra subunit (CD25). This mutant IL-2 qm has been coupled to various tumor-targeting antibodies such as a humanized antibody directed against CEA and an antibody directed against FAP, described in WO 2012/146628 and WO 2012/107417. In addition, the Fc region of the antibody has been modified to prevent binding to Fcγ receptors and the C1q complex. The resulting tumor-targeted IL-2 variant immunocytokines (e.g., CEA-targeted IL-2 variant immunocytokine and FAP-targeted IL-2 variant immunocytokine) have been shown in nonclinical in vitro and in vivo experiments to be able to eliminate tumor cells.

Thus the resulting immunocytokines represent a class of targeted IL-2 variant immunocytokines that address the liabilities of IL-2 by eliminating the binding to the IL-2Ra subunit (CD25):

Properties of Wildtype IL-2 and the IL-2 Variant

| | IL-2 | IL2v with Eliminated CD25 Binding |
|---|---|---|
| Advantage | Activation of IL-2Rβγ heterodimer and IL-2Rαβγ on effector cells | Activation of IL-2Rβγ heterodimer on effector cells<br>Reduced sensitivity to Fas-mediated induction of apoptosis (also termed AICD)<br>No preferential $T_{reg}$ cells stimulation<br>No binding to CD25 on lung endothelium<br>Superior pharmacokinetics and targeting (lack of CD25 sink) |
| Disadvantage | Vascular leak (binding to CD25 lung endothelium)<br>AICD<br>Preferential stimulation of $T_{reg}$ cells | |

The term "IL-2" or "human IL-2" refers to the human IL-2 protein including wildtype and variants comprising one or more mutations in the amino acid sequence of wildtype IL-2, for example as shown in SEQ ID NO:2 having a C125A substitution to avoid the formation of disulphide-bridged IL-2 dimers. IL-2 may also be mutated to remove N- and/or O-glycosylation sites.

PD-1/PD-L1/PD-L2 Pathway

An important negative co-stimulatory signal regulating T cell activation is provided by programmed death −1 receptor (PD-1)(CD279), and its ligand binding partners PD-L1 (B7-H1, CD274; SEQ ID NO: 88) and PD-L2 (B7-DC, CD273). The negative regulatory role of PD-1 was revealed by PD-1 knock outs (Pdcd1−/−), which are prone to autoimmunity. Nishimura et al., Immunity 11: 141-51 (1999); Nishimura et al., Science 291: 319-22 (2001). PD-1 is related to CD28 and CTLA-4, but lacks the membrane proximal cysteine that allows homodimerization. The cytoplasmic domain of PD-1 contains an immunoreceptor tyrosine-based inhibition motif (ITIM, V/IxYxxL/V). PD-1 only binds to PD-L1 and PD-L2. Freeman et al., J. Exp. Med. 192: 1-9 (2000); Dong et al., Nature Med. 5: 1365-1369 (1999); Latchman et al., Nature Immunol. 2: 261-268 (2001); Tseng et al., J. Exp. Med. 193: 839-846 (2001).

PD-1 can be expressed on T cells, B cells, natural killer T cells, activated monocytes and dendritic cells (DCs). PD-1 is expressed by activated, but not by unstimulated human CD4+ and CD8+ T cells, B cells and myeloid cells. This stands in contrast to the more restricted expression of CD28 and CTLA-4. Nishimura et al., Int. Immunol. 8: 773-80 (1996); Boettler et al., J. Virol. 80: 3532-40 (2006). There are at least 4 variants of PD-1 that have been cloned from activated human T cells, including transcripts lacking (i) exon 2, (ii) exon 3, (iii) exons 2 and 3 or (iv) exons 2 through 4. Nielsen et al., Cell. Immunol. 235: 109-16 (2005). With the exception of PD-1 Δex3, all variants are expressed at similar levels as full length PD-1 in resting peripheral blood mononuclear cells (PBMCs). Expression of all variants is significantly induced upon activation of human T cells with anti-CD3 and anti-CD28. The PD-1 Δex3 variants lacks a transmembrane domain, and resembles soluble CTLA-4, which plays an important role in autoimmunity. Ueda et al., Nature 423: 506-11 (2003). This variant is enriched in the synovial fluid and sera of patients with rheumatoid arthritis. Wan et al., J. Immunol. 177: 8844-50 (2006).

The two PD-1 ligands differ in their expression patterns. PD-L1 is constitutively expressed on mouse T and B cells, CDs, macrophages, mesenchymal stem cells and bone marrow-derived mast cells. Yamazaki et al., J. Immunol. 169: 5538-45 (2002). PD-L1 is expressed on a wide range of nonhematopoietic cells (e.g., cornea, lung, vascular epithelium, liver nonparenchymal cells, mesenchymal stem cells, pancreatic islets, placental synctiotrophoblasts, keratinocytes, etc.) [Keir et al., Annu. Rev. Immunol. 26: 677-704 (2008)], and is unregulated on a number of cell types after activation. Both type I and type II interferons IFN's) upregulate PD-L1. Eppihimer et al., Microcirculation 9: 133-45 (2002); Schreiner et al., J. Neuroimmunol. 155: 172-82 (2004). PD-L1 expression in cell lines is decreased when MyD88, TRAF6 and MEK are inhibited. Liu et al., Blood 110: 296-304 (2007). JAK2 has also been implicated in PD-L1 induction. Lee et al., FEBS Lett. 580: 755-62 (2006); Liu et al., Blood 110: 296-304 (2007). Loss or inhibition of phosphatase and tensin homolog (PTEN), a cellular phosphatase that modified phosphatidylinositol 3-kinase (PI3K) and Akt signaling, increased post-transcriptional PD-L1 expression in cancers. Parsa et al., Nat. Med. 13: 84-88 (2007).

PD-L2 expression is more restricted than PD-L1. PD-L2 is inducibly expressed on DCs, macrophages, and bone marrow-derived mast cells. PD-L2 is also expressed on about half to two-thirds of resting peritoneal B1 cells, but not on conventional B2 B cells. Zhong et al., Eur. J. Immunol. 37: 2405-10 (2007). PD-L2+ B1 cells bind phosphatidylcholine and may be important for innate immune responses against bacterial antigens. Induction of PD-L2 by IFN-gamma is partially dependent upon NF-κB. Liang et al., Eur. J. Immunol. 33: 2706-16 (2003). PD-L2 can also be induced on monocytes and macrophages by GM-CF, IL-4 and IFN-gamma. Yamazaki et al., J. Immunol. 169: 5538-45 (2002); Loke et al., PNAS 100:5336-41 (2003).

PD-1 signaling typically has a greater effect on cytokine production than on cellular proliferation, with significant effects on IFN-gamma, TNF-alpha and IL-2 production. PD-1 mediated inhibitory signaling also depends on the strength of the TCR signaling, with greater inhibition delivered at low levels of TCR stimulation. This reduction can be overcome by costimulation through CD28 [Freeman et al., J. Exp. Med. 192: 1027-34 (2000)] or the presence of IL-2 [Carter et al., Eur. J. Immunol. 32: 634-43 (2002)].

Evidence is mounting that signaling through PD-L1 and PD-L2 may be bidirectional. That is, in addition to modifying TCR or BCR signaling, signaling may also be delivered back to the cells expressing PD-L1 and PD-L2. While treatment of dendritic cells with a naturally human anti-PD-L2 antibody isolated from a patient with Waldenstrom's macroglobulinemia was not found to upregulate MHC II or B7 costimulatory molecules, such cells did produce greater amount of proinflammatory cytokines, particularly TNF-alpha and IL-6, and stimulated T cell proliferation. Nguyen et al., J. Exp. Med. 196: 1393-98 (2002). Treatment of mice with this antibody also (1) enhanced resistance to transplanted b16 melanoma and rapidly induced tumor-specific CTL. Radhakrishnan et al., J. Immunol. 170: 1830-38 (2003); Radhakrishnan et al., Cancer Res. 64: 4965-72 (2004); Heckman et al., Eur. J. Immunol. 37: 1827-35 (2007); (2) blocked development of airway inflammatory disease in a mouse model of allergic asthma. Radhakrishnan et al., J. Immunol. 173: 1360-65 (2004); Radhakrishnan et al., J. Allergy Clin. Immunol. 116: 668-74 (2005).

Further evidence of reverse signaling into dendritic cells ("DC's") results from studies of bone marrow derived DC's cultured with soluble PD-1 (PD-1 EC domain fused to Ig constant region—"s-PD-1"). Kuipers et al., Eur. J. Immunol. 36: 2472-82 (2006). This sPD-1 inhibited DC activation and increased IL-10 production, in a manner reversible through administration of anti-PD-1.

Additionally, several studies show a receptor for PD-L1 or PD-L2 that is independent of PD-1. B7.1 has already been identified as a binding partner for PD-L1. Butte et al., Immunity 27: 111-22 (2007). Chemical crosslinking studies suggest that PD-L1 and B7.1 can interact through their IgV-like domains. B7.1:PD-L1 interactions can induce an inhibitory signal into T cells. Ligation of PD-L1 on CD4+ T cells by B7.1 or ligation of B7.1 on CD4+ T cells by PD-L1 delivers an inhibitory signal. T cells lacking CD28 and CTLA-4 show decreased proliferation and cytokine production when stimulated by anti-CD3 plus B7.1 coated beads. In T cells lacking all the receptors for B7.1 (i.e., CD28, CTLA-4 and PD-L1), T cell proliferation and cytokine production were no longer inhibited by anti-CD3 plus B7.1 coated beads. This indicates that B7.1 acts specifically through PD-L1 on the T-cell in the absence of CD28 and CTLA-4. Similarly, T cells lacking PD-1 showed decreased proliferation and cytokine production when stimulated in the presence of anti-CD3 plus PD-L1 coated beads, demonstrating the inhibitory effect of PD-L1 ligation on B7.1 on T cells. When T cells lacking all known receptors for PD-L1 (i.e., no PD-1 and B7.1), T cell proliferation was no longer impaired by anti-CD3 plus PD-L1 coated beads. Thus, PD-L1 can exert an inhibitory effect on T cells either through B7.1 or PD-1.

The direct interaction between B7.1 and PD-L1 suggests that the current understanding of costimulation is incomplete, and underscores the significance to the expression of these molecules on T cells. Studies of PD-L1−/− T cells indicate that PD-L1 on T cells can downregulate T cell cytokine production. Latchman et al., Proc. Natl. Acad. Sci. USA 101: 10691-96 (2004). Because both PD-L1 and B7.1 are expressed on T cells, B cells, DCs and macrophages, there is the potential for directional interactions between B7.1 and PD-L1 on these cells types. Additionally, PD-L1 on non-hematopoietic cells may interact with B7.1 as well as PD-1 on T cells, raising the question of whether PD-L1 is involved in their regulation. One possible explanation for the inhibitory effect of B7.1:PD-L1 interaction is that T cell PD-L1 may trap or segregate away APC B7.1 from interaction with CD28.

As a result, the antagonism of signaling through PD-L1, including blocking PD-L1 from interacting with either PD-1, B7.1 or both, thereby preventing PD-L1 from sending a negative co-stimulatory signal to T-cells and other antigen presenting cells is likely to enhance immunity in response to infection (e.g., acute and chronic) and tumor immunity. In addition, the anti-PD-L1 antibodies of the present invention, may be combined with antagonists of other components of PD-1:PD-L1 signaling, for example, antagonist anti-PD-1 and anti-PD-L2 antibodies.

The term "human PD-L1" refers to the human protein PD-L1 (SEQ ID NO:4, PD-1 signaling typically). As used herein, "binding to human PD-L1" or "specifically binding to human PD-L1" or "which binds to human PD-L1" or "anti-PD-L1 antibody" refers to an antibody specifically binding to the human PD-L1 antigen with a binding affinity of KD-value of $1.0\times10^{-8}$ mol/l or lower, in one embodiment of a KD-value of $1.0\times10^{-9}$ mol/l or lower. The binding affinity is determined with a standard binding assay, such as surface plasmon resonance technique (BIAcore®, GE-Healthcare Uppsala, Sweden). Thus an "antibody binding to human PD-L1" as used herein refers to an antibody specifically binding to the human PD-L1 antigen with a binding affinity of KD $1.0\times10^{-8}$ mol/l or lower (in one embodiment $1.0\times10^{-8}$ mol/l-$1.0\times10^{-13}$ mol/l), in on embodiment of a KD $1.0\times10^{-9}$ mol/l or lower (in one embodiment $1.0\times10^{-9}$ mol/l-$1.0\times10^{-13}$ mol/l).

In particular, the inventors have discovered that PD-1-targeted mutant IL-2 provides superior therapeutic effects in vivo when used in combination with an antibody which binds to human PD-L1.

The ability of IL-2 to expand and activate lymphocytes and natural killer (NK) cells underlies the anti-tumor activity of IL-2. IL-2 mutants designed to eliminate the binding of IL-2 to IL-2α subunit (CD25) overcome the limitations of IL-2 and as part of a tumor-targeted IL-2 variant immunocytokine, such as a CEA-targeted IL-2 variant immunocytokine or a FAP-targeted IL-2 variant immunocytokine, have been shown to be able to eliminate tumor cells.

Immunocytokines and Antibodies

The PD-1-targeted IL-2 variant immunocytokine used in the combination therapy described herein comprises

- an antibody which binds to PD-1 on PD-1 expressing immune cells, particularly T cells, or in a tumor cell environment, or an antigen binding fragment thereof, and
- an IL-2 mutant, particularly a mutant of human IL-2, having reduced binding affinity to the α-subunit of the IL-2 receptor (as compared to wild-type IL-2, e.g. human IL-2 shown as SEQ ID NO: 2), such as an IL-2 comprising:
  - i) one, two or three amino acid substitution(s) at one, two or three position(s) selected from the positions corresponding to residues 42, 45 and 72 of human IL-2 shown as SEQ ID NO:2, for example three substitutions at three positions, for example the specific amino acid substitutions F42A, Y45A and L72G; or
  - ii) the features as set out in i) plus an amino acid substitution at a position corresponding to residue 3 of human IL-2 shown as SEQ ID NO:2, for example the specific amino acid substitution T3A; or
  - iii) four amino acid substitutions at positions corresponding to residues 3, 42, 45 and 72 of human IL-2 shown as SEQ ID NO:2, for example the specific amino acid substitutions T3A, F42A, Y45A and L72G.

The PD-1-targeted IL-2 variant immunocytokine used in the combination therapy described herein may comprise

- a heavy chain variable domain and a light chain variable domain of an antibody which binds to PD-1 presented on immune cells, particularly T cells, or in a tumor cell environment and an Fc domain consisting of two subunits and comprising a modification promoting heterodimerization of two non-identical polypeptide chains, and
- an IL-2 mutant, particularly a mutant of human IL-2, having reduced binding affinity to the α-subunit of the IL-2 receptor (as compared to wild-type IL-2, e.g. human IL-2 shown as SEQ ID NO: 2), such as an IL-2 comprising:
  - i) one, two or three amino acid substitution(s) at one, two or three position(s) selected from the positions corresponding to residues 42, 45 and 72 of human IL-2 shown as SEQ ID NO:2, for example three substitutions at three positions, for example the specific amino acid substitutions F42A, Y45A and L72G; or ii) the features as set out in i) plus an amino acid substitution at a position corresponding to residue 3 of human IL-2 shown as SEQ ID NO:2, for example the specific amino acid substitution T3A; or iii) four amino acid substitutions at positions corresponding to residues 3, 42, 45 and 72 of human IL-2 shown as SEQ ID NO:2, for example the specific amino acid substitutions T3A, F42A, Y45A and L72G.

A PD-1-targeted IL-2 variant immunocytokine used in the combination therapy may comprise a) a heavy chain variable domain VH of SEQ ID NO:5 and a light chain variable domain VL of SEQ ID NO:6, and the polypeptide sequence of SEQ ID NO:2, or b) a polypeptide sequence of SEQ ID NO:7 or SEQ ID NO:8 or SEQ ID NO:9, or c) the polypeptide sequences of SEQ ID NO:7, and SEQ ID NO:8 and SEQ ID NO:9, or d) the polypeptide sequences of SEQ ID NO:12, and SEQ ID NO:13 and SEQ ID NO:14.

In some embodiments, the PD-1-targeted IL-2 variant immunocytokine used in the combination therapy comprises the polypeptide sequences of SEQ ID NO:7, SEQ ID NO:8 and SEQ ID NO:9.

These PD-1-targeted IL-2 variant immunocytokines, along with their component parts of antigen binding moieties, Fc domains and effector moieties, are described as examples of the immunoconjugates described in WO 2018/184964. For example, the particular immunocytokines 'PD-1-targeted IgG-IL-2 qm fusion protein' based on the anti-CEA antibody CH1A1A 98/99 2F1 and IL-2 quadruple mutant (qm) (SEQ ID NO:3) having the sequences shown as SEQ ID NOs: 7 and 8 and 9 are described in e.g., Examples 1 and 2 of 2018/184964.

Particular PD-1-targeted IL-2 variant immunocytokines described in 2018/184964 are characterized in comprising the following polypeptide sequences as described herein:

| IL-2 mutant | amino acid sequence, SEQ ID NO: |
|---|---|
| IL-2 qm | 3 |

| anti-PD1 antibody | amino acid sequence of the heavy chain variable domain VH, SEQ ID NO: | amino acid sequence of the light chain variable domain VL, SEQ ID NO: |
|---|---|---|
| | 5 | 6 |

| PD-1-targeted IL-2 variant immunocytokine | amino acid sequence of the heavy chain, SEQ ID NOs 7, 8 | amino acid sequence of the light chain, SEQ ID NO: 9 |
|---|---|---|

As described in WO 2012/146628, an IL-2 mutant has reduced binding affinity to the α-subunit of the IL-2 receptor. Together with the β- and γ-subunits (also known as CD122 and CD132, respectively), the α-subunit (also known as CD25) forms the heterotrimeric high affinity IL-2 receptor, while the dimeric receptor consisting only of the β- and γ-subunits is termed the intermediate-affinity IL-2 receptor. As described in WO 2012/146628, an IL-2 mutant polypeptide with reduced binding to the α-subunit of the IL-2 receptor has a reduced ability to induce IL-2 signaling in regulatory T cells, induces less activation-induced cell death (AICD) in T cells, and has a reduced toxicity profile in vivo, compared to a wild-type IL-2 polypeptide. The use of such an IL-2 mutant with reduced toxicity is particularly advantageous in PD-1-targeted IL-2 variant immunocytokines, having a long serum half-life due to the presence of an Fc domain. The IL-2 mutant may comprise at least one amino acid mutation that reduces or abolishes the affinity of the IL-2 mutant to the α-subunit of the IL-2 receptor (CD25) but preserves the affinity of the IL-2 mutant to the intermediate-affinity IL-2 receptor (consisting of the β- and γ-subunits of the IL-2 receptor), compared to wildtype IL-2. The one or more amino acid mutations may be amino acid substitutions. The IL-2 mutant may comprise one, two or three amino acid substitutions at one, two or three position(s) selected from the positions corresponding to residue 42, 45, and 72 of human IL-2 (shown as SEQ ID NO:2). The IL-2 mutant may comprise three amino acid substitutions at the positions corresponding to residue 42, 45 and 72 of human IL-2. The IL-2 mutant may be a mutant of human IL-2. The IL-2 mutant may be human IL-2 comprising the amino acid substitutions F42A, Y45A and L72G. The IL-2 mutant may additionally comprise an amino acid mutation at a position corresponding to position 3 of human IL-2, which eliminates the O-glycosylation site of IL-2. Particularly, said additional amino acid mutation is an amino acid substitution replacing a threonine residue by an alanine residue. A particular IL-2 mutant useful in the invention comprises four amino acid substitutions at positions corresponding to residues 3, 42, 45 and 72 of human IL-2 (shown as SEQ ID NO:2). Specific amino acid substitutions are T3A, F42A, Y45A and L72G. As demonstrated in the Examples of WO 2012/146628, said quadruple mutant IL-2 polypeptide (IL-2 qm) exhibits no detectable binding to CD25, reduced ability to induce apoptosis in T cells, reduced ability to induce IL-2 signaling in $T_{reg}$ cells, and a reduced toxicity profile in vivo. However, it retains ability to activate IL-2 signaling in effector cells, to induce proliferation of effector cells, and to generate IFN-γ as a secondary cytokine by NK cells. The IL-2 mutant according to any of the above descriptions may comprise additional mutations that provide further advantages such as increased expression or stability. For example, the cysteine at position 125 may be replaced with a neutral amino acid such as alanine, to avoid the formation of disulfide-bridged IL-2 dimers. Thus, the IL-2 mutant may comprise an additional amino acid mutation at a position corresponding to residue 125 of human IL-2. Said additional amino acid mutation may be the amino acid substitution C125A. The IL-2 mutant may comprise the polypeptide sequence of SEQ ID NO: 3.

In preferred embodiments, PD-1 targeting of the PD-1-targeted IL-2 variant immunocytokine may be achieved by targeting PD-1, as described in WO 2018/1184964. PD-1-targeting may be achieved with an anti-PD-1 antibody or an antigen binding fragment thereof. An anti-PD-1 antibody may comprise a heavy chain variable region sequence that is at least about 80%, 85%, 90%, 95%, 96%, 97%, 98%, 99% or 100% identical to the sequence of SEQ ID NO: 5 or a variant thereof that retains functionality. An anti-PD-1 antibody may comprise a light chain variable region sequence that is at least about 80%, 85%, 90%, 95%, 96%, 97%, 98%, 99% or 100% identical to the sequence of SEQ ID NO: 6 or a variant thereof that retains functionality. An anti-PD-1 antibody may comprise a heavy chain variable region sequence that is at least about 80%, 85%, 90%, 95%, 96%, 97%, 98%, 99% or 100% identical to the sequence of SEQ ID NO: 5, or a variant thereof that retains functionality, and a light chain variable region sequence that is at least about 80%, 85%, 90%, 95%, 96%, 97%, 98%, 99% or 100% identical to the sequence of SEQ ID NO: 6, or a variant thereof that retains functionality. An anti-PD-1 antibody may comprise the heavy chain variable region sequence of SEQ ID NO: 5 and the light chain variable region sequence of SEQ ID NO: 6.

The PD-1-targeted IL-2 variant immunocytokine may comprise a polypeptide sequence selected from the group consisting of SEQ ID NO: 7, SEQ ID NO: 8 and SEQ ID NO: 9, or a variant thereof that retains functionality. The PD-1-targeted IL-2 variant immunocytokine may comprise a polypeptide sequence wherein a Fab heavy chain specific for CEA shares a carboxy-terminal peptide bond with an Fc domain subunit comprising a hole modification. The PD-1-targeted IL-2 variant immunocytokine may comprise the polypeptide sequence of SEQ ID NO: 7 or SEQ ID NO: 8, or a variant thereof that retains functionality. The PD-1-targeted IL-2 variant immunocytokine may comprise a Fab light chain specific for PD-1. The CEA-targeted IL-2 variant immunocytokine may comprise the polypeptide sequence of SEQ ID NO: 8 or SEQ ID NO: 9, or a variant thereof that retains functionality. The polypeptides may be covalently linked, e.g., by a disulfide bond. The Fc domain polypeptide chains may comprise the amino acid substitutions L234A, L235A, and P329G (which may be referred to as LALA P329G).

As described in WO 2018/184964, the PD-1-targeted IL-2 variant immunocytokine may be a PD-1-targeted IgG-IL-2 qm fusion protein having the sequences shown as SEQ ID NOs: 7, 8 and 9 (as described in e.g. Examples 1 of WO 2018/184964). The PD-1-targeted IL-2 variant immunocytokine having the sequences shown as SEQ ID NOs: 7, 8 and 9 is referred to herein as "PD1-IL2v".

The PD-1-targeted IL-2 variant immunocytokine used in the combination therapy described herein may comprise an antibody which binds to an antigen presented on immune cells, particularly T cells, or in a tumor cell environment, and an IL-2 mutant having reduced binding affinity to the subunit of the IL-2 receptor. The PD-1-targeted IL-2 variant immunocytokine may essentially consist of an antibody which binds to PD-1 presented on immune cells, particularly T cells, or in a tumor cell environment, and an IL-2 mutant having reduced binding affinity to the subunit of the IL-2 receptor. The antibody may be an IgG antibody, particularly an IgG1 antibody. The PD-1-targeted IL-2 variant immunocytokine may comprise a single IL-2 mutant having reduced binding affinity to the subunit of the IL-2 receptor (i.e. not more than one IL-2 mutant moiety is present).

As described herein, the PD-1-targeted IL-2 variant immunocytokine used in the combination therapy described herein may comprise a heavy chain variable domain and a light chain variable domain of an antibody which binds to immune cells, particularly T cells, or in a tumor cell environment and an Fc domain consisting of two subunits and comprising a modification promoting heterodimerization of two non-identical polypeptide chains. The PD-1-targeted IL-2 variant immunocytokine used in the combination therapy described herein may comprise a heavy chain variable domain of an antibody which binds to immune cells, particularly T cells, or in a tumor cell environment and an Fc domain subunit comprising a knob mutation, a heavy chain variable domain of an antibody which binds to immune cells, particularly T cells, or in a tumor cell environment and an Fc domain subunit comprising a hole mutation, and a light chain variable domain of an antibody which binds to immune cells, particularly T cells, or in a tumor cell environment, and an IL-2 mutant having reduced binding affinity to the subunit of the IL-2 receptor. Thus an immunocytokine may comprise an Fc domain comprising a modification promoting heterodimerization of two non-identical polypeptide chains. A "modification promoting heterodimerization" is a manipulation of the peptide backbone or the post-translational modifications of a polypeptide that reduces or prevents the association of the polypeptide with an identical polypeptide to form a homodimer. A modification promoting heterodimerization as used herein particularly includes separate modifications made to each of two polypeptides desired to form a dimer, wherein the modifications are complementary to each other so as to promote association of the two polypeptides. For example, a modification promoting heterodimerization may alter the structure or charge of one or both of the polypeptides desired to form a dimer so as to make their association sterically or electrostatically favorable, respectively. Heterodimerization occurs between two non-identical polypeptides, such as two subunits of an Fc domain wherein further immunoconjugate components fused to each of the subunits (e.g. antigen binding moiety, effector moiety) are not the same. In the immunoconjugates according to the present invention, the modification promoting heterodimerization is in the Fc domain. In some embodiments the modification promoting heterodimerziation comprises an amino acid mutation, specifically an amino acid substitution. In a particular embodiment, the modification promoting heterodimerization comprises a separate amino acid mutation, specifically an amino acid substitution, in each of the two subunits of the Fc domain. The site of most extensive protein-protein interaction between the two polypeptide chains of a human IgG Fc domain is in the CH3 domain of the Fc domain. Thus, in one embodiment said modification is in the CH3 domain of the Fc domain. In a specific embodiment said modification is a knob-into-hole modification, comprising a knob modification in one of the two subunits of the Fc domain and a hole modification in the other one of the two subunits of the Fc domain.

The knob-into-hole technology is described e.g. in U.S. Pat. Nos. 5,731,168; 7,695,936; Ridgway et al., Prot Eng 9, 617-621 (1996) and Carter, J Immunol Meth 248, 7-15 (2001). Generally, the method involves introducing a protuberance ("knob") at the interface of a first polypeptide and a corresponding cavity ("hole") in the interface of a second polypeptide, such that the protuberance can be positioned in the cavity so as to promote heterodimer formation and hinder homodimer formation. Protuberances are constructed by replacing small amino acid side chains from the interface of the first polypeptide with larger side chains (e.g. tyrosine or tryptophan). Compensatory cavities of identical or similar size to the protuberances are created in the interface of the second polypeptide by replacing large amino acid side chains with smaller ones (e.g. alanine or threonine). The protuberance and cavity can be made by altering the nucleic acid encoding the polypeptides, e.g. by site-specific mutagenesis, or by peptide synthesis. In a specific embodiment a knob modification comprises the amino acid substitution T366W in one of the two subunits of the Fc domain, and the hole modification comprises the amino acid substitutions T366S, L368A and Y407V in the other one of the two subunits of the Fc domain. In a further specific embodiment, the subunit of the Fc domain comprising the knob modification additionally comprises the amino acid substitution S354C, and the subunit of the Fc domain comprising the hole modification additionally comprises the amino acid substitution Y349C. Introduction of these two cysteine residues results in formation of a disulfide bridge between the two subunits of the Fc region, further stabilizing the dimer (Carter, J Immunol Methods 248, 7-15 (2001)). Numbering of amino acid residues in the Fc region is according to the EU numbering system, also called the EU index, as described in Kabat et al., Sequences of Proteins of Immunological Interest, 5th Ed. Public Health Service, National Institutes of Health, Bethesda, Md., 1991. A "subunit" of an Fc domain as used herein refers to one of the two polypeptides forming the dimeric Fc domain, i.e. a polypeptide comprising C-terminal constant regions of an immunoglobulin heavy chain, capable of stable self-association. For example, a subunit of an IgG Fc domain comprises an IgG CH2 and an IgG CH3 constant domain.

In an alternative embodiment a modification promoting heterodimerization of two non-identical polypeptide chains comprises a modification mediating electrostatic steering effects, e.g. as described in WO 2009/089004. Generally, this method involves replacement of one or more amino acid residues at the interface of the two polypeptide chains by charged amino acid residues so that homodimer formation becomes electrostatically unfavorable but heterodimerization electrostatically favorable.

An IL-2 mutant having reduced binding affinity to the subunit of the IL-2 receptor may be fused to the carboxy-terminal amino acid of the subunit of the Fc domain comprising the knob modification. Without wishing to be bound by theory, fusion of the IL-2 mutant to the knob-containing subunit of the Fc domain will further minimize the generation of homodimeric immunocoytokines comprising two IL-2 mutant polypeptides (steric clash of two knob-containing polypeptides).

The Fc domain of the immunocytokine may be engineered to have altered binding affinity to an Fc receptor, specifically altered binding affinity to an Fcγ receptor, as compared to a non-engineered Fc domain, as described in WO 2012/146628. Binding of the Fc domain to a complement component, specifically to C1q, may be altered, as described in WO 2012/146628. The Fc domain confers to the immunoconjugate favorable pharmacokinetic properties, including a long serum half-life which contributes to good accumulation in the target tissue and a favorable tissue-blood distribution ratio. At the same time it may, however, lead to undesirable targeting of the immunoconjugate to cells expressing Fc receptors rather than to the preferred antigen-bearing cells. Moreover, the co-activation of Fc receptor signaling pathways may lead to cytokine release which, in combination with the effector moiety and the long half-life of the immunoconjugate, results in excessive activation of cytokine receptors and severe side effects upon systemic administration. In line with this, conventional IgG-IL-2 immunoconjugates have been described to be associated with infusion reactions (see e.g. King et al., J Clin Oncol 22, 4463-4473 (2004)).

Accordingly, the Fc domain of the immunocytokine may be engineered to have reduced binding affinity to an Fc receptor. In one such embodiment the Fc domain comprises one or more amino acid mutation that reduces the binding affinity of the Fc domain to an Fc receptor. Typically, the same one or more amino acid mutation is present in each of the two subunits of the Fc domain. In one embodiment said amino acid mutation reduces the binding affinity of the Fc domain to the Fc receptor by at least 2-fold, at least 5-fold, or at least 10-fold. In embodiments where there is more than one amino acid mutation that reduces the binding affinity of the Fc domain to the Fc receptor, the combination of these amino acid mutations may reduce the binding affinity of the Fc domain to the Fc receptor by at least 10-fold, at least 20-fold, or even at least 50-fold. In one embodiment the immunoconjugate comprising an engineered Fc domain exhibits less than 20%, particularly less than 10%, more particularly less than 5% of the binding affinity to an Fc receptor as compared to an immunoconjugate comprising a non-engineered Fc domain. In one embodiment the Fc receptor is an activating Fc receptor. In a specific embodiment the Fc receptor is an Fcγ receptor, more specifically an Fcγ RIIIa, Fcγ RI or Fcγ RIIa receptor. Preferably, binding to each of these receptors is reduced. In some embodiments binding affinity to a complement component, specifically binding affinity to C1q, is also reduced. In one embodiment binding affinity to neonatal Fc receptor (FcRn) is not reduced. Substantially similar binding to FcRn, i.e. preservation of the binding affinity of the Fc domain to said receptor, is achieved when the Fc domain (or the immunoconjugate comprising said Fc domain) exhibits greater than about 70% of the binding affinity of a non-engineered form of the Fc domain (or the immunoconjugate comprising said non-engineered form of the Fc domain) to FcRn. Fc domains, or immunoconjugates of the invention comprising said Fc domains, may exhibit greater than about 80% and even greater than about 90% of such affinity. In one embodiment the amino acid mutation is an amino acid substitution. In one embodiment the Fc domain comprises an amino acid substitution at position P329. In a more specific embodiment the amino acid substitution is P329A or P329G, particularly P329G. In one embodiment the Fc domain comprises a further amino acid substitution at a position selected from S228, E233, L234, L235, N297 and P331. In a more specific embodiment the further amino acid substitution is S228P, E233P, L234A, L235A, L235E, N297A, N297D or P331S. In a particular embodiment the Fc domain comprises amino acid substitutions at positions P329, L234 and L235. In a more particular embodiment the Fc domain comprises the amino acid mutations L234A, L235A and P329G (LALA P329G). This combination of amino acid substitutions almost completely abolishes Fcγ receptor binding of a human IgG Fc domain, as described in WO 2012/130831, incorporated herein by reference in its entirety. WO 2012/130831 also describes methods of preparing such mutant Fc domains and methods for determining its properties such as Fc receptor binding or effector functions. Numbering of amino acid residues in the Fc region is according to the EU numbering system, also called the EU index, as described in Kabat et al., Sequences of Proteins of Immunological Interest, 5th Ed. Public Health Service, National Institutes of Health, Bethesda, Md., 1991.

Mutant Fc domains can be prepared by amino acid deletion, substitution, insertion or modification using genetic or chemical methods well known in the art and as described in WO 2012/146628. Genetic methods may include site-specific mutagenesis of the encoding DNA sequence, PCR, gene synthesis, and the like. The correct nucleotide changes can be verified for example by sequencing.

In one embodiment the Fc domain is engineered to have decreased effector function, compared to a non-engineered Fc domain, as described in WO 2012/146628. The decreased effector function can include, but is not limited to, one or more of the following: decreased complement dependent cytotoxicity (CDC), decreased antibody-dependent cell-mediated cytotoxicity (ADCC), decreased antibody-dependent cellular phagocytosis (ADCP), decreased cytokine secretion, decreased immune complex-mediated antigen uptake by antigen-presenting cells, decreased binding to NK cells, decreased binding to macrophages, decreased binding to monocytes, decreased binding to polymorphonuclear cells, decreased direct signaling inducing apoptosis, decreased crosslinking of target-bound antibodies, decreased dendritic cell maturation, or decreased T cell priming.

$IgG_4$ antibodies exhibit reduced binding affinity to Fc receptors and reduced effector functions as compared to $IgG_1$ antibodies. Hence, in some embodiments the Fc domain of the T cell activating bispecific antigen binding molecules of the invention is an $IgG_4$ Fc domain, particularly a human $IgG_4$ Fc domain. In one embodiment the $IgG_4$ Fc domain comprises amino acid substitutions at position S228, specifically the amino acid substitution S228P. To further reduce its binding affinity to an Fc receptor and/or its effector function, in one embodiment the $IgG_4$ Fc domain comprises an amino acid substitution at position L235, specifically the amino acid substitution L235E. In another embodiment, the $IgG_4$ Fc domain comprises an amino acid substitution at position P329, specifically the amino acid substitution P329G. In a particular embodiment, the $IgG_4$ Fc domain comprises amino acid substitutions at positions S228, L235 and P329, specifically amino acid substitutions S228P, L235E and P329G. Such $IgG_4$ Fc domain mutants and their Fcγ receptor binding properties are described in European patent application no. WO 2012/130831, incorporated herein by reference in its entirety.

The antibody which binds to human PD-L1 used in the combination therapy described herein is selected from the group consisting of:

243.55.S70, 243.55.H1, 243.55.H12, 243.55.H37, 243.55.H70, 243.55.H89, 243.55.51, 243.55.5, 243.55.8, 243.55.30, 243.55.34, 243.55.S37, 243.55.49, 243.55.51, 243.55.62, and 243.55.84.

These antibodies are described in WO 2010/77634 (sequences are shown in FIG. 11 of WO 2010/77634).

In an embodiment of the invention the PD1-targeted IL-2 variant immunocytokine used in the combination therapy described herein is characterized in comprising a) a heavy chain variable domain VH of SEQ ID NO:5 and a light chain variable domain VL of SEQ ID NO:6, and the polypeptide sequence of SEQ ID NO:2, orb) a polypeptide sequence of SEQ ID NO:7 or SEQ ID NO:8 or SEQ ID NO:9, or c) the polypeptide sequences of SEQ ID NO:7, and SEQ ID NO:8 and SEQ ID NO:9, or d) the polypeptide sequences of SEQ ID NO:12, and SEQ ID NO:13 and SEQ ID NO:14, and the antibody which binds to human PD-L1 used in the combination therapy is characterized in comprising a) a heavy chain variable domain VH of SEQ ID NO:15 and a light chain variable domain VL of SEQ ID NO:16, or b) a heavy chain variable domain VH of SEQ ID NO:19 and a light chain variable domain VL of SEQ ID NO:20.

In an embodiment the PD-1-targeted IL-2 variant immunocytokine used in the combination therapy described herein is characterized in comprising the heavy chain variable domain VH of SEQ ID NO:5 and the light chain variable domain VL of SEQ ID NO:6, and the polypeptide sequence of SEQ ID NO:2.

In an embodiment the PD-1-targeted IL-2 variant immunocytokine used in the combination therapy described herein is characterized in comprising the polypeptide sequences of SEQ ID NO:7, and SEQ ID NO:8 and SEQ ID NO:9.

In one embodiment the antibody which binds to human PD-L1 used in the combination therapy is characterized in comprising a heavy chain variable domain VH of SEQ ID NO:15 and a light chain variable domain VL of SEQ ID NO:16.

In a preferred embodiment of the invention the PD1-targeted IL-2 variant immunocytokine used in the combination therapy described herein is characterized in comprising the polypeptide sequences of SEQ ID NO:7, and SEQ ID NO:8 and SEQ ID NO:9, and the antibody which binds to human PD-L1 used in the combination therapy is characterized in comprising a heavy chain variable domain VH of SEQ ID NO:15 and a light chain variable domain VL of SEQ ID NO:16.

In a preferred embodiment of the invention the PD1-targeted IL-2 variant immunocytokine used in the combination therapy described herein is characterized in comprising the polypeptide sequences of SEQ ID NO:7, and SEQ ID NO:8 and SEQ ID NO:9, and the antibody which binds to human PD-L1 used in the combination therapy is atezolizumab.

Definitions

The term "antibody" herein is used in the broadest sense and encompasses various antibody structures, including but not limited to monoclonal antibodies, polyclonal antibodies, and antibody fragments so long as they exhibit the desired antigen-binding activity.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')2, diabodies, linear antibodies, single-chain antibody molecules (e.g. scFv), and single-domain antibodies. For a review of certain antibody fragments, see Hudson et al., Nat Med 9, 129-134 (2003). For a review of scFv fragments, see e.g. Plückthun, in The Pharmacology of Monoclonal Antibodies, vol. 113, Rosenburg and Moore eds., Springer-Verlag, New York, pp. 269-315 (1994); see also WO 93/16185; and U.S. Pat. Nos. 5,571,894 and 5,587,458. For discussion of Fab and F(ab')2 fragments comprising salvage receptor binding epitope residues and having increased in vivo half-life, see U.S. Pat. No. 5,869,046. Diabodies are antibody fragments with two antigen binding sites that may be bivalent or bispecific. See, for example, EP 404,097; WO 1993/01161; Hudson et al., Nat Med 9, 129-134 (2003); and Hollinger et al., Proc Natl Acad Sci USA 90, 6444-6448 (1993). Triabodies and tetrabodies are also described in Hudson et al., Nat Med 9, 129-134 (2003). Single-domain antibodies are antibody fragments comprising all or a portion of the heavy chain variable domain or all or a portion of the light chain variable domain of an antibody. In certain embodiments, a single-domain antibody is a human single-domain antibody (Domantis, Inc., Waltham, Mass.; see e.g. U.S. Pat. No. 6,248,516 B1). Antibody fragments can be made by various techniques, including but not limited to proteolytic digestion of an intact antibody as well as production by recombinant host cells (e.g. *E. coli* or phage), as described herein.

The term "antigen binding domain" or "antigen-binding portion of an antibody" when used herein refers to the part of an antibody that comprises the area which specifically binds to and is complementary to part or all of an antigen. The term thus refers to the amino acid residues of an antibody which are responsible for antigen-binding. An antigen binding domain may be provided by, for example, one or more antibody variable domains (also called antibody variable regions). Particularly, an antigen binding domain comprises an antibody light chain variable region (VL) and an antibody heavy chain variable region (VH). The antigen-binding portion of an antibody comprises amino acid residues from the "complementary determining regions" or "CDRs". "Framework" or "FR" regions are those variable domain regions other than the hypervariable region residues as herein defined. Therefore, the light and heavy chain variable domains of an antibody comprise from N- to C-terminus the domains FR1, CDR1, FR2, CDR2, FR3, CDR3, and FR4. Especially, CDR3 of the heavy chain is the region which contributes most to antigen binding and defines the antibody's properties. CDR and FR regions are determined according to the standard definition of Kabat et al., Sequences of Proteins of Immunological Interest, 5th ed., Public Health Service, National Institutes of Health, Bethesda, Md. (1991) and/or those residues from a "hypervariable loop".

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs). See, e.g., Kindt et al., Kuby Immunology, 6th ed., W.H. Freeman and Co., page 91 (2007). A single VH or VL domain may be sufficient to confer antigen-binding specificity.

The term "epitope" denotes a protein determinant of an antigen, such as a CEA or human PD-L1, capable of specifically binding to an antibody. Epitopes usually consist of chemically active surface groupings of molecules such as amino acids or sugar side chains and usually epitopes have specific three dimensional structural characteristics, as well as specific charge characteristics. Conformational and non-conformational epitopes are distinguished in that the binding to the former but not the latter is lost in the presence of denaturing solvents.

The term "Fc domain" or "Fc region" herein is used to define a C-terminal region of an immunoglobulin heavy chain that contains at least a portion of the constant region. The term includes native sequence Fc regions and variant Fc regions. Although the boundaries of the Fc region of an IgG heavy chain might vary slightly, the human IgG heavy chain Fc region is usually defined to extend from Cys226, or from Pro230, to the carboxyl-terminus of the heavy chain. However, the C-terminal lysine (Lys447) of the Fc region may or may not be present. Unless otherwise specified herein, numbering of amino acid residues in the Fc region or constant region is according to the EU numbering system, also called the EU index, as described in Kabat et al., Sequences of Proteins of Immunological Interest, 5th Ed. Public Health Service, National Institutes of Health, Bethesda, Md., 1991. The Fc domain of an antibody is not involved directly in binding of an antibody to an antigen, but exhibit various effector functions. A "Fc domain of an antibody" is a term well known to the skilled artisan and defined on the basis of papain cleavage of antibodies. Depending on the amino acid sequence of the constant region of their heavy chains, antibodies or immunoglobulins are divided in the classes: IgA, IgD, IgE, IgG and IgM, and several of these may be further divided into subclasses (isotypes), e.g. IgG1, IgG2, IgG3, and IgG4, IgA1, and IgA2. According to the heavy chain constant regions the different classes of immunoglobulins are called α, δ, ε, γ, and μ, respectively. The Fc domain of an antibody is directly involved in ADCC (antibody-dependent cell-mediated cytotoxicity) and CDC (complement-dependent cytotoxicity) based on complement activation, C1q binding and Fc receptor binding. Complement activation (CDC) is initiated by binding of complement factor C1q to the Fc domain of most IgG antibody subclasses. While the influence of an antibody on the complement system is dependent on certain conditions, binding to C1q is caused by defined binding sites in the Fc domain. Such binding sites are known in the state of the art and described e.g. by Boackle, R. J., et al., Nature 282 (1979) 742-743; Lukas, T. J., et al., J. Immunol. 127 (1981) 2555-2560; Brunhouse, R., and Cebra, J. J., Mol. Immunol. 16 (1979) 907-917; Burton, D. R., et al., Nature 288 (1980) 338-344; Thommesen, J. E., et al., Mol. Immunol. 37 (2000) 995-1004; Idusogie, E. E., et al., J. Immunol. 164 (2000) 4178-4184; Hezareh, M., et al., J. Virology 75 (2001) 12161-12168; Morgan, A., et al., Immunology 86 (1995) 319-324; EP 0 307 434. Such binding sites are e.g. L234, L235, D270, N297, E318, K320, K322, P331 and P329 (numbering according to EU index of Kabat, E. A., see above). Antibodies of subclass IgG1, IgG2 and IgG3 usually show complement activation and C1q and C3 binding, whereas IgG4 do not activate the complement system and do not bind C1q and C3.

In one embodiment an antibody component of an immunocytokine or an antibody described herein comprises an Fc domain derived from human origin and preferably all other parts of the human constant regions. As used herein the term "Fc domain derived from human origin" denotes a Fc domain which is either a Fc domain of a human antibody of the subclass IgG1, IgG2, IgG3 or IgG4, preferably a Fc domain from human IgG1 subclass, a mutated Fc domain from human IgG1 subclass (in one embodiment with a mutation on L234A+L235A), a Fc domain from human IgG4 subclass or a mutated Fc domain from human IgG4 subclass (in one embodiment with a mutation on S228P). In one embodiment said antibodies have reduced or minimal effector function. In one embodiment the minimal effector function results from an effector less Fc mutation. In one embodiment the effector less Fc mutation is L234A/L235A or L234A/L235A/P329G or N297A or D265A/N297A. In one embodiment the effector less Fc mutation is selected for each of the antibodies independently of each other from the group comprising (consisting of) L234A/L235A, L234A/L235A/P329G, N297A and D265A/N297A (EU numbering).

In one embodiment the antibody components of immunocytokines or antibodies described herein are of human IgG class (i.e. of IgG1, IgG2, IgG3 or IgG4 subclass).

In a preferred embodiment the antibody components of immunocytokines or antibodies described herein are of human IgG1 subclass or of human IgG4 subclass. In one embodiment the antibody components of immunocytokines or antibodies described herein are of human IgG1 subclass. In one embodiment the antibody components of immunocytokines or antibodies described herein are of human IgG4 subclass.

In one embodiment an antibody component of an immunocytokine or an antibody described herein is characterized in that the constant chains are of human origin. Such constant chains are well known in the state of the art and e.g. described by Kabat, E. A., (see e.g. Johnson, G. and Wu, T. T., Nucleic Acids Res. 28 (2000) 214-218).

The terms "nucleic acid" or "nucleic acid molecule", as used herein, are intended to include DNA molecules and RNA molecules. A nucleic acid molecule may be single-stranded or double-stranded, but preferably is double-stranded DNA.

The term "amino acid" as used within this application denotes the group of naturally occurring carboxy alpha-amino acids comprising alanine (three letter code: ala, one letter code: A), arginine (arg, R), asparagine (asn, N), aspartic acid (asp, D), cysteine (cys, C), glutamine (gln, Q), glutamic acid (glu, E), glycine (gly, G), histidine (his, H), isoleucine (ile, I), leucine (leu, L), lysine (lys, K), methionine (met, M), phenylalanine (phe, F), proline (pro, P), serine (ser, S), threonine (thr, T), tryptophan (trp, W), tyrosine (tyr, Y), and valine (val, V).

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code.

The ALIGN-2 program should be compiled for use on a UNIX operating system, including digital UNIX V4.0D. All sequence comparison parameters are set by the ALIGN-2 program and do not vary. In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction X/Y where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program. By a nucleic acid or polynucleotide having a nucleotide sequence at least, for example, 95% "identical" to a reference nucleotide sequence of the present invention, it is intended that the nucleotide sequence of the polynucleotide is identical to the reference sequence except that the polynucleotide sequence may include up to five point mutations per each 100 nucleotides of the reference nucleotide sequence. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These alterations of the reference sequence may occur at the 5' or 3' terminal positions of the reference nucleotide sequence or anywhere between those terminal positions, interspersed either individually among residues in the reference sequence or in one or more contiguous groups within the reference sequence. As a practical matter, whether any particular polynucleotide sequence is at least 80%, 85%, 90%, 95%, 96%, 97%, 98% or 99% identical to a nucleotide sequence of the present invention can be determined conventionally using known computer programs, such as the ones discussed above for polypeptides (e.g. ALIGN-2).

The term "expression cassette" refers to a polynucleotide generated recombinantly or synthetically, with a series of specified nucleic acid elements that permit transcription of a particular nucleic acid in a target cell. The recombinant expression cassette can be incorporated into a plasmid, chromosome, mitochondrial DNA, plastid DNA, virus, or nucleic acid fragment. Typically, the recombinant expression cassette portion of an expression vector includes, among other sequences, a nucleic acid sequence to be transcribed and a promoter. In certain embodiments, the expression cassette of the invention comprises polynucleotide sequences that encode polypeptides described herein or fragments thereof.

The term "vector" or "expression vector" is synonymous with "expression construct" and refers to a DNA molecule that is used to introduce and direct the expression of a specific gene to which it is operably associated in a target cell. The term includes the vector as a self-replicating nucleic acid structure as well as the vector incorporated into the genome of a host cell into which it has been introduced. The expression vector comprises an expression cassette. Expression vectors allow transcription of large amounts of stable mRNA. Once the expression vector is inside the target cell, the ribonucleic acid molecule or protein that is encoded by the gene is produced by the cellular transcription and/or translation machinery. In one embodiment, the expression vector comprises an expression cassette that comprises polynucleotide sequences that encode polypeptides described herein or fragments thereof.

The term "artificial" refers to a synthetic, or non-host cell derived composition, e.g. a chemically-synthesized oligonucleotide.

The terms "host cell", "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein. A host cell is any type of cellular system that can be used to generate the polypeptides described herein. In one embodiment, the host cell is engineered to allow the production of a polypeptide with modified oligosaccharides in its Fc region. In certain embodiments, the host cells have been manipulated to express increased levels of one or more polypeptides having β (1,4)-N-acetylglucosaminyltransferase III (GnTIII) activity. In certain embodiments the host cells have been further manipulated to express increased levels of one or more polypeptides having α-mannosidase II (ManII) activity. Host cells include cultured cells, e.g. mammalian cultured cells, such as CHO cells, BHK cells, NS0 cells, SP2/0 cells, YO myeloma cells, P3X63 mouse myeloma cells, PER cells, PER.C6 cells or hybridoma cells, yeast cells, insect cells, and plant cells, to name only a few, but also cells comprised within a transgenic animal, transgenic plant or cultured plant or animal tissue.

PD-1-targeted IL-2 variant immunocytokines described herein may be obtained, for example, by solid-state peptide synthesis (e.g. Merrifield solid phase synthesis) or recombinant production. For recombinant production one or more polynucleotide encoding the immunocytokine (fragment), e.g., as described above, is isolated and inserted into one or more vectors for further cloning and/or expression in a host cell. Such polynucleotide may be readily isolated and sequenced using conventional procedures. In one embodiment a vector, preferably an expression vector, comprising one or more of the polynucleotides is provided. Methods which are well known to those skilled in the art can be used to construct expression vectors containing the coding sequence of an immunoconjugate (fragment) along with appropriate transcriptional/translational control signals. These methods include in vitro recombinant DNA techniques, synthetic techniques and in vivo recombination/genetic recombination. See, for example, the techniques described in Maniatis et al., Molecular Cloning: A Laboratory Manual, Cold Spring Harbor Laboratory, N.Y. (1989); and Ausubel et al., Current Protocols in Molecular Biology, Greene Publishing Associates and Wiley Interscience, N.Y (1989). The expression vector can be part of a plasmid, virus, or may be a nucleic acid fragment. The expression vector includes an expression cassette into which the polynucleotide encoding the immunocytokine (fragment) (i.e. the coding region) is cloned in operable association with a promoter and/or other transcription or translation control elements. As used herein, a "coding region" is a portion of nucleic acid which consists of codons translated into amino acids. Although a "stop codon" (TAG, TGA, or TAA) is not translated into an amino acid, it may be considered to be part of a coding region, if present, but any flanking sequences, for example promoters, ribosome binding sites, transcriptional terminators, introns, 5' and 3' untranslated regions, and the like, are not part of a coding region. Two or more coding regions can be present in a single polynucleotide construct, e.g. on a single vector, or in separate polynucleotide constructs, e.g. on separate (different) vectors. Furthermore, any vector may contain a single coding region, or may comprise two or more coding regions, e.g. a vector may encode one or more polypeptides, which are post- or co-translationally separated into the final proteins via proteolytic cleavage. In addition, a vector, polynucleotide, or nucleic acid may encode heterologous coding regions, either fused or unfused to a polynucleotide encoding the immunocytokine (fragment), or variant or derivative thereof. Heterologous coding regions include without limitation specialized elements or motifs, such as a secretory signal peptide or a heterologous functional domain. An operable association is when a coding region for a gene product, e.g. a polypeptide, is associated with one or more regulatory sequences in such a way as to place expression of the gene product under the influence or control of the regulatory sequence(s). Two DNA fragments (such as a polypeptide coding region and a promoter associated therewith) are "operably associated" if induction of promoter function results in the transcription of mRNA encoding the desired gene product and if the nature of the linkage between the two DNA fragments does not interfere with the ability of the expression regulatory sequences to direct the expression of the gene product or interfere with the ability of the DNA template to be transcribed. Thus, a promoter region would be operably associated with a nucleic acid encoding a polypeptide if the promoter was capable of effecting transcription of that nucleic acid. The promoter may be a cell-specific promoter that directs substantial transcription of the DNA only in predetermined cells. Other transcription control elements, besides a promoter, for example enhancers, operators, repressors, and transcription termination signals, can be operably associated with the polynucleotide to direct cell-specific transcription. Suitable promoters and other transcription control regions are disclosed herein. A variety of transcription control regions are known to those skilled in the art. These include, without limitation, transcription control regions, which function in vertebrate cells, such as, but not limited to, promoter and enhancer segments from cytomegaloviruses (e.g. the immediate early promoter, in conjunction with intron-A), simian virus 40 (e.g. the early promoter), and retroviruses (such as, e.g. Rous sarcoma virus). Other transcription control regions include those derived from vertebrate genes such as actin, heat shock protein, bovine growth hormone and rabbit â-globin, as well as other sequences capable of controlling gene expression in eukaryotic cells. Additional suitable transcription control regions include tissue-specific promoters and enhancers as well as inducible promoters (e.g. promoters inducible tetracyclins). Similarly, a variety of translation control elements are known to those of ordinary skill in the art. These include, but are not limited to ribosome binding sites, translation initiation and termination codons, and elements derived from viral systems (particularly an internal ribosome entry site, or IRES, also referred to as a CITE sequence). The expression cassette may also include other features such as an origin of replication, and/or chromosome integration elements such as retroviral long terminal repeats (LTRs), or adeno-associated viral (AAV) inverted terminal repeats (ITRs).

Polynucleotide and nucleic acid coding regions described herein may be associated with additional coding regions which encode secretory or signal peptides, which direct the secretion of a polypeptide encoded by a polynucleotide. For example, if secretion of the immunocytokine is desired, DNA encoding a signal sequence may be placed upstream of the nucleic acid encoding an immunocytokine or a fragment thereof. According to the signal hypothesis, proteins secreted by mammalian cells have a signal peptide or secretory leader sequence which is cleaved from the mature protein once export of the growing protein chain across the rough endoplasmic reticulum has been initiated. Those of ordinary skill in the art are aware that polypeptides secreted by vertebrate cells generally have a signal peptide fused to the N-terminus of the polypeptide, which is cleaved from the translated polypeptide to produce a secreted or "mature" form of the polypeptide. In certain embodiments, the native signal peptide, e.g. an immunoglobulin heavy chain or light chain signal peptide is used, or a functional derivative of that sequence that retains the ability to direct the secretion of the polypeptide that is operably associated with it. Alternatively, a heterologous mammalian signal peptide, or a functional derivative thereof, may be used. For example, the wild-type leader sequence may be substituted with the leader sequence of human tissue plasminogen activator (TPA) or mouse β-glucuronidase.

DNA encoding a short protein sequence that could be used to facilitate later purification (e.g. a histidine tag) or assist in labeling the immunocytokine may be included within or at the ends of the immunocytokine (fragment) encoding polynucleotide.

In a further embodiment, a host cell comprising one or more polynucleotides described herein is provided. In certain embodiments a host cell comprising one or more vectors described herein is provided. The polynucleotides and vectors may incorporate any of the features, singly or in combination, described herein in relation to polynucleotides and vectors, respectively. In one such embodiment a host cell comprises (e.g. has been transformed or transfected with) a vector comprising a polynucleotide that encodes (part of) an immunocytokine described herein. As used herein, the term "host cell" refers to any kind of cellular system which can be engineered to generate the immunocytokines or fragments thereof. Host cells suitable for replicating and for supporting expression of immunocytokines are well known in the art. Such cells may be transfected or transduced as appropriate with the particular expression vector and large quantities of vector containing cells can be grown for seeding large scale fermenters to obtain sufficient quantities of the immunocytokine for clinical applications. Suitable host cells include prokaryotic microorganisms, such as *E. coli*, or various eukaryotic cells, such as Chinese hamster ovary cells (CHO), insect cells, or the like. For example, polypeptides may be produced in bacteria in particular when glycosylation is not needed. After expression, the polypeptide may be isolated from the bacterial cell paste in a soluble fraction and can be further purified. In addition to prokaryotes, eukaryotic microbes such as filamentous fungi or yeast are suitable cloning or expression hosts for polypeptide-encoding vectors, including fungi and yeast strains whose glycosylation pathways have been "humanized", resulting in the production of a polypeptide with a partially or fully human glycosylation pattern. See Gerngross, Nat Biotech 22, 1409-1414 (2004), and Li et al., Nat Biotech 24, 210-215 (2006). Suitable host cells for the expression of (glycosylated) polypeptides are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells. Plant cell cultures can also be utilized as hosts. See e.g. U.S. Pat. Nos. 5,959,177, 6,040,498, 6,420,548, 7,125,978, and 6,417,429 (describing PLANTIBODIES™ technology for producing antibodies in transgenic plants). Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293T cells as described, e.g., in Graham et al., J Gen Virol 36, 59 (1977)), baby hamster kidney cells (BHK), mouse sertoli cells (TM4 cells as described, e.g., in Mather, Biol Reprod 23, 243-251 (1980)), monkey kidney cells (CV1), African green monkey kidney cells (VERO-76), human cervical carcinoma cells (HELA), canine kidney cells (MDCK), buffalo rat liver cells (BRL 3A), human lung cells (W138), human liver cells (Hep G2), mouse mammary tumor cells (MMT 060562), TRI cells (as described, e.g., in Mather et al., Annals N.Y. Acad Sci 383, 44-68 (1982)), MRC 5 cells, and FS4 cells. Other useful mammalian host cell lines include Chinese hamster ovary (CHO) cells, including dhfr CHO cells (Urlaub et al., Proc Natl Acad Sci USA 77, 4216 (1980)); and myeloma cell lines such as YO, NS0, P3X63 and Sp2/0. For a review of certain mammalian host cell lines suitable for protein production, see, e.g., Yazaki and Wu, Methods in Molecular Biology, Vol. 248 (B. K. C. Lo, ed., Humana Press, Totowa, N.J.), pp. 255-268 (2003). Host cells include cultured cells, e.g., mammalian cultured cells, yeast cells, insect cells, bacterial cells and plant cells, to name only a few, but also cells comprised within a transgenic animal, transgenic plant or cultured plant or animal tissue. In one embodiment, the host cell is a eukaryotic cell, preferably a mammalian cell, such as a Chinese Hamster Ovary (CHO) cell, a human embryonic kidney (HEK) cell or a lymphoid cell (e.g., Y0, NS0, Sp20 cell).

Standard technologies are known in the art to express foreign genes in these systems. Cells expressing a polypeptide comprising either the heavy or the light chain of an antibody, may be engineered so as to also express the other of the antibody chains such that the expressed product is an antibody that has both a heavy and a light chain.

A method of producing an immunocoytokine described herein is provided, wherein the method comprises culturing a host cell comprising a polynucleotide encoding the immunocytokine, as provided herein, under conditions suitable for expression of the immunocytokine, and recovering the immunocytokine from the host cell (or host cell culture medium).

The components of the immunocytokine are genetically fused to each other. Immunocytokines can be designed such that its components are fused directly to each other or indirectly through a linker sequence. The composition and length of the linker may be determined in accordance with methods well known in the art and may be tested for efficacy. Additional sequences may also be included to incorporate a cleavage site to separate the individual components of the fusion if desired, for example an endopeptidase recognition sequence.

The immunocytokine comprises at least an antibody variable region capable of binding an antigenic determinant. Variable regions can form part of and be derived from naturally or non-naturally occurring antibodies and fragments thereof. Methods to produce polyclonal antibodies and monoclonal antibodies are well known in the art (see e.g. Harlow and Lane, "Antibodies, a laboratory manual", Cold Spring Harbor Laboratory, 1988). Non-naturally occurring antibodies can be constructed using solid phase-peptide synthesis, can be produced recombinantly (e.g. as described in U.S. Pat. No. 4,186,567) or can be obtained, for example, by screening combinatorial libraries comprising variable heavy chains and variable light chains (see e.g. U.S. Pat. No. 5,969,108 to McCafferty). Antigen binding moieties and methods for producing the same are also described in detail in PCT publication WO 2011/020783, the entire content of which is incorporated herein by reference.

Any animal species of antibody, antibody fragment, antigen binding domain or variable region can be used in the immunocytokines described herein. Non-limiting antibodies, antibody fragments, antigen binding domains or variable regions useful in the present invention can be of murine, primate, or human origin. Where the immunocytokine is intended for human use, a chimeric form of antibody may be used wherein the constant regions of the antibody are from a human. A humanized or fully human form of the antibody can also be prepared in accordance with methods well known in the art (see e.g. U.S. Pat. No. 5,565,332 to Winter).

Humanization may be achieved by various methods including, but not limited to (a) grafting the non-human (e.g., donor antibody) CDRs onto human (e.g. recipient antibody) framework and constant regions with or without retention of critical framework residues (e.g. those that are important for retaining good antigen binding affinity or antibody functions), (b) grafting only the non-human specificity-determining regions (SDRs or a-CDRs; the residues critical for the antibody-antigen interaction) onto human framework and constant regions, or (c) transplanting the entire non-human variable domains, but "cloaking" them with a human-like section by replacement of surface residues. Humanized antibodies and methods of making them are reviewed, e.g., in Almagro and Fransson, Front Biosci 13, 1619-1633 (2008), and are further described, e.g., in Riechmann et al., Nature 332, 323-329 (1988); Queen et al., Proc Natl Acad Sci USA 86, 10029-10033 (1989); U.S. Pat. Nos. 5,821,337, 7,527,791, 6,982,321, and 7,087,409; Jones et al., Nature 321, 522-525 (1986); Morrison et al., Proc Natl Acad Sci 81, 6851-6855 (1984); Morrison and Oi, Adv Immunol 44, 65-92 (1988); Verhoeyen et al., Science 239, 1534-1536 (1988); Padlan, Molec Immun 31(3), 169-217 (1994); Kashmiri et al., Methods 36, 25-34 (2005) (describing SDR (a-CDR) grafting); Padlan, Mol Immunol 28, 489-498 (1991) (describing "resurfacing"); Dall'Acqua et al., Methods 36, 43-60 (2005) (describing "FR shuffling"); and Osbourn et al., Methods 36, 61-68 (2005) and Klimka et al., Br J Cancer 83, 252-260 (2000) (describing the "guided selection" approach to FR shuffling). Human antibodies and human variable regions can be produced using various techniques known in the art. Human antibodies are described generally in van Dijk and van de Winkel, Curr Opin Pharmacol 5, 368-74 (2001) and Lonberg, Curr Opin Immunol 20, 450-459 (2008). Human variable regions can form part of and be derived from human monoclonal antibodies made by the hybridoma method (see e.g. Monoclonal Antibody Production Techniques and Applications, pp. 51-63 (Marcel Dekker, Inc., New York, 1987)). Human antibodies and human variable regions may also be prepared by administering an immunogen to a transgenic animal that has been modified to produce intact human antibodies or intact antibodies with human variable regions in response to antigenic challenge (see e.g. Lonberg, Nat Biotech 23, 1117-1125 (2005). Human antibodies and human variable regions may also be generated by isolating Fv clone variable region sequences selected from human-derived phage display libraries (see e.g., Hoogenboom et al. in Methods in Molecular Biology 178, 1-37 (O'Brien et al., ed., Human Press, Totowa, N.J., 2001); and McCafferty et al., Nature 348, 552-554; Clackson et al., Nature 352, 624-628 (1991)). Phage typically display antibody fragments, either as single-chain Fv (scFv) fragments or as Fab fragments. A detailed description of the preparation of antigen binding moieties for immunoconjugates by phage display can be found in the Examples appended to PCT publication WO 2011/020783.

In certain embodiments, antibodies are engineered to have enhanced binding affinity according to, for example, the methods disclosed in PCT publication WO 2011/020783 (see Examples relating to affinity maturation) or U.S. Pat. Appl. Publ. No. 2004/0132066, the entire contents of which are hereby incorporated by reference. The ability of the immunocytokine to bind to a specific antigenic determinant can be measured either through an enzyme-linked immunosorbent assay (ELISA) or other techniques familiar to one of skill in the art, e.g. surface plasmon resonance technique (analyzed on a BIACORE T100 system) (Liljeblad, et al., Glyco J 17, 323-329 (2000)), and traditional binding assays (Heeley, Endocr Res 28, 217-229 (2002)). Competition assays may be used to identify an antibody, antibody fragment, antigen binding domain or variable domain that competes with a reference antibody for binding to a particular antigen, e.g. an antibody that competes with the CH1A1A 98/99 2F1 antibody for binding to CEA. In certain embodiments, such a competing antibody binds to the same epitope (e.g. a linear or a conformational epitope) that is bound by the reference antibody. Detailed exemplary methods for mapping an epitope to which an antibody binds are provided in Morris (1996) "Epitope Mapping Protocols," in Methods in Molecular Biology vol. 66 (Humana Press, Totowa, N.J.). In an exemplary competition assay, immobilized antigen (e.g. CEA) is incubated in a solution comprising a first labeled antibody that binds to the antigen (e.g. CH1A1A 98/99 2F1 antibody) and a second unlabeled antibody that is being tested for its ability to compete with the first antibody for binding to the antigen. The second antibody may be present in a hybridoma supernatant. As a control, immobilized antigen is incubated in a solution comprising the first labeled antibody but not the second unlabeled antibody. After incubation under conditions permissive for binding of the first antibody to the antigen, excess unbound antibody is removed, and the amount of label associated with immobilized antigen is measured. If the amount of label associated with immobilized antigen is substantially reduced in the test sample relative to the control sample, then that indicates that the second antibody is competing with the first antibody for binding to the antigen. See Harlow and Lane (1988) Antibodies: A Laboratory Manual ch.14 (Cold Spring Harbor Laboratory, Cold Spring Harbor, N.Y.).

Immunocoytokines prepared as described herein may be purified by art-known techniques such as high performance liquid chromatography, ion exchange chromatography, gel electrophoresis, affinity chromatography, size exclusion chromatography, and the like. The actual conditions used to purify a particular protein will depend, in part, on factors such as net charge, hydrophobicity, hydrophilicity etc., and will be apparent to those having skill in the art. For affinity chromatography purification an antibody, ligand, receptor or antigen can be used to which the immunocytokine binds. For example, for affinity chromatography purification of immunocytokines, a matrix with protein A or protein G may be used. Sequential Protein A or G affinity chromatography and size exclusion chromatography can be used to isolate an immunocytokine essentially as described in the Examples of WO 2012/146628. The purity of the immunocytokine can be determined by any of a variety of well known analytical methods including gel electrophoresis, high pressure liquid chromatography, and the like. For example, immunocytokines may be shown to be intact and properly assembled as demonstrated by reducing SDS-PAGE.

PD-1-targeted IL-2 variant immunocytokines described herein may be prepared as described in the Examples of WO 2018/184964.

Antibodies described herein are preferably produced by recombinant means. Such methods are widely known in the state of the art and comprise protein expression in prokaryotic and eukaryotic cells with subsequent isolation of the antibody polypeptide and usually purification to a pharmaceutically acceptable purity. For the protein expression nucleic acids encoding light and heavy chains or fragments thereof are inserted into expression vectors by standard methods. Expression is performed in appropriate prokaryotic or eukaryotic host cells, such as CHO cells, NS0 cells, SP2/0 cells, HEK293 cells, COS cells, yeast, or *E. coli* cells, and the antibody is recovered from the cells (from the supernatant or after cells lysis).

Recombinant production of antibodies is well-known in the state of the art and described, for example, in the review articles of Makrides, S.C., Protein Expr. Purif 17 (1999) 183-202; Geisse, S., et al., Protein Expr. Purif 8 (1996) 271-282; Kaufman, R. J., Mol. Biotechnol. 16 (2000) 151-161; Werner, R. G., Drug Res. 48 (1998) 870-880.

The antibodies may be present in whole cells, in a cell lysate, or in a partially purified, or substantially pure form. Purification is performed in order to eliminate other cellular components or other contaminants, e.g. other cellular nucleic acids or proteins, by standard techniques, including alkaline/SDS treatment, CsCl banding, column chromatography, agarose gel electrophoresis, and others well known in the art. See Ausubel, F., et al., ed. Current Protocols in Molecular Biology, Greene Publishing and Wiley Interscience, New York (1987).

Expression in NS0 cells is described by, e.g., Barnes, L. M., et al., Cytotechnology 32 (2000) 109-123; Barnes, L. M., et al., Biotech. Bioeng. 73 (2001) 261-270. Transient expression is described by, e.g., Durocher, Y., et al., Nucl. Acids. Res. 30 (2002) E9. Cloning of variable domains is described by Orlandi, R., et al., Proc. Natl. Acad. Sci. USA 86 (1989) 3833-3837; Carter, P., et al., Proc. Natl. Acad. Sci. USA 89 (1992) 4285-4289; Norderhaug, L., et al., J. Immunol. Methods 204 (1997) 77-87. A preferred transient expression system (HEK 293) is described by Schlaeger, E.-J. and Christensen, K., in Cytotechnology 30 (1999) 71-83, and by Schlaeger, E.-J., in J. Immunol. Methods 194 (1996) 191-199.

The heavy and light chain variable domains according to the invention are combined with sequences of promoter, translation initiation, constant region, 3' untranslated region, polyadenylation, and transcription termination to form expression vector constructs. The heavy and light chain expression constructs can be combined into a single vector, co-transfected, serially transfected, or separately transfected into host cells which are then fused to form a single host cell expressing both chains.

The control sequences that are suitable for prokaryotes, for example, include a promoter, optionally an operator sequence, and a ribosome binding site. Eukaryotic cells are known to utilize promoters, enhancers and polyadenylation signals.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading frame. However, enhancers do not have to be contiguous. Linking is accomplished by ligation at convenient restriction sites. If such sites do not exist, the synthetic oligonucleotide adaptors or linkers are used in accordance with conventional practice.

The monoclonal antibodies are suitably separated from the culture medium by conventional immunoglobulin purification procedures such as, for example, protein A-Sepharose, hydroxylapatite chromatography, gel electrophoresis, dialysis, or affinity chromatography. DNA and RNA encoding the monoclonal antibodies are readily isolated and sequenced using conventional procedures. The hybridoma cells can serve as a source of such DNA and RNA. Once isolated, the DNA may be inserted into expression vectors, which are then transfected into host cells such as HEK 293 cells, CHO cells, or myeloma cells that do not otherwise produce immunoglobulin protein, to obtain the synthesis of recombinant monoclonal antibodies in the host cells.

As used herein, the expressions "cell", "cell line", and "cell culture" are used interchangeably and all such designations include progeny. Thus, the words "transformants" and "transformed cells" include the primary subject cell and cultures derived therefrom without regard for the number of transfers. It is also understood that all progeny may not be precisely identical in DNA content, due to deliberate or inadvertent mutations. Variant progeny that have the same function or biological activity as screened for in the originally transformed cell are included.

Therapeutic Methods and Compositions

The invention comprises a method for the treatment of a patient in need of therapy, characterized by administering to the patient a therapeutically effective amount of the combination therapy of a PD-1-targeted IL-2 variant immunocytokine with an antibody which binds to human PD-L1 according to the invention.

The invention comprises the use of a PD-1-targeted IL-2 variant immunocytokine with an antibody which binds to human PD-L1 according to the invention for the described combination therapy.

One preferred embodiment of the invention is the combination therapy of a PD-1-targeted IL-2 variant immunocytokine with an antibody which binds to human PD-L1 of the present invention for use in the treatment of cancer or tumor.

Thus one embodiment of the invention is a PD-1-targeted IL-2 variant immunocytokine described herein for use in the treatment of cancer or tumor in combination with an anti-PD-L1 antibody as described herein.

Another embodiment of the invention is an anti-PD-L1 antibody described herein for use in the treatment of cancer of tumor in combination with a PD-1-targeted IL-2 variant immunocytokine as described herein.

The cancer or tumor may present an antigen in a tumor cell environment, e.g. on PD-1+ Tcells. PD-1 as the target of the combination therapy may be presented in the tumor cell environment, e.g. in PD-1+ T cells. The treatment may be of a solid tumor. The treatment may be of a carcinoma. The cancer may be selected from the group consisting of colorectal cancer, head and neck cancer, non-small cell lung cancer, breast cancer, pancreatic cancer, liver cancer and gastric cancer. The cancer may be selected from the group consisting of lung cancer, colon cancer, gastric cancer, breast cancer, head and neck cancer, skin cancer, liver cancer, kidney cancer, prostate cancer, pancreatic cancer, brain cancer and cancer of the skeletal muscle.

The term "cancer" as used herein may be, for example, lung cancer, non small cell lung (NSCL) cancer, bronchioloalviolar cell lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, gastric cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, cancer of the bladder, cancer of the kidney or ureter, renal cell carcinoma, carcinoma of the renal pelvis, mesothelioma, hepatocellular cancer, biliary cancer, neoplasms of the central nervous system (CNS), spinal axis tumors, brain stem glioma, glioblastoma multiforme, astrocytomas, schwanomas, ependymonas, medulloblastomas, meningiomas, squamous cell carcinomas, pituitary adenoma, lymphoma, lymphocytic leukemia, including refractory versions of any of the above cancers, or a combination of one or more of the above cancers. In one preferred embodiment such cancer is a breast cancer, colorectal cancer, melanoma, head and neck cancer, lung cancer or prostate cancer. In one preferred embodiment such cancer is a breast cancer, ovarian cancer, cervical cancer, lung cancer or prostate cancer. In another preferred embodiment such cancer is breast cancer, lung cancer, colon cancer, ovarian cancer, melanoma cancer, bladder cancer, renal cancer, kidney cancer, liver cancer, head and neck cancer, colorectal cancer, pancreatic cancer, gastric carcinoma cancer, esophageal cancer, mesothelioma, prostate cancer, leukemia, lymphoma, myelomas.

An embodiment of the invention is a PD-1-targeted IL-2 variant immunocytokine as described herein in combination with an anti-PD-L1 antibody as described herein for use in the treatment of any of the above described cancers or tumors.

Another embodiment of the invention is an anti-PD-L1 antibody as described herein in combination with a PD-1-targeted IL-2 variant immunocytokine as described herein for use in the treatment of any of the above described cancers or tumors.

The invention comprises the combination therapy with a PD-1-targeted IL-2 variant immunocytokine as described herein with an anti-PD-L1 antibody as described herein for the treatment of cancer.

The invention comprises the combination therapy with a PD-1-targeted IL-2 variant immunocytokine as described herein with an anti-PD-L1 antibody as described herein for the prevention or treatment of metastasis.

The invention comprises the combination therapy of a PD-1-targeted IL-2 variant immunocytokine as described herein with an anti-PD-L1 antibody as described herein for use in stimulating an immune response or function, such as T cell activity.

The invention comprises a method for the treatment of cancer in a patient in need thereof, characterized by administering to the patient a PD-1-targeted IL-2 variant immunocytokine as described herein and an anti-PD-L1 antibody as described herein.

The invention comprises a method for the prevention or treatment of metastasis in a patient in need thereof, characterized by administering to the patient a PD-1-targeted IL-2 variant immunocytokine as described herein and an anti-PD-L1 antibody being as described herein.

The invention comprises a method for stimulating an immune response or function, such as T cell activity, in a patient in need thereof, characterized by administering to the patient a PD-1-targeted IL-2 variant immunocytokine as described herein and an anti-PD-L1 antibody as described herein.

The invention comprises a PD-1-targeted IL-2 variant immunocytokine as described herein for use in the treatment of cancer in combination with an anti-PD-L1 antibody as described herein, or alternatively for the manufacture of a medicament for the treatment of cancer in combination with an anti-PD-L1 antibody as described herein.

The invention comprises a PD-1-targeted IL-2 variant immunocytokine as described herein for use in the prevention or treatment of metastasis in combination with an anti-PD-L1 antibody as described herein, or alternatively for the manufacture of a medicament for the prevention or treatment of metastasis in combination with an anti-PD-L1 antibody as described herein.

The invention comprises a PD-1-targeted IL-2 variant immunocytokine as described herein for use in stimulating an immune response or function, such as T cell activity, in combination with an anti-PD-L1 antibody as described herein, or alternatively for the manufacture of a medicament for use in stimulating an immune response or function, such as T cell activity, in combination with an anti-PD-L1 antibody as described herein.

The invention comprises an anti-PD-L1 antibody as described herein for use in the treatment of cancer in combination with a PD-1-targeted IL-2 variant immunocytokine as described herein, or alternatively for the manufacture of a medicament for the treatment of cancer in combination with a PD-1-targeted IL-2 variant immunocytokine as described herein.

The invention comprises an anti-PD-L1 antibody as described herein for use in the prevention or treatment of metastasis in combination with a PD-1-targeted IL-2 variant immunocytokine as described herein, or alternatively for the manufacture of a medicament for the prevention or treatment of metastasis in combination with a PD-1-targeted IL-2 variant immunocytokine as described herein.

The invention comprises an anti-PD-L1 antibody as described herein for use in stimulating an immune response or function, such as T cell activity, in combination with a PD-1-targeted IL-2 variant immunocytokine as described herein, or alternatively for the manufacture of a medicament for use in stimulating an immune response or function, such as T cell activity, in combination with a PD-1-targeted IL-2 variant immunocytokine as described herein.

In a preferred embodiment of the invention the PD-1-targeted IL-2 variant immunocytokine used in the above described combination treatments and medical uses of different diseases is a PD-1-targeted IL-2 variant immunocytokine characterized in comprising the polypeptide sequences of SEQ ID NO:7, SEQ ID NO:8 and SEQ ID NO:9, and the antibody which binds to human PD-L1 used in such combination treatments is characterized in comprising a heavy chain variable domain VH of SEQ ID NO:15 and a light chain variable domain VL of SEQ ID NO:16.

In a preferred embodiment of the invention the PD-1-targeted IL-2 variant immunocytokine used in the above described combination treatments and medical uses of different diseases is a PD-1-targeted IL-2 variant immunocytokine characterized in comprising the polypeptide sequences of SEQ ID NO:7, SEQ ID NO:8 and SEQ ID NO:9, and the antibody which binds to human PD-L1 used in such combination treatments is atezolizumab.

In another aspect, the present invention provides a composition, e.g. a pharmaceutical composition, containing a PD-1-targeted IL-2 variant immunocytokine as described herein and an antibody which binds to human PD-L1, or the antigen-binding portion thereof, as described herein formulated together with a pharmaceutically acceptable carrier.

As used herein, "pharmaceutically acceptable carrier" includes any and all solvents, dispersion media, coatings, antibacterial and antifungal agents, isotonic and absorption/resorption delaying agents, and the like that are physiologically compatible. Preferably, the carrier is suitable for injection or infusion.

A composition of the present invention can be administered by a variety of methods known in the art. As will be appreciated by the skilled artisan, the route and/or mode of administration will vary depending upon the desired results.

Pharmaceutically acceptable carriers include sterile aqueous solutions or dispersions and sterile powders for the preparation of sterile injectable solutions or dispersion. The use of such media and agents for pharmaceutically active substances is known in the art. In addition to water, the carrier can be, for example, an isotonic buffered saline solution.

Regardless of the route of administration selected, the compounds of the present invention, which may be used in a suitable hydrated form, and/or the pharmaceutical compositions of the present invention, are formulated into pharmaceutically acceptable dosage forms by conventional methods known to those of skill in the art.

Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient (effective amount). The selected dosage level will depend upon a variety of pharmacokinetic factors including the activity of the particular compositions of the present invention employed, or the ester, salt or amide thereof, the route of administration, the time of administration, the rate of excretion of the particular compound being employed, other drugs, compounds and/or materials used in combination with the particular compositions employed, the age, sex, weight, condition, general health and prior medical history of the patient being treated, and like factors well known in the medical arts.

In one aspect the invention provides a kit intended for the treatment of a disease, comprising in the same or in separate containers (a) a PD-1-targeted IL-2 variant immunocytokine as described herein, and (b) an antibody which binds to human PD-L1 as described herein, and optionally further comprising (c) a package insert comprising printed instructions directing the use of the combined treatment as a method for treating the disease. Moreover, the kit may comprise (a) a first container with a composition contained therein, wherein the composition comprises an antibody which binds to human PD-L1 as described herein; (b) a second container with a composition contained therein, wherein the composition comprises a PD-1-targeted IL-2 variant immunocytokine as described herein; and optionally (c) a third container with a composition contained therein, wherein the composition comprises a further cytotoxic or otherwise therapeutic agent. The kit in this embodiment of the invention may further comprise a package insert indicating that the compositions can be used to treat a particular condition. Alternatively, or additionally, the kit may further comprise a third (or fourth) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

In one aspect the invention provides a kit intended for the treatment of a disease, comprising (a) a container comprising a PD-1-targeted IL-2 variant immunocytokine as described herein, and (b) a package insert comprising instructions directing the use of the PD-1-targeted IL-2 variant immunocytokine in a combination therapy with an anti-PD-L1 antibody as described herein as a method for treating the disease.

In another aspect the invention provides a kit intended for the treatment of a disease, comprising (a) a container comprising an anti-PD-L1 antibody as described herein, and (b) a package insert comprising instructions directing the use of the anti-PD-L1 antibody in a combination therapy with PD-1-targeted IL-2 variant immunocytokine as described herein as a method for treating the disease.

In a further aspect the invention provides a medicament intended for the treatment of a disease, comprising a PD-1-targeted IL-2 variant immunocytokine as described herein, wherein said medicament is for use in a combination therapy with an antibody which binds to human PD-L1 as described herein and optionally comprises a package insert comprising printed instructions directing the use of the combined treatment as a method for treating the disease.

In still a further aspect the invention provides a medicament intended for the treatment of a disease, comprising an antibody which binds to human PD-L1 as described herein, wherein said medicament is for use in a combination therapy with a PD-1-targeted IL-2 variant immunocytokine as described herein and optionally comprises a package insert comprising printed instructions directing the use of the combined treatment as a method for treating the disease.

The term "a method of treating" or its equivalent, when applied to, for example, cancer refers to a procedure or course of action that is designed to reduce or eliminate the number of cancer cells in a patient, or to alleviate the symptoms of a cancer. "A method of treating" cancer or another proliferative disorder does not necessarily mean that the cancer cells or other disorder will, in fact, be eliminated, that the number of cells or disorder will, in fact, be reduced, or that the symptoms of a cancer or other disorder will, in fact, be alleviated. Often, a method of treating cancer will be performed even with a low likelihood of success, but which, given the medical history and estimated survival expectancy of a patient, is nevertheless deemed to induce an overall beneficial course of action.

The terms "administered in combination with" or "co-administration", "co-administering", "combination therapy" or "combination treatment" refer to the administration of the PD-1-targeted IL-2 variant immunocytokine as described herein and the antibody which binds to human PD-L1 as described herein e.g. as separate formulations/applications (or as one single formulation/application). The co-administration can be simultaneous or sequential in either order, wherein preferably there is a time period while both (or all) active agents simultaneously exert their biological activities. Said active agents are co-administered either simultaneously or sequentially (e.g. intravenous (i.v.) through a continuous infusion. When both therapeutic agents are co-administered sequentially the dose is administered either on the same day in two separate administrations, or one of the agents is administered on day 1 and the second is co-administered on day 2 to day 7, preferably on day 2 to 4. Thus in one embodiment the term "sequentially" means within 7 days after the dose of the first component, preferably within 4 days after the dose of the first component; and the term "simultaneously" means at the same time. The term "co-administration" with respect to the maintenance doses of PD-1-targeted IL-2 variant immunocytokine and/or anti-PD-L1 antibody means that the maintenance doses can be either co-administered simultaneously, if the treatment cycle is appropriate for both drugs, e.g. every week. Or the maintenance doses are co-administered sequentially, for example, doses of PD-1-targeted IL-2 variant immunocytokine and anti-PD-L1 antibody are given on alternate weeks.

It is self-evident that the antibodies are administered to the patient in a "therapeutically effective amount" (or simply "effective amount") which is the amount of the respective compound or combination that will elicit the biological or medical response of a tissue, system, animal or human that is being sought by the researcher, veterinarian, medical doctor or other clinician.

The amount of co-administration and the timing of co-administration will depend on the type (species, gender, age, weight, etc.) and condition of the patient being treated and the severity of the disease or condition being treated. Said PD-1-targeted IL-2 variant immunocytokine and/or anti-PD-L1 antibody are suitably co-administered to the patient at one time or over a series of treatments e.g. on the same day or on the day after or at weekly intervals.

In addition to the PD-1-targeted IL-2 variant immunocytokine in combination with the anti-PD-L1 antibody also a chemotherapeutic agent can be administered.

In one embodiment such additional chemotherapeutic agents, which may be administered with PD-1-targeted IL-2 variant immunocytokine as described herein and the anti-PD-L1 antibody as described herein, include, but are not limited to, anti-neoplastic agents including alkylating agents including: nitrogen mustards, such as mechlorethamine, cyclophosphamide, ifosfamide, melphalan and chlorambucil; nitrosoureas, such as carmustine (BCNU), lomustine (CCNU), and semustine (methyl-CCNU); Temodal™ (temozolamide), ethylenimines/methylmelamine such as triethylenemelamine (TEM), triethylene, thiophosphoramide (thiotepa), hexamethylmelamine (HMM, altretamine); alkyl sulfonates such as busulfan; triazines such as dacarbazine (DTIC); antimetabolites including folic acid analogs such as methotrexate and trimetrexate, pyrimidine analogs such as 5-fluorouracil (5FU), fluorodeoxyuridine, gemcitabine, cytosine arabinoside (AraC, cytarabine), 5-azacytidine, 2,2'-difluorodeoxycytidine, purine analogs such as 6-mercaptopurine, 6-thioguamne, azathioprine, T-deoxycoformycin (pentostatin), erythrohydroxynonyladenine (EHNA), fludarabine phosphate, and 2-chlorodeoxyadenosine (cladribine, 2-CdA); natural products including antimitotic drugs such as paclitaxel, *vinca* alkaloids including vinblastine (VLB), vincristine, and vinorelbine, taxotere, estramustine, and estramustine phosphate; pipodophylotoxins such as etoposide and teniposide; antibiotics such as actinomycin D, daunomycin (rubidomycin), doxorubicin, mitoxantrone, idarubicin, bleomycins, plicamycin (mithramycin), mitomycin C, and actinomycin; enzymes such as L-asparaginase; biological response modifiers such as interferon-alpha, IL-2, G-CSF and GM-CSF; miscellaneous agents including platinum coordination complexes such as oxaliplatin, cisplatin and carboplatin, anthracenediones such as mitoxantrone, substituted urea such as hydroxyurea, methylhydrazine derivatives including N-methylhydrazine (MIH) and procarbazine, adrenocortical suppressants such as mitotane (o, p-DDD) and aminoglutethimide; hormones and antagonists including adrenocorticosteroid antagonists such as prednisone and equivalents, dexamethasone and aminoglutethimide; Gemzar™ (gemcitabine), progestin such as hydroxyprogesterone caproate, medroxyprogesterone acetate and megestrol acetate; estrogen such as diethylstilbestrol and ethinyl estradiol equivalents; antiestrogen such as tamoxifen; androgens including testosterone propionate and fluoxymesterone/equivalents; antiandrogens such as flutamide, gonadotropin-releasing hormone analogs and leuprolide; and non-steroidal antiandrogens such as flutamide. Therapies targeting epigenetic mechanism including, but not limited to, histone deacetylase inhibitors, demethylating agents (e.g., Vidaza) and release of transcriptional repression (ATRA) therapies can also be combined with the antigen binding proteins. In one embodiment the chemotherapeutic agent is selected from the group consisting of taxanes (like e.g. paclitaxel (Taxol), docetaxel (Taxotere), modified paclitaxel (e.g., Abraxane and Opaxio), doxorubicin, sunitinib (Sutent), sorafenib (Nexavar), and other multikinase inhibitors, oxaliplatin, cisplatin and carboplatin, etoposide, gemcitabine, and vinblastine. In one embodiment the chemotherapeutic agent is selected from the group consisting of taxanes (like e.g. taxol (paclitaxel), docetaxel (Taxotere), modified paclitaxel (e.g. Abraxane and Opaxio). In one embodiment, the additional chemotherapeutic agent is selected from 5-fluorouracil (5-FU), leucovorin, irinotecan, or oxaliplatin. In one embodiment the chemotherapeutic agent is 5-fluorouracil, leucovorin and irinotecan (FOLFIRI). In one embodiment the chemotherapeutic agent is 5-fluorouracil, and oxaliplatin (FOLFOX).

Specific examples of combination therapies with additional chemotherapeutic agents include, for instance, therapies taxanes (e.g., docetaxel or paclitaxel) or a modified paclitaxel (e.g., Abraxane or Opaxio), doxorubicin), capecitabine and/or bevacizumab (Avastin) for the treatment of breast cancer; therapies with carboplatin, oxaliplatin, cisplatin, paclitaxel, doxorubicin (or modified doxorubicin (Caelyx or Doxil)), or topotecan (Hycamtin) for ovarian cancer, the therapies with a multi-kinase inhibitor, MM, (Sutent, Nexavar, or 706) and/or doxorubicin for treatment of kidney cancer; therapies with oxaliplatin, cisplatin and/or radiation for the treatment of squamous cell carcinoma; therapies with taxol and/or carboplatin for the treatment of lung cancer.

Therefore, in one embodiment the additional chemotherapeutic agent is selected from the group of taxanes (docetaxel or paclitaxel or a modified paclitaxel (Abraxane or Opaxio), doxorubicin, capecitabine and/or bevacizumab for the treatment of breast cancer.

In one embodiment the PD-1-targeted IL-2 variant immunocytokine/PD-L1 antibody combination therapy is one in which no chemotherapeutic agents are administered.

The invention comprises also a method for the treatment of a patient suffering from such disease as described herein.

The invention further provides a method for the manufacture of a pharmaceutical composition comprising an effective amount of a PD-1-targeted IL-2 variant immunocytokine according to the invention as described herein and an anti-PD-L1 antibody according to the invention as described herein together with a pharmaceutically acceptable carrier and the use of the PD-1-targeted IL-2 variant immunocytokine and anti-PD-L1 antibody according to the invention as described herein for such a method.

The invention further provides the use of a PD-1-targeted IL-2 variant immunocytokine according to the invention as described herein and an anti-PD-L1 antibody according to the invention as described herein in an effective amount for the manufacture of a pharmaceutical agent, preferably together with a pharmaceutically acceptable carrier, for the treatment of a patient suffering from cancer.

Cell Therapy

In some embodiments, the immunotherapy is an activation immunotherapy. In some embodiments, immunotherapy is provided as a cancer treatment. In some embodiments, immunotherapy comprises adoptive cell transfer.

In some embodiments, adoptive cell transfer comprises administration of a chimeric antigen receptor-expressing T-cell (CAR T-cell). A skilled artisan would appreciate that CARs are a type of antigen-targeted receptor composed of intracellular T-cell signaling domains fused to extracellular tumor-binding moieties, most commonly single-chain variable fragments (scFvs) from monoclonal antibodies.

CARs directly recognize cell surface antigens, independent of MHC-mediated presentation, permitting the use of a single receptor construct specific for any given antigen in all patients. Initial CARs fused antigen-recognition domains to the CD3 activation chain of the T-cell receptor (TCR) complex. While these first-generation CARs induced T-cell effector function in vitro, they were largely limited by poor antitumor efficacy in vivo. Subsequent CAR iterations have included secondary costimulatory signals in tandem with CD3, including intracellular domains from CD28 or a variety of TNF receptor family molecules such as 4-1BB (CD137) and OX40 (CD134). Further, third generation receptors include two costimulatory signals in addition to CD3, most commonly from CD28 and 4-1BB. Second and third generation CARs dramatically improve antitumor efficacy, in some cases inducing complete remissions in patients with advanced cancer. In one embodiment, a CAR T-cell is an immunoresponsive cell modified to express CARs, which is activated when CARs bind to its antigen.

In one embodiment, a CAR T-cell is an immunoresponsive cell comprising an antigen receptor, which is activated when its receptor binds to its antigen. In one embodiment, the CAR T-cells used in the compositions and methods as disclosed herein are first generation CAR T-cells. In another embodiment, the CAR T-cells used in the compositions and methods as disclosed herein are second generation CAR T-cells. In another embodiment, the CAR T-cells used in the compositions and methods as disclosed herein are third generation CAR T-cells. In another embodiment, the CAR T-cells used in the compositions and methods as disclosed herein are fourth generation CAR T-cells.

In some embodiments, adoptive cell transfer comprises administering T-cell receptor (TCR) modified T-cells. A skilled artisan would appreciate that TCR modified T-cells are manufactured by isolating T-cells from tumor tissue and isolating their TCRa and TCRβ chains. These TCRa and TCRβ are later cloned and transfected into T cells isolated from peripheral blood, which then express TCRa and TCRβ from T-cells recognizing the tumor.

In some embodiments, adoptive cell transfer comprises administering tumor infiltrating lymphocytes (TIL). In some embodiments, adoptive cell transfer comprises administering chimeric antigen receptor (CAR)-modified NK cells. A skilled artisan would appreciate that CAR-modified NK cells comprise NK cells isolated from the patient or commercially available NK engineered to express a CAR that recognizes a tumor-specific protein.

In some embodiments, adoptive cell transfer comprises administering dendritic cells.

In some embodiments, immunotherapy comprises administering of a cancer vaccine. A skilled artisan would appreciate that a cancer vaccine exposes the immune system to a cancer-specific antigen and an adjuvant. In some embodiments, the cancer vaccine is selected from a group comprising: sipuleucel-T, GVAX, ADXS11-001, ADXS31-001, ADXS31-164, ALVAC-CEA vaccine, AC Vaccine, talimogene laherparepvec, BiovaxID, Prostvac, CDX110, CDX1307, CDX1401, CimaVax-EGF, CV9104, DNDN, NeuVax, Ae-37, GRNVAC, tarmogens, GI-4000, GI-6207, GI-6301, ImPACT Therapy, IMA901, hepcortespenlisimut-L, Stimuvax, DCVax-L, DCVax-Direct, DCVax Prostate, CBLI, Cvac, RGSH4K, SCIB1, NCT01758328, and PVX-410.

The following examples, sequence listing and figures are provided to aid the understanding of the present invention, the true scope of which is set forth in the appended claims. It is understood that modifications can be made in the procedures set forth without departing from the spirit of the invention.

In the Following Statements, Embodiments of the Invention are Described:

1. A) A PD-1-targeted IL-2 variant immunocytokine in combination with an antibody which binds to human PD-L1 for use in the treatment of cancer, in the prevention or treatment of metastasis, or in stimulating an immune response or function, such as T cell activity; or B) use of a PD-1-targeted IL-2 variant immunocytokine for the manufacture of a medicament for use in the treatment of cancer, in the prevention or treatment of metastasis, or in stimulating an immune response or function, such as T cell activity;

or

C) a PD-1-targeted IL-2 variant immunocytokine for use in the treatment of cancer, in the prevention or treatment of metastasis, or in stimulating an immune response or function, such as T cell activity;

wherein the PD-1-targeted IL-2 variant immunocytokine is administered in combination with an antibody which binds to human PD-L1;

wherein the PD-1-targeted IL-2 variant immunocytokine used in the combination therapy is characterized in comprising a) a heavy chain variable domain VH of SEQ ID NO:5 and a light chain variable domain VL of SEQ ID NO:6, and the polypeptide sequence of SEQ ID NO:2, or b) a polypeptide sequence of SEQ ID NO:7 or SEQ ID NO:8 or SEQ ID NO:9, or c) the polypeptide sequences of SEQ ID NO:7, and SEQ ID NO:8 and SEQ ID NO:9, or d) the polypeptide sequences of SEQ ID NO:12, and SEQ ID NO:13 and SEQ ID NO:14, and the antibody which binds to human PD-L1 used in the combination therapy is characterized in comprising a) a heavy chain variable domain VH of SEQ ID NO:15 and a light chain variable domain VL of SEQ ID NO:16, or b) a heavy chain variable domain VH of SEQ ID NO:19 and a light chain variable domain VL of SEQ ID NO:20

2. The PD-1-targeted IL-2 variant immunocytokine in combination with an antibody which binds to human PD-L1 or use according any one of the preceding embodiments, wherein the PD-1-targeted IL-2 variant immunocytokine used in the combination therapy is characterized in comprising the polypeptide sequences of SEQ ID NO:7, SEQ ID NO:8 and SEQ ID NO:9, and wherein the antibody which binds to human PD-L1 used in the combination therapy is characterized in comprising a heavy chain variable domain VH of SEQ ID NO:15 and a light chain variable domain VL of SEQ ID NO:16.

3. The PD-1-targeted IL-2 variant immunocytokine in combination with an antibody which binds to human PD-L1 or use according any one of the preceding embodiments, wherein the PD-1-targeted IL-2 variant immunocytokine used in the combination therapy is characterized in comprising the polypeptide sequences of SEQ ID NO:7, SEQ ID NO:8 and SEQ ID NO:9, and wherein the antibody which binds to human PD-L1 used in the combination therapy is atezolizumab.

4. The PD-1-targeted IL-2 variant immunocytokine in combination with an antibody which binds to human PD-L1 or use according any one of the preceding embodiments, characterized in that the antibody component of the immunocytokine and the antibody are of human IgG1 subclass or human IgG4 subclass.

5. The PD-1-targeted IL-2 variant immunocytokine in combination with an antibody which binds to human PD-L1 or use according to any one of the preceding embodiments, characterized in that said antibodies have reduced or minimal effector function.

6. The PD-1-targeted IL-2 variant immunocytokine in combination with an antibody which binds to human PD-L1 or use according to any one of the preceding embodiments, wherein the minimal effector function results from an effector less Fc mutation.

7. The PD-1-targeted IL-2 variant immunocytokine in combination with an antibody which binds to human PD-L1 or use according to any one of the preceding embodiments, wherein the effector less Fc mutation is L234A/L235A or L234A/L235A/P329G or N297A or D265A/N297A (EU numbering).

8. A) A method for the treatment of cancer, the prevention or treatment of metastasis, or stimulating an immune response or function, such as T cell activity, wherein PD-1 is presented in a tumor cell environment;

wherein a PD-1-targeted IL-2 variant immunocytokine is administered in combination with an antibody which binds to human PD-L1, or B) a method of treatment of a patient having a tumor, wherein PD-1 is presented in a tumor cell environment, wherein a PD-1-targeted IL-2 variant immunocytokine is administered in combination with an antibody which binds to human PD-L1;

wherein the PD-1-targeted IL-2 variant immunocytokine used in the combination therapy is characterized in comprising a) a heavy chain variable domain VH of SEQ ID NO:5 and a light chain variable domain VL of SEQ ID NO:6, and the polypeptide sequence of SEQ ID NO:2, or b) a polypeptide sequence of SEQ ID NO:7 or SEQ ID NO:8 or SEQ ID NO:9, or c) the polypeptide sequences of SEQ ID NO:7, and SEQ ID NO:8 and SEQ ID NO:9, or d) the polypeptide sequences of SEQ ID NO:12, and SEQ ID NO:13 and SEQ ID NO:14;

and the antibody which binds to human PD-L1 used in the combination therapy is characterized in comprising a) a heavy chain variable domain VH of SEQ ID NO:15 and a light chain variable domain VL of SEQ ID NO:16, or b) a heavy chain variable domain VH of SEQ ID NO:19 and a light chain variable domain VL of SEQ ID NO:20.

9. A method for the treatment of cancer in a patient in need thereof, for the prevention or treatment of metastasis in a patient in need thereof, or for stimulating an immune response or function, such as T cell activity, in a patient in need thereof, comprising administering to the patient a PD-1-targeted IL-2 variant immunocytokine and an anti-PD-L1 antibody, wherein the PD-1-targeted IL-2 variant immunocytokine used in the combination therapy is characterized in comprising a) a heavy chain variable domain VH of SEQ ID NO:5 and a light chain variable domain VL of SEQ ID NO:6, and the polypeptide sequence of SEQ ID NO:2, or b) a polypeptide sequence of SEQ ID NO:7 or SEQ ID NO:8 or SEQ ID NO:9, or c) the polypeptide sequences of SEQ ID NO:7, and SEQ ID NO:8 and SEQ ID NO:9, or d) the polypeptide sequences of SEQ ID NO:12, and SEQ ID NO:13 and SEQ ID NO:14;

and the antibody which binds to human PD-L1 used in the combination therapy is characterized in comprising a) a heavy chain variable domain VH of SEQ ID NO:15 and a light chain variable domain VL of SEQ ID NO:16, or b) a heavy chain variable domain VH of SEQ ID NO:19 and a light chain variable domain VL of SEQ ID NO:20.

10. The method according to embodiment 9, for the treatment of cancer.

11. The method according to embodiment 10, for the treatment of breast cancer, lung cancer, colon cancer, ovarian cancer, melanoma cancer, bladder cancer, renal cancer, kidney cancer, liver cancer, head and neck cancer, colorectal cancer, melanoma, pancreatic cancer, gastric carcinoma cancer, esophageal cancer, mesothelioma, prostate cancer, leukemia, lymphomas, myelomas.

12. The method according any one of embodiments 8 to 11, wherein the PD-1-targeted IL-2 variant immunocytokine used in the combination therapy is characterized in comprising the polypeptide sequences of SEQ ID NO:7, SEQ ID NO:8 and SEQ ID NO:9, and wherein the antibody which binds to human PD-L1 used in the combination therapy is characterized in comprising a heavy chain variable domain VH of SEQ ID NO:15 and a light chain variable domain VL of SEQ ID NO:16.

13. The method according any one of embodiments 8 to 12, wherein the PD-1-targeted IL-2 variant immunocytokine used in the combination therapy is characterized in comprising the polypeptide sequences of SEQ ID NO:7, SEQ ID NO:8 and SEQ ID NO:9, and wherein the antibody which binds to human PD-L1 used in the combination therapy is atezolizumab.

14. The method according any one of embodiments 8 to 13, characterized in that the antibody component of the immunocytokine and the antibody are of human IgG1 subclass or human IgG4 subclass.

15. The method according any one of embodiments 8 to 14, characterized in that said antibodies have reduced or minimal effector function.

16. The method according any one of embodiments 8 to 15, wherein the minimal effector function results from an effector less Fc mutation.

17. The method according any one of embodiments 8 to 16, wherein the effector less Fc mutation is L234A/L235A or L234A/L235A/P329G or N297A or D265A/N297A (EU numbering).

18. The method according to any one of embodiments 8 to 17, wherein said PD-1-targeted IL-2 variant immunocytokine and antibody which binds to human PD-L1 are administered simultaneously or sequentially.

19. The method according of any one of embodiments 8 to 18, further comprising administering to said patient a chemotherapeutic agent.

20. A kit intended for the treatment of cancer in a patient in need thereof, for the prevention or treatment of metastasis in a patient in need thereof, or for stimulating an immune response or function, such as T cell activity, comprising in the same or in separate containers (a) a PD-1-targeted IL-2 variant immunocytokine, (b) an antibody which binds to human PD-L1, and (c) optionally a package insert comprising printed instructions directing the use of the PD-1-targeted IL-2 variant immunocytokine and the antibody which binds to human PD-L1 in a combined treatment,
    wherein the PD-1-targeted IL-2 variant immunocytokine used in the combination therapy is characterized in comprising
    a) a heavy chain variable domain VH of SEQ ID NO:5 and a light chain variable domain VL of SEQ ID NO:6, and the polypeptide sequence of SEQ ID NO:2, or
    b) a polypeptide sequence of SEQ ID NO:7 or SEQ ID NO:8 or SEQ ID NO:9, or
    c) the polypeptide sequences of SEQ ID NO:7, and SEQ ID NO:8 and SEQ ID NO:9, or
    d) the polypeptide sequences of SEQ ID NO:12, and SEQ ID NO:13 and SEQ ID NO:14;
    and the antibody which binds to human PD-L1 used in the combination therapy is characterized in comprising
    a) a heavy chain variable domain VH of SEQ ID NO:15 and a light chain variable domain VL of SEQ ID NO:16, or
    b) a heavy chain variable domain VH of SEQ ID NO:19 and a light chain variable domain VL of SEQ ID NO:20.

21. A kit intended for the treatment of cancer in a patient in need thereof, for the prevention or treatment of metastasis in a patient in need thereof, or for stimulating an immune response or function, such as T cell activity, comprising (a) a container comprising a PD-1-targeted IL-2 variant immunocytokine, and (b) a package insert comprising instructions directing the use of the PD-1-targeted IL-2 variant immunocytokine in a combination therapy with an antibody which binds to human PD-L1 as a method for treating the disease, wherein the PD-1-targeted IL-2 variant immunocytokine used in the combination therapy is characterized in comprising
    a) a heavy chain variable domain VH of SEQ ID NO:5 and a light chain variable domain VL of SEQ ID NO:6, and the polypeptide sequence of SEQ ID NO:2, or
    b) a polypeptide sequence of SEQ ID NO:7 or SEQ ID NO:8 or SEQ ID NO:9, or
    c) the polypeptide sequences of SEQ ID NO:7, and SEQ ID NO:8 and SEQ ID NO:9, or
    d) the polypeptide sequences of SEQ ID NO:12, and SEQ ID NO:13 and SEQ ID NO:14;
    and the antibody which binds to human PD-L1 used in the combination therapy is characterized in comprising
    a) a heavy chain variable domain VH of SEQ ID NO:15 and a light chain variable domain VL of SEQ ID NO:16, or
    b) a heavy chain variable domain VH of SEQ ID NO:19 and a light chain variable domain VL of SEQ ID NO:20.

22. A kit intended for the treatment of cancer in a patient in need thereof, for the prevention or treatment of metastasis in a patient in need thereof, or for stimulating an immune response or function, such as T cell activity, comprising (a) a container comprising an antibody which binds to human PD-L1, and (b) a package insert comprising instructions directing the use of the antibody which binds to human PD-L1 in a combination therapy with a PD-1-targeted IL-2 variant immunocytokine as a method for treating the disease,
    wherein the PD-1-targeted IL-2 variant immunocytokine used in the combination therapy is characterized in comprising
    a) a heavy chain variable domain VH of SEQ ID NO:5 and a light chain variable domain VL of SEQ ID NO:6, and the polypeptide sequence of SEQ ID NO:2, or
    b) a polypeptide sequence of SEQ ID NO:7 or SEQ ID NO:8 or SEQ ID NO:9, or
    c) the polypeptide sequences of SEQ ID NO:7, and SEQ ID NO:8 and SEQ ID NO:9, or
    d) the polypeptide sequences of SEQ ID NO:12, and SEQ ID NO:13 and SEQ ID NO:14;
    and the antibody which binds to human PD-L1 used in the combination therapy is characterized in comprising
    a) a heavy chain variable domain VH of SEQ ID NO:15 and a light chain variable domain VL of SEQ ID NO:16, or
    b) a heavy chain variable domain VH of SEQ ID NO:19 and a light chain variable domain VL of SEQ ID NO:20.

23. The kit according to embodiment 21 to 22, for the treatment of cancer.

24. The kit according to embodiment 23, for the treatment of breast cancer, lung cancer, colon cancer, ovarian cancer, melanoma cancer, bladder cancer, renal cancer, kidney cancer, liver cancer, head and neck cancer, colorectal cancer, melanoma, pancreatic cancer, gastric carcinoma cancer, esophageal cancer, mesothelioma, prostate cancer, leukemia, lymphomas, myelomas.

25. The kit according any one of embodiments 21 to 24, wherein the PD-1-targeted IL-2 variant immunocytokine used in the combination therapy is characterized in comprising the polypeptide sequences of SEQ ID NO:7, SEQ ID NO:8 and SEQ ID NO:9, and wherein the antibody which binds to human PD-L1 used in the combination therapy is characterized in comprising a heavy chain variable domain VH of SEQ ID NO:15 and a light chain variable domain VL of SEQ ID NO:16.

26. The kit according any one of embodiments 21 to 24, wherein the PD-1-targeted IL-2 variant immunocytokine used in the combination therapy is characterized in comprising the polypeptide sequences of SEQ ID NO:7, SEQ ID NO:8 and SEQ ID NO:9, and wherein the antibody which binds to human PD-L1 used in the combination therapy is atezolizumab.

27. The kit according any one of embodiments 21 to 26, characterized in that the antibody component of the immunocytokine and the antibody are of human IgG1 subclass or human IgG4 subclass.

28. The kit according any one of embodiments 21 to 27, characterized in that said antibodies have reduced or minimal effector function.

29. The kit according any one of embodiments 21 to 28, wherein the minimal effector function results from an effector less Fc mutation.
30. The kit according any one of embodiments 21 to 29, wherein the effector less Fc mutation is L234A/L235A or L234A/L235A/P329G or N297A or D265A/N297A (EU numbering).
31. A medicament intended for the treatment of cancer in a patient in need thereof, for the prevention or treatment of metastasis in a patient in need thereof, for the treatment of inflammatory diseases in a patient in need thereof, for treating or delaying progression of an immune related disease such as tumor immunity in a patient in need thereof, or for stimulating an immune response or function, such as T cell activity,
 comprising a PD-1-targeted IL-2 variant immunocytokine,
 wherein said medicament is for use in a combination therapy with an antibody which binds to human PD-L1, and optionally comprises a package insert comprising printed instructions directing the use of the PD-1-targeted IL-2 variant immunocytokine and the antibody which binds to human PD-L1 in a combined treatment,
 wherein the PD-1-targeted IL-2 variant immunocytokine used in the combination therapy is characterized in comprising
 a) a heavy chain variable domain VH of SEQ ID NO:5 and a light chain variable domain VL of SEQ ID NO:6, and the polypeptide sequence of SEQ ID NO:2, or
 b) a polypeptide sequence of SEQ ID NO:7 or SEQ ID NO:8 or SEQ ID NO:9, or
 c) the polypeptide sequences of SEQ ID NO:7, and SEQ ID NO:8 and SEQ ID NO:9, or
 d) the polypeptide sequences of SEQ ID NO:12, and SEQ ID NO:13 and SEQ ID NO:14;
 and the antibody which binds to human PD-L1 used in the combination therapy is characterized in comprising
 a) a heavy chain variable domain VH of SEQ ID NO:15 and a light chain variable domain VL of SEQ ID NO:16, or
 b) a heavy chain variable domain VH of SEQ ID NO:19 and a light chain variable domain VL of SEQ ID NO:20.
32. The medicament according to embodiment 31, for the treatment of cancer.
33. The medicament according to embodiment 32, for the treatment of breast cancer, lung cancer, colon cancer, ovarian cancer, melanoma cancer, bladder cancer, renal cancer, kidney cancer, liver cancer, head and neck cancer, colorectal cancer, melanoma, pancreatic cancer, gastric carcinoma cancer, esophageal cancer, mesothelioma, prostate cancer, leukemia, lymphomas, myelomas.
34. The medicament according any one of embodiments 31 to 33, wherein the PD-1-targeted IL-2 variant immunocytokine used in the combination therapy is characterized in comprising the polypeptide sequences of SEQ ID NO:7, SEQ ID NO:8 and SEQ ID NO:9, and wherein the antibody which binds to human PD-L1 used in the combination therapy is characterized in comprising a heavy chain variable domain VH of SEQ ID NO:15 and a light chain variable domain VL of SEQ ID NO:16.
35. The medicament according any one of embodiments 31 to 33, wherein the PD-1-targeted IL-2 variant immunocytokine used in the combination therapy is characterized in comprising the polypeptide sequences of SEQ ID NO:7, SEQ ID NO:8 and SEQ ID NO:9, and wherein the antibody which binds to human PD-L1 used in the combination therapy is atezolizumab.
36. The medicament according any one of embodiments 31 to 35, characterized in that the antibody component of the immunocytokine and the antibody are of human IgG1 subclass or human IgG4 subclass.
37. The medicament according any one of embodiments 31 to 36, characterized in that said antibodies have reduced or minimal effector function.
38. The medicament according any one of embodiments 31 to 37, wherein the minimal effector function results from an effector less Fc mutation.
39. The medicament according any one of embodiments 31 to 38, wherein the effector less Fc mutation is L234A/L235A or L234A/L235A/P329G or N297A or D265A/N297A (EU numbering).
40. The combinations for use or uses of a medicament or uses according to any of embodiments 1 to 39 comprising treatment with or pre-treatment with immunotherapy.
41. Embodiment 40, wherein said immunotherapy comprises adoptive cell transfer, administration of monoclonal antibodies, administration of cytokines, administration of a cancer vaccine, T cell engaging therapies, or any combination thereof
42. Embodiment 41, wherein the adoptive cell transfer comprises administering chimeric antigen receptor expressing T-cells (CAR T-cells), T-cell receptor (TCR) modified T-cells, tumor-infiltrating lymphocytes (TIL), chimeric antigen receptor (CAR)-modified natural killer cells, T cell receptor (TCR) transduced cells, or dendritic cells, or any combination thereof.

EXAMPLES

Murine surrogate PD-1-IL2v immunoconjugate was tested alone and in combination with murine surrogate PD-L1 Mab for their anti-tumoral efficacy in a syngeneic mouse model and a RT5 transgenic mouse model.

Materials

PD1-Il2v and muPD1-IL2v

The expression cassette for the antibody heavy chain—interleukin-2 (IL-2) fusion protein [heavy chain variable region of anti-human PD-1 antibody, human IgG1 heavy chain (bearing mutations L234A, L235A and P329G (EU numbering) for removal of effector functions, and mutations S354C and T366W (EU numbering) for heterodimerization ("knob")), (G4S)3 linker, and human IL-2v (bearing the mutations T3A, F42A, Y45A, L72G and C125A)], the expression cassette for the antibody heavy chain [heavy chain variable region of anti-human PD-1 antibody, and human IgG1 heavy chain (bearing mutations L234A, L235A and P329G (EU numbering) for removal of effector functions, mutations Y349C, T366S, L368A and Y410V (EU numbering) for heterodimerization ("hole"), and optionally mutations H435R and Y436F (EU numbering)] and the expression cassette for the antibody light chain [light chain variable region of anti-human PD-1 antibody, and human Ckappa constant region] and was produced by gene-synthesis.

They were each cloned via HindIII and NheI digestion into an expression vector under the control of the CMVpromoter followed by IntronA and terminated by BGH-poly A signal. The vector further contained a bacterial ampicillin resistance gene and an origin of replication from *E. coli.*

The human PD1-IL-2v fusion protein (SEQ ID NOs 7, 8 and 9) was generated by cotransfection of HEK293F cells (Invitrogen) with the above-described vectors in the ratio of 1:1:1 in shaking flasks. After one week supernatant was harvested and filtrated through sterile filters.

The fusion protein was purified from the supernatant by a combination of Protein A affinity chromatography and size exclusion chromatography. The obtained product was characterized for identity by mass spectrometry and analytical properties such as purity by capillary electrophoresis (CE-SDS), monomer content and stability.

The murine surrogate PD1-IL2v fusion protein (SEQ ID NOs 12, 13 and 14) was produced analogously. The surrogate molecule comprises a murine IgG1 anti-mouse PD-1 antibody (bearing Fc mutations for removal of effector function and for heterodimerization) and murine interleukin-2 with analogous mutations to the human molecule.

Both fusion proteins could be produced in good yields and are stable.

Human/mouse crossreactive anti-PD-L1 antibodies were used in the studies. For example, an anti-mouse PD-L1 surrogate antibody based on the YW243.55.S70 PD-L1 antibody described in WO 2010/077634 (sequence shown in FIG. 11), termed YW243.55.570 PD-L1 muIgG1, was generated for use in vivo tumor models. This antibody contained a DAPG mutation to abolish FcγR interaction. The variable region of YW243.55.S70 was attached to a murine IgG1 constant domain with DAPG Fc mutations.

The polypeptide sequences of YW243.55.570 PD-L1 muIgG1 are as follows:

```
YW243.55.S70 PD-L1 muIgG1 DAPG HC (SEQ ID NO:21):
EVOLVESGGGLVQPGGSLRLSCAASGFTFSDSWIHWVRQAPGKGLEWVA

WISPYGGSTYYADSVKGRFTISADTSKNTAYLQMNSLRAEDTAVYYCAR

RHWPGGFDYWGQGTLVTVSAAKTTPPSVYPLAPGSAAQTNSMVTLGCLV

KGYFPEPVTVTWNSGSLSSGVHTFPAVLQSDLYTLSSSVTVPSSTWPSE

TVTCNVAHPASSTKVDKKIVPRDCGCKPCICTVPEVSSVFIFPPKPKDV

LTITLTPKVTCVVVDISKDAPEVQFSWFVDDVEVHTAQTQPREEQFNST

FRSVSELPIMHQDWLNGKEFKCRVNSAAFGAPIEKTISKTKGRPKAPQV

YTIPPPKEQMAKDKVSLTCMITDFFPEDITVEWQWNGQPAENYKNTQPI

MDTDGSYFVYSKLNVQKSNWEAGNTFTCSVLHEGLHNHHTEKSLSHSPG

K
```

```
YW243.55.S70 PD-L1 muIgG1 LC (SEQ ID NO:22):
DIQMTQSPSSLSASVGDRVTITCRASQDVSTAVAWYQQKPGKAPKLLIY

SASFLYSGVPSRFSGSGSGTDFTLTISSLQPEDFATYYCQQYLYHPATF

GQGTKVEIKRADAAPTVSIFPPSSEQLTSGGASVVCFLNNFYPKDINVK

WKIDGSERQNGVLNSWTDQDSKDSTYSMSSTLTLTKDEYERHNSYTCEA

THKTSTSPIVKSFNRNEC
```

Example 1

MC38 Colorectal Subcutaneous Syngeneic Model

The murine surrogate PD1-IL2v immunoconjugate (muPD1-IL2v: SEQ ID NOs 12, 13, 14) was tested in the mouse colorectal MC38 cell line subcutaneously injected into Black 6 mice. The anti-PD-L1 antibody PD-L1 6E11 muIgG1 was used in this study (SEQ ID NOs 21, 22).

The MC38 colorectal carcinoma tumor cell line was routinely cultured in DMEM containing 10% FCS (Gibco) at 37° C. in a water-saturated atmosphere at 5% CO2. Passage 11 was used for transplantation, at a viability of 91%. $5\times10^5$ cells per animal were injected subcutaneously in 100 μl of RPMI cell culture medium (Gibco) into the flank of mice using a 1 ml tuberculin syringe (BD Biosciences).

Female Black 6, aged 6-8 weeks at the start of the experiment (Charles Rivers, Lyon, France) were maintained under specific-pathogen-free condition with daily cycles of 12 h light/12 h darkness according to committed guidelines (GV-Solas; Felasa; TierschG). After arrival, animals were maintained for one week to get accustomed to the new environment and for observation. Continuous health monitoring was carried out on a regular basis.

Mice were injected subcutaneously on study day 0 with $5\times10^5$ of MC38 cells, randomized and weighed. One week after the tumor cell injection (tumor volume>150 mm$^3$), mice were injected i.v. with muPD1-IL2v, muPD-L1-Mab or the combination of muPD1-IL2v+muPD-L1 Mab for two weeks. All mice were injected i.v. with 200 μl of the appropriate solution. The mice in the Vehicle group were injected with Histidine Buffer and the treatment groups with the muPD1-IL2v construct 0.5 mg/kg qw or the muPD-L1 Mab 10 mg/kg iv once and 5 mg/kg 2qw thereafter or the combination muPD1-IL-2v+muPD-L1 Mab. To obtain the proper amount of immunoconjugate per 200 μl, the stock solutions were diluted with Histidine Buffer when necessary.

FIG. 1 and Table 1A show that the combination muPD-IL2v and muPD-L1 Mab mediated superior efficacy in terms of tumor growth inhibition compared to muPD1-IL2v and muPD-L1 Mab alone.

TABLE 1A

| Groups | Tumor growth inhibition day 17 (%) | p-value (Dunnett's method) |
|---|---|---|
| muPD-L1 Mab | 37 | 0.2149 |
| muPD1-IL2v | 48 | 0.1092 |
| muPD1-IL2v + muPD-L1 Mab | 83 | 0.0026** |

TABLE 1B

| Compound | Dose/ mouse | Formulation buffer | Concentration (mg/mL) |
|---|---|---|---|
| muPD1-IL2v | 10 μg | 20 mM Histidine, 140 mM NaCl; pH 6.0 | 3.63 (=stock solution) |
| PD-L1 6E11 muIgG1 | 200 μg and 100 μg | 20 mM Histidine, 140 mM NaCl, pH 6.0 | 27.1 (=stock solution) |

Example 2

Rip-Tag5 (RT5) Transgenic Mouse Model of PanNET

Methods

Rip-Tag5 (RT5) transgenic mouse model of PanNET. The generation of Rip-Tag5 mice has been previously described (J Clin Invest. 1996; 97(1):54-64. https://doi.org/10.1172/JCI118406). The Rip-Tag5 mice in this study were on a C57B6/N background. Animal experiments were conducted under the approved licenses VD3133 and VD3475.

Preclinical drug trial in RT5 mice. To enroll Rip-Tag5 mice into the trial, mice at 22 weeks of age were screened for the presence of PanNET by ultrasound imaging using a Vevo2100 system with a MS550D 40 MHz transducer (Visual Sonic). Rip-Tag5 were randomly assigned to the different treatment groups based on the cumulative tumor burden. For the long term studies tumors were monitored every two weeks.

Drugs and dosing regimen. All drugs used in Example 2 were murine surrogate molecules, although not explicitly stated herein. The murine anti-PD-L1 antibodies "6E11 binder muIgG2a (PGLALA)" abbreviated as 6E11-muIgG2a, "6E11 binder muIgG1 (DAPG)" abbreviated as 6E11-muIgG1 and "YW243.55.S70 binder muIgG1 (DAPG)" abbreviated as S70-muIgG1 were used.

In the anti-PD-L1 treatment of four Rip-Tag5 mice resulting in FIG. 3D the murine anti-PD-L1 antibodies were administered according to table 2.

TABLE 2

| Mouse ID | Week 1 | Week 2 | Week 3 | Week 4 | Week 5 | Week 6 | Week 7 | Week 8 |
|---|---|---|---|---|---|---|---|---|
| DHA-EE6562 | 6E11-muIgG2a | 6E11-muIgG2a | 6E11-muIgG2a | 6E11-muIgG1 | 6E11-muIgG1 | 6E11-muIgG1 | 6E11-muIgG1 | S70-muIgG1 |
| DHA-7EE185 | 6E11-muIgG2a | 6E11-muIgG2a | — | — | — | — | — | — |
| DHA-EE7181 | 6E11-muIgG1 | 6E11-muIgG1 | 6E11-muIgG1 | S70-muIgG1 | S70-muIgG1 | S70-muIgG1 | S70-muIgG1 | — |
| DHA-EE7431 | 6E11-muIgG1 | 6E11-muIgG1 | S70-muIgG1 | S70-muIgG1 | S70-muIgG1 | S70-muIgG1 | — | — |

In the combination treatment of PD1-IL2v and anti-PD-L1 of seven Rip-Tag5 mice resulting in FIG. 3E the murine anti-PD-L1 antibodies were administered according to table 3.

TABLE 3

| Mouse ID | Week 1 | Week 2 | Week 3 | Week 4 | Week 5 | Week 6 | Week 7 | Week 8 |
|---|---|---|---|---|---|---|---|---|
| DHA-EE5456 | 6E11-muIgG2a | 6E11-muIgG2a | 6E11-muIgG2a | 6E11-muIgG2a | 6E11-muIgG1 | 6E11-muIgG1 | 6E11-muIgG1 | S70-muIgG1 |
| DHA-6558 | 6E11-muIgG2a | 6E11-muIgG2a | 6E11-muIgG2a | 6E11-muIgG2a | 6E11-muIgG1 | 6E11-muIgG1 | 6E11-muIgG1 | S70-muIgG1 |
| DHA-6000 | 6E11-muIgG2a | 6E11-muIgG2a | 6E11-muIgG2a | 6E11-muIgG1 | 6E11-muIgG1 | 6E11-muIgG1 | S70-muIgG1 | S70-muIgG1 |
| DHA-6001 | 6E11-muIgG2a | 6E11-muIgG2a | 6E11-muIgG1 | 6E11-muIgG1 | 6E11-muIgG1 | S70-muIgG1 | S70-muIgG1 | S70-muIgG1 |
| DHA-6003 | 6E11-muIgG2a | 6E11-muIgG1 | 6E11-muIgG1 | 6E11-muIgG1 | S70-muIgG1 | S70-muIgG1 | S70-muIgG1 | S70-muIgG1 |
| DHA-6005 | 6E11-muIgG1 | 6E11-muIgG1 | 6E11-muIgG1 | 6E11-muIgG1 | S70-muIgG1 | S70-muIgG1 | S70-muIgG1 | S70-muIgG1 |
| DHA-7449 | 6E11-muIgG1 | 6E11-muIgG1 | 6E11-muIgG1 | 6E11-muIgG1 | S70-muIgG1 | S70-muIgG1 | S70-muIgG1 | S70-muIgG1 |

Drugs were administered by i.p. injection with the following amounts per mouse: anti-PD1-low: 22.75 μg, q1wk (equimolar to PD1-IL2v), anti-PD1-high: 250 μg, q1wk (therapeutic dose), DP47-IL2v: 25 μg, q1wk, PD1-IL2v: 25 μg, q1wk, anti-PDL1: first dose 250 μg, followed by 125 μg, twice a week, for a duration of eight weeks.

Flow cytometry. Single cell suspensions of spleens were generated by mashing the spleen through a 40 μm cell strainer. After lysing red blood cells with PD PharmLyse buffer (BD Biosciences 555899), splenocytes were blocked with anti-mouse CD16/32 (BioLegend, cat number 101302). Live/dead staining was performed with fixable viability stain 780 (BD 565388). TAG-specific $CD8^+$ T cells were stained with SV40 TAG multimer (APC-MHC-H2Kb-VVYD-FLKC, University of Lausanne), followed by staining of antibodies against surface antigens. Intracellular proteins were stained after fixation and permeabilization using the Foxp3 staining kit (Invitrogen, cat number 00-5523-00) according to the instruction of the manufacturer. The panel consisted of the following antibodies: CD4-BV510 (BioLegend, cat number 100553), CD8-BB515 (BD Biosciences, cat number 564422), PD1-PE-Cy7 (BioLegend, cat number 109110), LAG3-BV421 (BioLegend, cat number 125221), TIGIT-PE-Dazzle 594 (BioLegend, cat number 142109), CD28-BB700 (BD Biosciences, cat number 566513), ICOS-BV785 (BioLegend, cat number 313534), KLRG1-BV711 (BioLegend, cat number 138427), CD25-APC-R700 (BD Biosciences, cat number 565135), CD127-BV650 (BioLegend, cat number 135043), CD27-BUV395 (BD Biosciences, cat number 740247), Foxp3-PE (Invitrogen, cat number 12-5773-82). Samples were analyzed on a BD LSR Fortessa flow cytometer and the data was processed with the FlowJo software and GraphPad Prism.

Immunohistochemistry. Tumors were embedded in OCT and frozen on dry ice. 10 μm thick methanol-fixed sections were subjected to staining with CD8-FITC (BioLegend, cat number 100705), PD1-PE (BioLegend, cat number 12-9981-82), CD31-FITC (PD Biosciences, cat number 553372), PDL1-PE (Invitrogen, cat number 12-5982-82), T-antigen (TAG, in house production), anti-rabbit Alexa Fluor 647 (secondary antibody for TAG, Abcam, cat number ab150075) and counterstained with DAPI (Roche cat number 10236276001). Sections were imaged on a Leica DM5500 microscope and an Olympus VS120 slide scanner. Images were processed with Adobe Photoshop and QuPath software.

Preclinical drug trial in Rip-Tag5 mice. To enroll Rip-Tag5 mice into the trial, mice from 22 weeks of age displaying blood glucose levels below 7 mmol/L were screened for the presence of PanNET islet tumors by ultrasound imaging using a Vevo2100 system with a MS550D 40 MHz transducer (Visual Sonic). Rip-Tag5 mice were randomly assigned to the different treatment groups based on the cumulative tumor burden. The average starting tumor burden was 28 mm2, the average starting age 25 weeks, and the average starting glucose level 5.8 mmol/L for the long-term efficacy studies. Tumors were monitored by ultrasound imaging every two weeks or every four weeks for complete responders for maximal 16 weeks. Blood glucose levels were monitored weekly using an Accu-Chek glucometer (Roche). The criteria for the endpoint were defined by the tumor burden, hypoglycemia (blood glucose at or below 3 mmol/L), general health status and loss of body weight (more than 15%).

Results

Figure 2A:
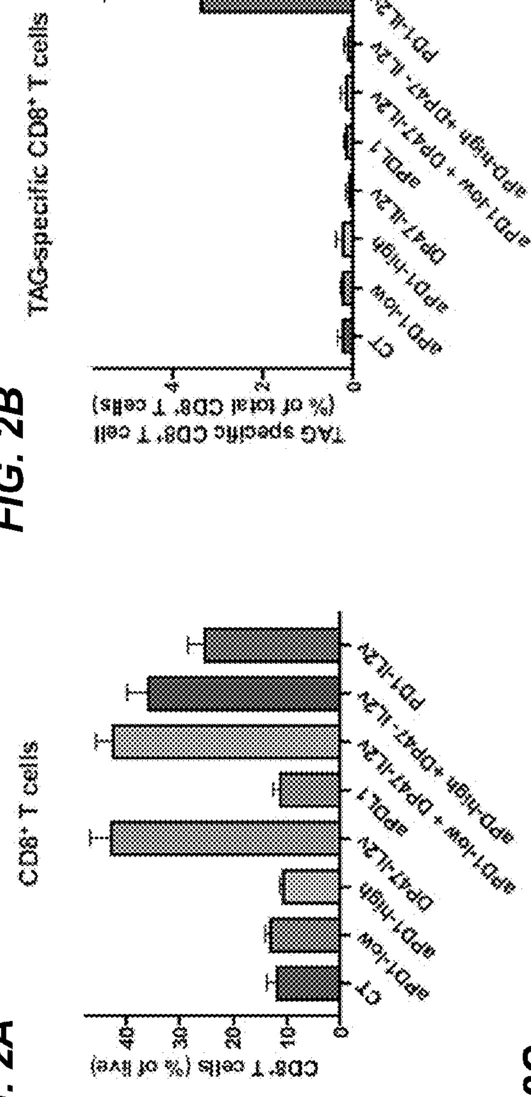
FIG. 2A-C. Presents that PD1-IL2v treatment results in expansion of TAG antigen-specific CD8+ T cells in the spleen and increases CD8+ T cell infiltrates in tumors of RipTag5 mice. Tumor bearing RipTag5 mice were treated with the indicated drugs for 14 days.
Figure 2B:
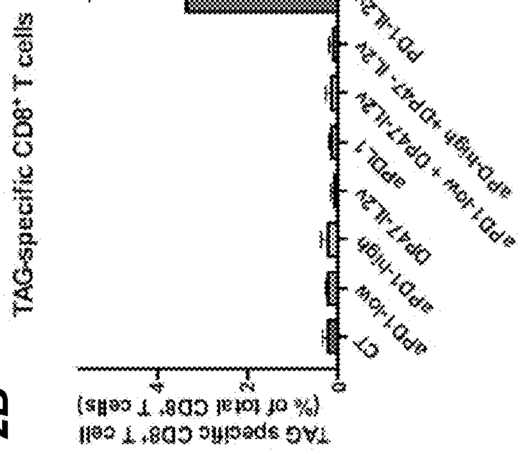
Figure 2C:
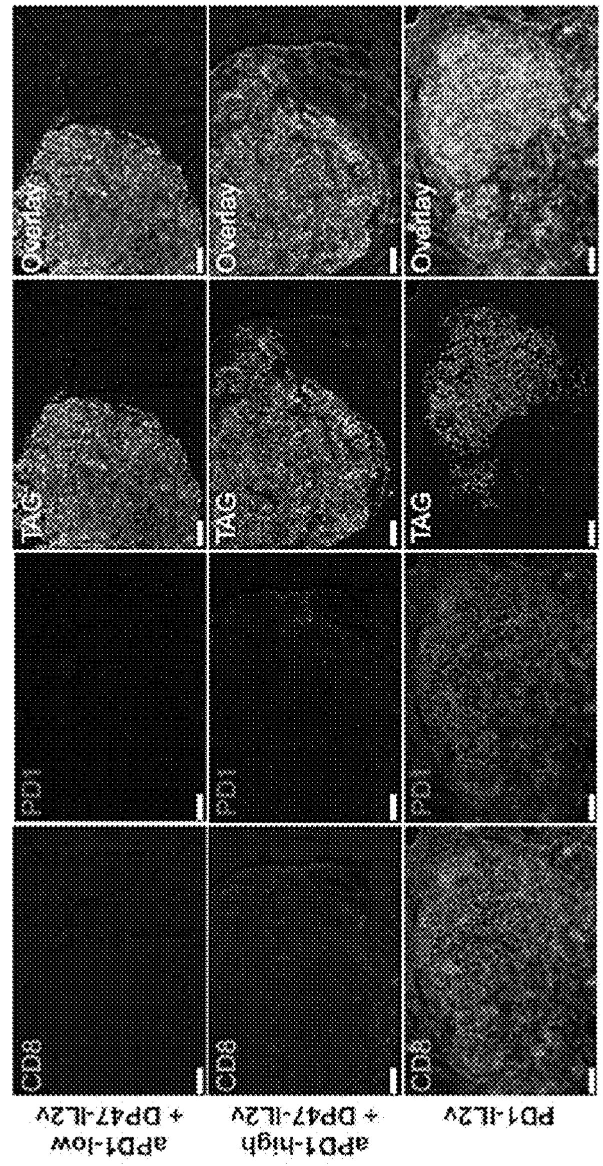

To assess the impact of the bi-specific molecule PD1-IL2v on targeting $CD8^+$ T cells, tumor bearing Rip-Tag5 mice were treated with PD1-IL2v for 14 days. The expansion of total $CD8^+$ T cells and $CD8^+$ T cells reactive against the tumor antigen TAG in the spleen was determined by flow cytometry and compared to single treatments of anti-PD1, DP47-IL2v, anti-PDL1 and anti-PD1+DP47-IL2v combination treatment. For anti-PD1 two concentrations were used; anti-PD1-low is equimolar to PD1 in the bi-specific molecule and anti-PD1-high is the therapeutic dose used for this drug. Treatment of DP47-IL2v either alone or combined with anti-PD1 resulted in a 3 to 4-fold increase in total $CD8^+$ T cells compared to untreated control mice (FIG. 2A). Similarly, PD1-IL2v treatment led to a 2.5-fold expansion of total $CD8^+$ T cells in the spleen of Rip-Tag5 mice (FIG. 2A). While DP47-IL2v potently increased the total $CD8^+$ T cell population, TAG-specific $CD8^+$ T cells were only expanded upon PD1-IL2v treatment, when the IL2v molecule was linked to the PD1 moiety. The enhanced tumor antigen-specific $CD8^+$ T cells generation upon PD1-IL2v treatment translated into an increased infiltration of $CD8^+$ T cells at the tumor site, whereas treatments of anti-PD1 combined with DP47-IL2v only modestly increased intratumoral $CD8^+$ T cells (FIG. 2C). The term "anti-PD", as used e.g. in anti-PD-L1 or anti-PD1, is abbreviated "aPD" in FIG. 2A-C, FIG. 3D and FIG. 4A-B.

To evaluate the efficacy of PD1-IL2v in a therapeutic setting, Rip-Tag5 mice were treated with PD1-IL2v for eight weeks. Rip-Tag5 mice were enrolled into trials based on the tumor size determined by ultrasound imaging and the tumor growth was monitored over a 12 week period. The cumulative starting tumor burden ranged from 20 to 40 $mm^2$. Pancreatic neuroendocrine tumors (PanNET) that develop in RipTag5 mice grew at a doubling time rate of four weeks in untreated mice (FIG. 3A). Treatment of PD1-IL2v led to tumor size shrinkage in all the mice.

After an initial decrease in the first four weeks of the treatment 50% of the mice acquired resistance to PD1-IL2v and the tumors progressed (FIG. 3B).

To investigate mechanisms of acquired resistance to PD1-IL2v therapy, tumors resistant to PD-IL2v were analyzed. Analyses of these relapsed tumors revealed an upregulation of PDL1 in particular on the CD31 positive tumor vasculature (FIG. 3C). Untreated PanNET tumors stained negative for PDL1, indicating that the observed upregulated of PDL1 upon PD1-IL2v could be a mechanism of resistance (FIG. 3C). We hypothesized that combination of PD1-IL2v with anti-PDL1 could result in an additive therapeutic benefit preventing tumor relapse. While anti-PDL1 monotherapy in tumor bearing Rip-Tag5 mice did not result in tumor regression (FIG. 3D), anti-PDL1 combined with PD1-IL2v substantially improved PD1-IL2v monotherapy. Over the observed time range of 12 weeks all the mice treated with PD1-IL2v combined with anti-PDL1 showed tumor regression without development of resistance to the combination therapy (FIG. 3E). Analysis of the tumor growth curves revealed that compared to PD1-IL2v the combination therapy resulted in an enhanced tumor regression rate within the first two weeks of treatment, indicating that blocking PDL1 at an early time point might be required to improve PD1-IL2v monotherapy. Collectively, the data revealed that combining PD1-IL2v with anti-PDL1 increases the therapeutic efficacy of PD1-IL2v and prevents tumor relapse in a mouse model of PanNET.

Figure 4B:
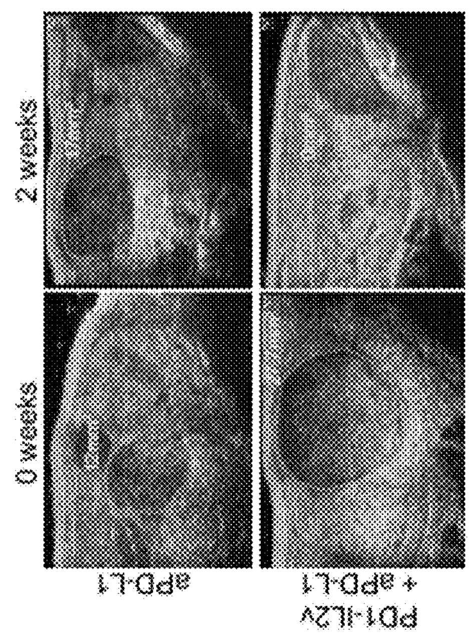
FIG. 4A-B. Presents that the combination therapy with anti-PD-L1 improves the efficacy of PD1-IL2v.
Figure 4A:
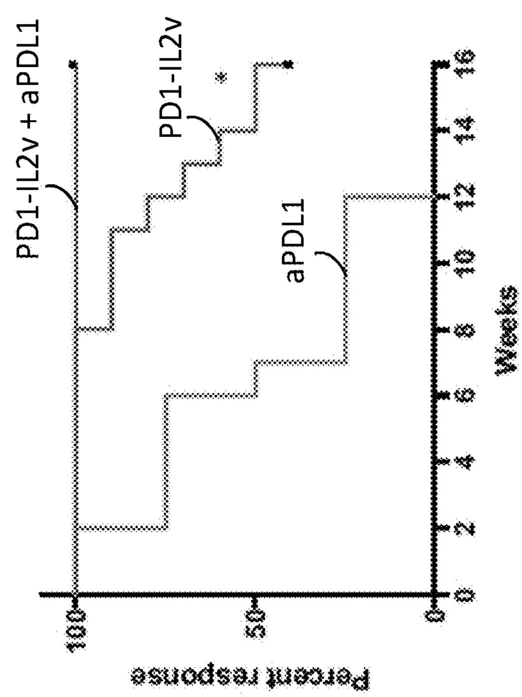

Tumor-bearing Rip-Tag5 mice were subjected to combinatorial drug treatment with PD1-IL2v and anti-PD-L1, and the tumor progression was monitored by ultrasound imaging for 16 weeks. FIG. 4A presents the response rate represented as survival graph. Two mice in the PD-IL2v and one mouse in the PD1-IL2v+anti-PD-L1 treatment group developed severe hyperglycemia due to the complete response and had to be euthanized. These mice were still considered as complete responders in the graph. FIG. 4B shows representative ultrasound images of tumors upon 0 and 2 weeks of anti-PD-L1 and PD1-IL2v+anti-PD-L1 treatment, including complete a responder upon PD1-IL2v treatment combined with anti-PD-L1.

| SEQ ID NO | Name | Sequence |
|---|---|---|
| 1 | human IL-2 (C125A) | APTSSSTKKTQLQLEHLLLDLQMILNGINNYKNPKLTRMLTFKFYMP KKATELKHLQCLE EELKPLEEVLNLAQSKNFHLRPRDLISNINVIVLELKGSETTFMCEYAD ETATIVEFLNR WITFAQSIISTLT |
| 2 | quadruple mutant | APASSSTKKTQLQLEHLLLDLQMILNGINNYKNPKLTRMLTAKFAMP KKATELKHLQCLE |

-continued

| SEQ ID NO | Name | Sequence |
|---|---|---|
| | human IL-2 (IL-2 qm or IL2v) | EELKPLEEVLNGAQSKNFHLRPRDLISNINVIVLELKGSETTFMCEYA DETATIVEFLNR WITFAQSIISTLT |
| 3 | human PD-L1 (including signal sequence) | MRIFAVFIFMTYWHLLNAFTVTVPKDLYVVEYGSNMTIECKFPVEKQ LDLAALIVYWEME DKNIIQFVHGEEDLKVQHSSYRQRARLLKDQLSLGNAALQITDVKLQ DAGVYRCMISYGG ADYKRITVKVNAPYNKINQRILVVDPVTSEHELTCQAEGYPKAEVIW TSSDHQVLSGKTT TTNSKREEKLFNVTSTLRINTTTNEIFYCTFRRLDPEENHTAELVIPELP LAHPPNERTH LVILGAILLCLGVALTFIFRLRKGRMMDVKKCGIQDTNSKKQSDTHLE ET |
| 4 | Human PD-1 including signal sequence | MQIPQAPWPVVWAVLQLGWRPGWFLDSPDRPWNPPTFSPALL VVTEGDNATFTCSFSNTSESFVLNWYRMSPSNQTDKLAAFPED RSQPGQDCRFRVTQLPNGRDFHMSVVRARRNDSGTYLCGAISL APKAQIKESLRAELRVTERRAEVPTAHPSPSPRPAGQFQTLVV GVVGGLLGSLVLLVWVLAVICSRAARGTIGARRTGQPLKEDP SAVPVFSVDYGELDFQWREKTPEPPVPCVPEQTEYATIVFPSG MGTSSPARRGSADGPRSAQPLRPEDGHCSWPL |
| 5 | Heavy chain variable domain VH of anti-PD-1 | EVQLLESGGGLVQPGGSLRLSCAASGFSFSSYTMSWVRQAP GKGLEWVATISGGGRDIYYPDSVKGRFTISRDNSKNTLYLQ MNSLRAEDTAVYYCVLLTGRVYFALDSWGQGTLVTVSS |
| 6 | Light chain variable domain VL of anti-PD-1 | DIVMTQSPDSLAVSLGERATINCKASESVDTSDNSFIHWYQQ KPGQSPKLLIYRSSTLESGVPDRFSGSGSGTDFTLTISSLQAED VAVYYCQQNYDVPWTFGQGTKVEIK |
| 7 | PD-1 IL2v - HC with IL2v (Fc knob, LALAPG) | Evqllesggglvqpggslrlscaasgfs fssytmswvrqapgkglewvatisgg grdiyypdsvkgrftisrdns kntlylq mnslraedtavyycvlltgrvyfaldsw gqgtlvtvssastkgpsvfplapssksts ggtaalgclvkdyfpepvtvswnsgal tsgvhtfpavlqssglyslssvvtvpsssl gtqtyicnvnhkpsntkvdkkvepksc dkthtcppcpapeaaggpsvflfppkp kdtlmisrtpevtcvvvdvshedpevkfnwy vdgvevhnaktkpreeqynstyrvvsv ltvlhqdwlngkeykckvsnkalgapiektisk akgqprepqvytlppcrdeltknqvslwcl vkgfypsdiavewesngqpennykttpp vldsdgsfflyskltvdksrwqqgnvfs csvmhealhnhytqkslslspgggggsg gggsggggsapassstkktqlqlehllldl qmilnginnyknpkltrmltakfamp kkatelkhlqcleeelkpleevlngaqsk nfhlrprdlisninvivlelkgsettfmceyadetativeflnrwitfaqsiistlt |
| 8 | PD-1 IL2v - HC without IL2v (Fc hole, LALAPG, HYRF) | Evqllesggglvqpggslrlscaasgfsfssytmswvrqapgkglewvatisgggrdiyypdsv kgrftisrdnskntlylqmnslraedtavyycvlltgrvyfaldswgqgtlvtvssas-tkgpsvfpl apsskstsggtaalgclvkdyfpepvtvswnsgaltsgvhtfpavlqssglyslssvvtvpssslg tqtyicnvnhkpsntkvdkkvepkscdkthtcppcpapeaaggpsvflfppkpkdtlmisrtp evtcvvvdvshedpevkfnwyvdgvevhnaktkpreeqynstyrvvsvltvlhqdwlngke ykckvsnkalgapiektiskakgqprepqvctlppsrdeltknqvslscavkgfypsdiavew esngqpennykttppvldsdgsfflvskltvdksrwqqgnvfscsvmhealhnrftqkslslsp |
| 9 | PD-1 IL2v - LC | Divmtqspdslavslgeratinckasesvdtsdnsfihwyqqkpgqspklliyrsstlesgvpd rfsgsgsgtdftltisslqaedvavyycqqnydvpwtfgqgtkveikrtvaapsvfifppsdeql ksgtasvvcllnnfypreakvqwkvdnalqsgnsqesvteqdskdstyslsstltlskadyekh kvyacevthqglsspvtksfnrgec |
| 10 | Murine heavy chain variable domain VH of anti-PD-1 | EVQLQESGPGLVKPSQSLSLTCSVTGYSITSSYRWNWIRKFPGNRLEW M GYINSAGISNYNPSLKRRISITRDTSKNQFFLQVNSVTTEDAATYYCAR SD NMGTTPFTYWGQGTLVTVSSASTTAPSVYPLAPVCGDTTGSSVTLGC LV KGYFPEPVTLTWNSGSLSSGVHTFPAVLQSDLYTLSSSVTVTSSTWPS QS] TCNVAHPASSTKVDKKIEPRGPTIKPCPPCKCPAPNAAGGPSVFIFPPKI KD VLMISLSPIVTCVVVDVSEDDPDVQISWFVNNVEVHTAQTQTHREDY |

-continued

| SEQ ID NO | Name | Sequence |
|---|---|---|
| | | NST<br>LRVVSALPIQHQDWMSGKEFKCKVNNKDLGAPIERTISKPKGSVRAP<br>QVYV<br>LPPPEEEMTKKQVTLTCMVTDFMPEDIYVEWTNNGKTELNYKNTEP<br>VLDS<br>DGSYFMYSKLRVEKKNWVERNSYSCSVVHEGLHNHHTTKSFSRTPG<br>K |
| 11 | Murine light chain variable domain VL of anti-PD-1 | DIVMTQGTLPNPVPSGESVSITCRSSKSLLYSDGKTYLNWYLQ<br>RPGQSPQLLIYWMSTRASGVSDRFSGSGSGTDFTLKISGVEAE<br>DVGIYYCQQGLEFPTFGGGTKLELKRTDAAPTVSIFPPSSEQLTS<br>GGASVVCFLNNFYPKDINVKWKIDGSERQNGVLNSWTDQDSK<br>DSTYSMSSTLTLTKDEYERHNSYTCEATHKTSTSPIVKSFNRNEC |
| 12 | Murine PD-1 surrogate IL2v - HC with IL2v | Evqlqesgpglvkpsqslsltcsvtgysitssyrwnwirkfpgnrlewmgyinsagisnynp<br>slkrrisitrdtsknqfflqvnsvttedaatyycarsdnmgttpftywgqgtlvtvssakttppsv<br>yplapgsaaqtnsmvtlgclvkgyfpepvtvtwnsgslssgvhtfpavlqsdlytlsssvtvps<br>stwpsqtvtcnvahpasstkvdkkivprdcgckpcictvpevssvfifppkpkdvltitltpkv<br>tcvvvaiskddpevqfswfvddvevhtaqtkpreeqinstfrsvselpimhqdwlngkefkcr<br>vnsaafgapiektisktkgrpkapqvytipppkeqmakdkvsltcmitnffpeditvewqwn<br>gqpaenydntqpimdtdgsyfvysdlnvqksnweagntftcsvlheglhnhhtekslshsp<br>gggggsgggggggsapassstsstaeaqqqqqqqqqqhleqllmdlqellsrmenyr<br>nlklprmltakfalpkqatelkdlqcledelgplrhvldgtqsksfqledaenfis-<br>nirvtvvklkgs<br>dntfecqfddesatvvdflrrwiafaqsiistspq |
| 13 | Murine surrogate PD-1 IL2v - HC without IL2v | Evqlqesgpglvkpsqslsltcsvtgysitssyrwnwirkfpgnrlewmgyinsagisnynps<br>lkrrisitrdtsknqfflqvnsvttedaatyycarsdnmgttpftywgqgtlvtvs-<br>sakttppsvyp<br>lapgsaaqtnsmvtlgclvkgyfpepvtvtwnsgslssgvhtfpavlqsdlytlsssvtvpsstw<br>psqtvtcnvahpasstkvdkkivprdcgckpcictvpevssvfifppkpkdvltitltpkvtcvv<br>vaiskddpevqfswfvddvevhtaqtkpreeqinstfrsvselpimhqdwlngkefkcrvnsa<br>afgapiektisktkgrpkapqvytipppkkqmakdkvsltcmitnffpeditvewqwngqpa<br>enykntqpimktdgsyfvysklnvqksnweagntftcsvlheglhnhhtekslshsp |
| 14 | Murine surrogate PD-1 IL2v - LC | Divmtqgtlpnpvpsgesvsitcrssksllysdgktylnwylqrpgqspqlliywmstrasgvs<br>drfsgsgsgtdftlkisgveaedvgiyycqq-<br>glefptfgggtklelkrtdaaptvsifppsseqltsg<br>gasvvcflnnfypkdinvkwkidgserqngvlnswtdqdskdstysmsstltltkdeyerhns<br>ytceathktstspivksfnrnec |
| 15 | Heavy chain variable domain VH of anti-PD-L1 | EVQLVESGGGLVQPGGSLRLSCAASGFTFSDSWIH<br>WVRQAPGKGLEWVAWISPYGGSTYYADSVKGRFTISA<br>DTSKNTAYLQMNSLRAEDTAVYYCARRHWPGGFDY<br>WGQGTLVTVSS |
| 16 | Light chain variable domain LH of anti PD-L1 | DIQMTQSPSSLSASVGDRVTITCRASQDVSTAVAWYQ<br>QKPGKAPKLLIYSASFLYSGVPSRFSGSGSGTDFTLTI SSLQPE<br>DFATYYCQQYLYHPATFGQGTKVEIK |
| 17 | Heavy chain-Fc of anti-PD-L1 | EVQLVESGGG LVQPGGSLRL SCAASGFTFS DSWIHWVRQA<br>PGKGLEWVAW ISPYGGSTYY ADSVKGRFTI SADTSKNTAY<br>LQMNSLRAED TAVYYCARRH WPGGFDYWGQ GTLVTVSSAS<br>TKGPSVFPLA PSSKSTSGGT AALGCLVKDY FPEPVTVSWN<br>SGALTSGVHT FPAVLQSSGL YSLSSVVTVP SSSLGTQTYI<br>CNVNHKPSNT KVDKKVEPKS CDKTHTCPPC PAPELLGGPS<br>VFLFPPKPKD TLMISRTPEV TCVVVDVSHE DPEVKFNWYV<br>DGVEVHNAKT KPREEQYAST YRVVSVLTVL HQDWLNGKEY<br>KCKVSNKALP APIEKTISKA KGQPREPQVY TLPPSREEMT<br>KNQVSLTCLV KGFYPSDIAV EWESNGQPEN NYKTTPPVLD<br>SDGSFFLYSK LTVDKSRWQQ GNVFSCSVMH EALHNHYTQK<br>SLSLSPGK |
| 18 | Light chain-Fc of anti-PD-L1 | DIQMTQSPSS LSASVGDRVT ITCRASQDVS TAVAWYQQKP<br>GKAPKLLIYS ASFLYSGVPS RFSGSGSGTD FTLTISSLQP<br>EDFATYYCQQ YLYHPATFGQ GTKVEIKRTV AAPSVFIFPP<br>SDEQLKSGTA SVVCLLNNFY PREAKVQWKV DNALQSGNSQ<br>ESVTEQDSKD STYSLSSTLT LSKADYEKHK VYACEVTHQG<br>LSSPVTKSFN RGEC |

-continued

| SEQ ID NO | Name | Sequence |
|---|---|---|
| 19 | Heavy chain variable domain VH of 6E11 | EVQLQQSGPELVKPGASVKLSCKTSGTFTDYYMTWVKQSHGKSLEW IGDIN PNNDIITYNQKFNDKATLTVDKSSSTASMELRSLRSDDSAVYYCARG DPR SWFPYWGQGTLVTVSA |
| 20 | Light chain variable domain LH of 6E11 | DIVLTQSPASLAVSLGQRATISCRASESVEFYG SLMRWYQQKPGQPPKLLIYAASNVESGVPA RFSGSGSGTDFSLNIHPVEEDDIAMYFCQQSRKVPLTFGAGTKLEIK |
| 21 | heavy chain-Fc of 6E11-muIgG1 | EVQLQQSGPELVKPGASVKLSCKTSGYTFTDYYMTW VKQSHGKSLEWIGDINPNNDIITYNQKFNDKATLTVD KSSSTASMELRSLRSDDSAVYYCARGDPRSWFPYWG QGTLVTVSAAKTTPPSVYPLAPGSAAQTNSMVTLGCL VKGYFPEPVTVTWNSGSLSSGVHTFPAVLQSDLYTLSS SVTVPSSTWPSQTVTCNVAHPASSTKVDKKIVPRDCG CKPCICTVPEVSSVFIFPPKPKDVLTITLTPKVTCVVVAI SKDDPEVQFSWFVDDVEVHTAQTKPREEQINSTFRS VSELPIMHQDWLNGKEFKCRVNSAAFGAPIEKTISKT KGRPKAPQVYTIPPPKEQMAKDKVSLTCMITNFFPED ITVEWQWNGQPAENYKNTQPIMDTDGSYFVYSKLN VQKSNWEAGNTFTCSVLHEGLHNHHTEKSLSHSPGK |
| 22 | Light chain-Fc of 6E11-muIgG1 | DIVLTQSPASLAVSLGQRATISCRASESVEFYGTSLMR WYQQKPGQPPKLLIYAASNVESGVPARFSGSGSGTD FSLNIHPVEEDDIAMYFCQQSRKVPLTFGAGTKLEIKR ADAAPTVSIFPPSSEQLTSGGASVVCFLNNFYPKDINV KWKIDGSERQNGVLNSWTDQDSKDSTYSMSSTLTLT KDEYERHNSYTCEATHKTSTSPIVKSFNRNEC |
| 23 | Heavy chain-Fc of 6E11-muIgG2a | EVQLQESGPGLVKPSQSLSLTCSVTGYSITSSYRWNWIR KFPGNRLEWMGYINSAGISNYNPSLKRRISITRDTSKNQ FFLQVNSVTTEDAATYYCARSDNMGTTPFTYWGQGTL VTVSSASTTAPSVYPLAPVCGDTTGSSVTLGCLVKGYFPE PVTLTWNSGSLSSGVHTFPAVLQSDLYTLSSSVTVTSSTW PSQSITCNVAHPASSTKVDKKIEPRGPTIKPCPPCKCPAP NAAGGPSVFIFPPKIKDVLMISLSPIVTCVVVDVSEDDPD VQISWFVNNVEVHTAQTQTHREDYNSTLRVVSALPIQH QDWMSGKEFKCKVNNKDLGAPIERTISKPKGSVRAPQV YVLPPPEEEMTKKQVTLTCMVTDFMPEDIYVEWTNNGK TELNYKNTEPVLDSDGSYFMYSKLRVEKKNWVERNSYSC SVVHEGLHNHHTTKSFSRTPGK |
| 24 | Light chain-Fc of 6E11-muIgG2a | DIVMTQGTLPNPVPSGESVSITCRSSKSLLYSDGKTYLNW YLQRPGQSPQLLIYWMSTRASGVSDRFSGSGSGTDFTLK ISGVEAEDVGIYYCQQGLEFPTFGGGTKLELKRTDAAPTV SIFPPSSEQLTSGGASVVCFLNNFYPKDINVKWKIDGSERQ NGVLNSWTDQDSKDSTYSMSSTLTLTKDEYERHNSYTCEA THKTSTSPIVKSFNRNEC |
| 25 | Heavy chain-Fc of S70-muIgG1 | EVQLVESGGGLVQPGGSLRLSCAASGFTFSDSWIHWVR QAPGKGLEWVAWISPYGGSTYYADSVKGRFTISADTSK NTAYLQMNSLRAEDTAVYYCARRHWPGGFDYWGQGT LVTVSAKTTPPSVYPLAPGSAAQTNSMVTLGCLVKGYFP EPVTVTWNSGSLSSGVHTFPAVLQSDLYTLSSSVTVPSST WPSQTVTCNVAHPASSTKVDKKIVPRDCGCKPCICTVPE VSSVFIFPPKPKDVLTITLTPKVTCVVVAISKDDPEVQFSW FVDDVEVHTAQTKPREEQINSTFRSVSELPIMHQDWLN GKEFKCRVNSAAFGAPIEKTISKTKGRPKAPQVYTIPPPKE QMAKDKVSLTCMITNFFPEDITVEWQWNGQPAENYKN TQPIMDTDGSYFVYSKLNVQKSNWEAGNTFTCSVLHEGL HNHHTEKSLSHSPGK |
| 26 | Light chain-Fc of S70-muIgG1 | DIQMTQSPSSLSASVGDRVTITCRASQDVSTAVAWYQ QKPGKAPKLLIYSASFLYSGVPSRFSGSGSGTDFTLTISSL QPEDFATYYCQQYLYHPATFGQGTKVEIKRADAAPTVS IFPPSSEQLTSGGASVVCFLNNFYPKDINVKWKIDGSER QNGVLNSWTDQDSKDSTYSMSSTLTLTKDEYERHNSYT CEATHKTSTSPIVKSFNRNEC |

-continued

| SEQ ID NO | Name | Sequence |
|---|---|---|
| 27 | Murine surrogate DP47-IL2v - HC with IL2v | EVQLLESGGGLVQPGGSLRLSCAASGFTFSSYAMSWVRQAPGKGLE<br>WV<br>SAISGSGGSTYYADSVKGRFTISRDNSKNTLYLQMNSLRAEDTAVYY<br>CAKG<br>SGFDYWGQGTLVTVSSASTKGPSVFPLAPSSKSTSGGTAALGCLVKD<br>YFPE<br>PVTVSWNSGALTSGVHTFPAVLQSSGLYSLSSVVTVPSSSLGTQTYIC<br>NVN<br>HKPSNTKVDKKVEPKSCDKTHTCPPCPAPEAAGGPSVFLFPPKPKDTL<br>MISR<br>TPEVTCVVVDVSHEDPEVKFNWYVDGVEVHNAKTKPREEQYNSTYR<br>VVSV<br>LTVLHQDWLNGKEYKCKVSNKALGAPIEKTISKAKGQPREPQVYTLP<br>PCRDEL<br>TKNQVSLWCLVKGFYPSDIAVEWESNGQPENNYKTTPPVLDSDGSFF<br>LYSKL<br>TVDKSRWQQGNVFSCSVMHEALHNHYTQKSLSLSPGGGGGSGGGGS<br>GGG<br>GSAPASSSTKKTQLQLEHLLLDLQMILNGINNYKNPKLTRMLTAKFA<br>MPKKA<br>TELKHLQCLEEELKPLEEVLNGAQSKNFHLRPRDLISNINVIVLELKGS<br>ETTFMCE YADETATIVEFLNRWITFAQSIISTLT |
| 28 | Murine surrogate DP47-IL2v - HC without IL2v | EVQLLESGGGLVQPGGSLRLSCAASGFTFSSYAMSWVRQAPGKGLE<br>WVSAI<br>SGSGGSTYYADSVKGRFTISRDNSKNTLYLQMNSLRAEDTAVYYCA<br>KGSGFD<br>YWGQGTLVTVSSASTKGPSVFPLAPSSKSTSGGTAALGCLVKDYFPE<br>PVTVS<br>WNSGALTSGVHTFPAVLQSSGLYSLSSVVTVPSSSLGTQTYICNVNHK<br>PSNTK<br>VDKKVEPKSCDKTHTCPPCPAPEAAGGPSVFLFPPKPKDTLMISRTPE<br>VTCVV<br>VDVSHEDPEVKFNWYVDGVEVHNAKTKPREEQYNSTYRVVSVLTV<br>LHQDWL<br>NGKEYKCKVSNKALGAPIEKTISKAKGQPREPQVCTLPPSRDELTKN<br>QVSLSCA<br>VKGFYPSDIAVEWESNGQPENNYKTTPPVLDSDGSFFLVSKLTVDKS<br>RWQQG NVFSCSVMHEALHNHYTQKSLSLSPGK |
| 29 | Murine surrogate DP47-IL2v -LC | EIVLTQSPGTLSLSPGERATLSCRASQSVSSSYLAWYQQKPGQAPRLLI<br>YG<br>ASSRATGIPDRFSGSGSGTDFTLTISRLEPEDFAVYYCQQYGSSPLTFG<br>QG<br>TKVEIKRTVAAPSVFIFPPSDEQLKSGTASVVCLLNNFYPREAKVQWK<br>VD<br>NALQSGNSQESVTEQDSKDSTYSLSSTLTLSKADYEKHKVYACEVTH<br>QGLS SPVTKSFNRGEC |

What is claimed is:

1. A therapeutic method of treating cancer comprising administering to a subject a combination therapy comprising (a) a programmed death 1 polypeptide (PD-1)-targeted interleukin 2 (IL-2) variant immunocytokine in combination with (b) an antibody which binds to human programmed death ligand 1 (PD-L1), wherein the PD-1-targeted IL-2 variant immunocytokine comprises:

i) a heavy chain variable domain VH of SEQ ID NO: 5 and a light chain variable domain VL of SEQ ID NO: 6, and the polypeptide sequence of SEQ ID NO: 2, or ii) the polypeptide sequences of SEQ ID NO: 7, and SEQ ID NO: 8 and SEQ ID NO: 9, or iii) the polypeptide sequences of SEQ ID NO: 12, and SEQ ID NO: 13 and SEQ ID NO: 14, and wherein the antibody which binds to human PD-L1 comprises a heavy chain variable domain VH of SEQ ID NO: 19 and a light chain variable domain VL of SEQ ID NO: 20.

2. The method of claim 1, wherein the cancer is selected from the group consisting of breast cancer, lung cancer, colon cancer, ovarian cancer, melanoma cancer, bladder cancer, renal cancer, kidney cancer, liver cancer, head and neck cancer, colorectal cancer, pancreatic cancer, gastric carcinoma cancer, esophageal cancer, mesothelioma, prostate cancer, leukemia, lymphoma, and multiple myeloma.

3. The method of claim 1, wherein the combination therapy is for the treatment of metastasis.

4. The method of claim 1, wherein the combination therapy is for treating or delaying progression of tumor immunity.

5. The method of claim 1, wherein the combination therapy stimulates an immune response or function.

6. The method of claim 5, wherein the immune response or function comprises T cell activity.

7. The method of claim 1, wherein the antibody component of the immunocytokine and the antibody are of human IgG1 subclass or human IgG4 subclass.

8. The method of claim 7, wherein the antibodies have reduced or minimal effector function.

9. The method of claim 8, wherein the minimal effector function results from an effectorless Fc mutation.

10. The method of claim 9, wherein the effectorless Fc mutation is L234A/L235A or L234A/L235A/P329G or N297A or D265A/N297A.

11. The method of claim 1, wherein the subject is treated with or was pre-treated with an additional immunotherapy.

12. The method of claim 11, wherein the additional immunotherapy comprises adoptive cell transfer, administration of monoclonal antibodies, administration of cytokines, administration of a cancer vaccine, T cell engaging therapies, or any combination thereof.

13. The method of claim 12, wherein the adoptive cell transfer comprises administering chimeric antigen receptor expressing T-cells (CAR T-cells), T-cell receptor (TCR) modified T-cells, tumor-infiltrating lymphocytes (TIL), chimeric antigen receptor (CAR)-modified natural killer cells, T cell receptor (TCR) transduced cells, or dendritic cells, or any combination thereof.

14. A therapeutic method for (i) inhibiting tumor growth in a tumor; and/or (ii) enhancing median and/or overall survival of subjects with a tumor, wherein PD-1 is presented on immune cells or in a tumor cell environment, the method comprising administering to a subject a combination therapy comprising (a) a PD-1-targeted IL-2 variant immunocytokine in combination with (b) an antibody which binds to human PD-L1, wherein the PD-1-targeted IL-2 variant immunocytokine comprises:

i) a heavy chain variable domain VH of SEQ ID NO: 5 and a light chain variable domain VL of SEQ ID NO: 6, and the polypeptide sequence of SEQ ID NO: 2, or ii) the polypeptide sequences of SEQ ID NO: 7, and SEQ ID NO: 8 and SEQ ID NO: 9, or iii) the polypeptide sequences of SEQ ID NO: 12, and SEQ ID NO: 13 and SEQ ID NO: 14;

and wherein the antibody which binds to human PD-L1 comprises:

a heavy chain variable domain VH of SEQ ID NO: 19 and a light chain variable domain VL of SEQ ID NO: 20.

15. The method of claim 14, wherein the antibody component of the immunocytokine and the antibody are of human IgG1 subclass or human IgG4 subclass.

16. The method of claim 15, wherein the antibodies have reduced or minimal effector function.

17. The method of claim 16, wherein the minimal effector function results from an effectorless Fc mutation.

18. The method of claim 17, wherein the effectorless Fc mutation is L234A/L235A or L234A/L235A/P329G or N297A or D265A/N297A.

19. The method of claim 14, wherein the subject is treated with or was pre-treated with an additional immunotherapy.

20. The method of claim 19, wherein the additional immunotherapy comprises adoptive cell transfer, administration of monoclonal antibodies, administration of cytokines, administration of a cancer vaccine, T cell engaging therapies, or any combination thereof.

21. The method of claim 20, wherein the adoptive cell transfer comprises administering chimeric antigen receptor expressing T-cells (CAR T-cells), T-cell receptor (TCR) modified T-cells, tumor-infiltrating lymphocytes (TIL), chimeric antigen receptor (CAR)-modified natural killer cells, T cell receptor (TCR) transduced cells, or dendritic cells, or any combination thereof.

* * * * *